(12) United States Patent
Doshi et al.

(10) Patent No.: US 12,180,456 B2
(45) Date of Patent: Dec. 31, 2024

(54) TISSUE HEALING

(71) Applicant: AVITA Medical Americas, LLC, Valencia, CA (US)

(72) Inventors: Niraj Kumar Doshi, Valencia, CA (US); Jugal Kapadia, Valencia, CA (US); Matthew Krywcun, Laguna Niguel, CA (US); David Allen Fencil, Valencia, CA (US); David Melbye, Valencia, CA (US); Katie Bush, Marblehead, MA (US); Carl Swindle, San Clemente, CA (US); Paul Faucher, San Diego, CA (US); Matthew Richard Johnson, San Diego, CA (US); Adam Livingston, San Diego, CA (US); Michael MacCollum, San Diego, CA (US); Evan Misuraca, San Diego, CA (US); Kyle Stewart, San Diego, CA (US); Mikhail Tikh, San Diego, CA (US); Austin Wolf, San Diego, CA (US)

(73) Assignee: AVITA Medical Americas, LLC, Valencia, CA (US)

( * ) Notice: Subject to any disclaimer, the term of this patent is extended or adjusted under 35 U.S.C. 154(b) by 0 days.

(21) Appl. No.: 18/395,415

(22) Filed: Dec. 22, 2023

(65) Prior Publication Data

US 2024/0209296 A1    Jun. 27, 2024

Related U.S. Application Data

(60) Provisional application No. 63/533,586, filed on Aug. 18, 2023, provisional application No. 63/435,446, filed on Dec. 27, 2022.

(51) Int. Cl.
  *C12M 1/00*  (2006.01)
  *B01L 3/00*  (2006.01)
  (Continued)

(52) U.S. Cl.
  CPC ......... *C12M 41/48* (2013.01); *B01L 3/50255* (2013.01); *C12M 3/02* (2013.01);
  (Continued)

(58) Field of Classification Search
  None
  See application file for complete search history.

(56) References Cited

U.S. PATENT DOCUMENTS

| | | | |
|---|---|---|---|
| 1,356,794 | A | 10/1920 | Smith |
| 2,343,079 | A | 2/1944 | Pickwell |

(Continued)

FOREIGN PATENT DOCUMENTS

| | | |
|---|---|---|
| AU | PO2752 | 10/1996 |
| AU | 3990197 | 4/1998 |

(Continued)

OTHER PUBLICATIONS

"Zed Merrick, 2, Second Degree Burns are Healed with ReCell Skin Spray", HuffingtonPost, Feb. 20, 2012 (updated Apr. 17, 2012), in 2 pages. URL: https://www.huffingtonpost.co.uk/2012/02/20/zed-merrick-2-second-degree-burns-are-healed-after-he-is-sprayed-with-his-own-skin-cells_n_1288436.html.

(Continued)

*Primary Examiner* — Jyoti Nagpaul
(74) *Attorney, Agent, or Firm* — Knobbe, Martens, Olson & Bear LLP

(57) ABSTRACT

One or more methods for treating a tissue site comprises collecting a tissue sample that has keratinoytes and placing the tissue sample in a cartridge that has a well plate, positioning the cartridge within a base unit that has a tissue disaggregator, activating the base unit to rotate the well plate to align wells in the well plate with the tissue sample and the tissue disaggregator, operate the tissue disaggregator to separate the tissue sample to form a regenerative epidermal (Continued)

suspension, and provide the regenerative epidermal suspension to a tissue site to enhance healing of the tissue site.

20 Claims, 51 Drawing Sheets

(51) Int. Cl.
| | |
|---|---|
| *C12M 1/02* | (2006.01) |
| *C12M 1/12* | (2006.01) |
| *C12M 1/26* | (2006.01) |
| *C12M 1/32* | (2006.01) |
| *C12M 1/36* | (2006.01) |
| *C12M 3/00* | (2006.01) |
| *C12M 3/02* | (2006.01) |
| *C12M 3/04* | (2006.01) |
| *C12M 3/08* | (2006.01) |
| *G01N 1/28* | (2006.01) |

(52) U.S. Cl.
CPC .............. *C12M 3/08* (2013.01); *C12M 21/08* (2013.01); *C12M 23/12* (2013.01); *C12M 23/38* (2013.01); *C12M 23/42* (2013.01); *C12M 23/50* (2013.01); *C12M 25/04* (2013.01); *C12M 27/10* (2013.01); *C12M 33/00* (2013.01); *C12M 33/14* (2013.01); *C12M 41/18* (2013.01); *G01N 1/286* (2013.01); *B01L 2300/042* (2013.01); *G01N 2001/2866* (2013.01)

(56) References Cited

U.S. PATENT DOCUMENTS

| | | | |
|---|---|---|---|
| 3,608,553 A | 9/1971 | Balamuth |
| 3,647,632 A | 3/1972 | Johnson et al. |
| 3,860,706 A | 1/1975 | Ikeda et al. |
| 4,059,486 A | 11/1977 | Tolbert |
| 4,254,226 A | 3/1981 | Eisinger et al. |
| 4,304,866 A | 12/1981 | Green et al. |
| 4,350,768 A | 9/1982 | Tihon et al. |
| 4,377,010 A | 3/1983 | Fydelor et al. |
| 4,418,691 A | 12/1983 | Yannas et al. |
| 4,458,678 A | 7/1984 | Yannas et al. |
| 4,505,266 A | 3/1985 | Yannas et al. |
| 4,510,144 A | 4/1985 | Hadden et al. |
| 4,533,635 A | 8/1985 | Guedon born Saglier et al. |
| 4,595,102 A | 6/1986 | Cianci et al. |
| 4,649,115 A | 3/1987 | Safai et al. |
| 4,736,850 A | 4/1988 | Bowman et al. |
| 4,769,317 A | 9/1988 | Hefton |
| D304,794 S | 11/1989 | Sheard |
| 4,957,742 A | 9/1990 | Knighton |
| 5,000,963 A | 3/1991 | Hefton |
| 5,012,929 A | 5/1991 | Roosa |
| 5,035,708 A | 7/1991 | Alchas et al. |
| D321,054 S | 10/1991 | Cohn |
| 5,079,160 A | 1/1992 | Lacy et al. |
| 5,100,621 A | 3/1992 | Berke et al. |
| 5,139,031 A | 8/1992 | Guirguis |
| 5,145,770 A | 9/1992 | Tubo et al. |
| 5,292,655 A | 3/1994 | Wille, Jr. |
| D346,741 S | 5/1994 | McIntyre |
| 5,328,695 A | 7/1994 | Lucas et al. |
| 5,334,527 A | 8/1994 | Brysk |
| 5,352,668 A | 10/1994 | Burgeson et al. |
| 5,352,806 A | 10/1994 | Gunawardana et al. |
| 5,441,539 A | 8/1995 | Alchas et al. |
| 5,460,939 A | 10/1995 | Hansbrough et al. |
| 5,507,385 A | 4/1996 | Koloski et al. |
| 5,556,783 A | 9/1996 | Lavker et al. |
| 5,571,031 A | 11/1996 | Lemelson |
| 5,571,083 A | 11/1996 | Lemelson |
| 5,601,728 A | 2/1997 | Kayal et al. |
| 5,624,638 A | 4/1997 | Negrotti |
| 5,643,767 A | 7/1997 | Fischetti et al. |
| 5,710,043 A | 1/1998 | Pay |
| 5,720,981 A | 2/1998 | Eisinger |
| 5,786,207 A | 7/1998 | Katz et al. |
| 5,814,511 A | 9/1998 | Chang et al. |
| 5,866,167 A | 2/1999 | Van Bossuyt |
| 5,934,472 A | 8/1999 | Ramirez et al. |
| 5,955,343 A | 9/1999 | Holmes et al. |
| 5,994,129 A | 11/1999 | Armstrong et al. |
| D419,364 S | 1/2000 | Jarvis |
| 6,080,581 A | 6/2000 | Anderson et al. |
| 6,096,510 A | 8/2000 | Hochman |
| 6,207,451 B1 | 3/2001 | Dennis et al. |
| 6,291,240 B1 | 9/2001 | Mansbridge et al. |
| 6,372,494 B1 | 4/2002 | Naughton et al. |
| 6,432,666 B1 | 8/2002 | Hart |
| 6,454,097 B1 | 9/2002 | Blanco |
| 6,479,052 B1 | 11/2002 | Marshall et al. |
| 6,636,780 B1 | 10/2003 | Haitin et al. |
| 6,649,072 B2 | 11/2003 | Brandt et al. |
| 6,660,853 B2 | 12/2003 | Prescott |
| 6,830,149 B2 | 12/2004 | Merboth et al. |
| D501,760 S | 2/2005 | Bukowski |
| 6,861,250 B1 | 3/2005 | Cole et al. |
| 6,927,049 B2 | 8/2005 | Rubinsky et al. |
| 7,081,240 B1 | 7/2006 | Akella et al. |
| 7,155,306 B2 | 12/2006 | Haitin et al. |
| 7,371,399 B2 | 5/2008 | Prescott |
| 7,462,606 B2 | 12/2008 | Bellini et al. |
| 7,628,780 B2 | 12/2009 | Bonner et al. |
| 7,641,898 B2 | 1/2010 | Lyles |
| 7,655,465 B2 | 2/2010 | Sherley et al. |
| 7,767,452 B2 | 8/2010 | Kleinsek |
| D626,238 S | 10/2010 | Zinnanti |
| 7,850,983 B2 | 12/2010 | Sevrain et al. |
| 8,022,037 B2 | 9/2011 | Li et al. |
| 8,093,015 B2 | 1/2012 | Obermann et al. |
| 8,157,817 B2 | 4/2012 | Bonadio et al. |
| 8,162,247 B2 | 4/2012 | Faulker |
| 8,286,899 B2 | 10/2012 | Schowalter et al. |
| 8,323,638 B2 | 12/2012 | Rolland et al. |
| D687,546 S | 8/2013 | Baid |
| 8,524,492 B2 | 9/2013 | Liu et al. |
| 8,568,761 B2 | 10/2013 | Matheny |
| 8,580,564 B2 | 11/2013 | Brown et al. |
| 8,714,360 B2 | 5/2014 | Swayze et al. |
| 8,753,882 B2 | 6/2014 | Gold |
| 8,790,890 B2 | 7/2014 | Zorin et al. |
| 8,835,170 B2 | 9/2014 | Katz et al. |
| 8,893,995 B2 | 11/2014 | Taghizadeh et al. |
| 8,920,720 B2 | 12/2014 | Shah |
| D722,368 S | 2/2015 | Jones |
| 8,951,513 B2 | 2/2015 | Alt et al. |
| 9,011,684 B2 | 4/2015 | Kyle |
| 9,029,140 B2 | 5/2015 | Wood et al. |
| 9,057,064 B1 | 6/2015 | Dyer et al. |
| 9,062,288 B2 | 6/2015 | Vesey |
| D734,839 S | 7/2015 | Jones |
| 9,078,741 B2 | 7/2015 | Wood et al. |
| 9,150,826 B2 | 10/2015 | Isely et al. |
| D750,973 S | 3/2016 | McSweeney et al. |
| D775,828 S | 1/2017 | Wang |
| D777,435 S | 1/2017 | Hecht et al. |
| 9,663,760 B2 | 5/2017 | Taghizadeh et al. |
| 9,726,687 B2 | 8/2017 | Murali et al. |
| 9,757,422 B2 | 9/2017 | Burt |
| 9,795,761 B2 | 10/2017 | Lockwood et al. |
| 9,867,692 B2 | 1/2018 | Wood et al. |
| 9,909,094 B2 | 3/2018 | Cimino et al. |
| 9,926,530 B2 | 3/2018 | Vacher et al. |
| 9,963,676 B2 | 5/2018 | Broeckx et al. |
| 10,105,306 B2 | 10/2018 | Chan et al. |
| 10,138,457 B2 | 11/2018 | Cimino et al. |
| D854,853 S | 7/2019 | Bearsch et al. |
| 10,626,358 B2 | 4/2020 | Quick et al. |
| 10,626,370 B2 | 4/2020 | Vacher et al. |
| 10,631,974 B2 | 4/2020 | Wood et al. |
| 10,660,921 B2 | 5/2020 | Vesey et al. |

(56) References Cited

U.S. PATENT DOCUMENTS

| | | | |
|---|---|---|---|
| 10,729,536 B2 | 8/2020 | Wood et al. |
| 10,745,666 B2 | 8/2020 | Katz et al. |
| 10,801,001 B2 | 10/2020 | Brown et al. |
| 10,851,412 B2 | 12/2020 | Shoemaker et al. |
| 10,857,544 B2 | 12/2020 | Graziano et al. |
| 10,869,900 B2 | 12/2020 | Funk |
| 10,967,006 B2 | 4/2021 | Luttun et al. |
| D928,436 S | 8/2021 | Knapp |
| D929,766 S | 9/2021 | Huang |
| 11,124,752 B2 | 9/2021 | Quick et al. |
| D955,601 S | 6/2022 | York |
| D973,902 S | 12/2022 | Ahmed et al. |
| D994,141 S | 8/2023 | Doshi et al. |
| 11,987,787 B2 | 5/2024 | Doshi et al. |
| 2001/0048917 A1 | 12/2001 | Hoeffler et al. |
| 2002/0019060 A1 | 2/2002 | Petersen et al. |
| 2002/0048563 A1 | 4/2002 | Baetge et al. |
| 2002/0082692 A1 | 6/2002 | van Blitterswijk et al. |
| 2002/0106353 A1 | 8/2002 | Wood et al. |
| 2002/0114845 A1 | 8/2002 | DeVore et al. |
| 2002/0197631 A1 | 12/2002 | Lawrence et al. |
| 2003/0202965 A1 | 10/2003 | Seubert et al. |
| 2004/0005608 A1 | 1/2004 | Saghbini et al. |
| 2004/0110289 A1 | 6/2004 | Ludlow et al. |
| 2004/0219133 A1 | 11/2004 | Lyles |
| 2005/0026275 A1 | 2/2005 | Bahoric |
| 2005/0048034 A1 | 3/2005 | Fraser et al. |
| 2005/0070944 A1 | 3/2005 | Holl et al. |
| 2005/0084961 A1 | 4/2005 | Hedrick et al. |
| 2005/0255096 A1 | 11/2005 | Poder |
| 2005/0260175 A1 | 11/2005 | Hedrick et al. |
| 2005/0272147 A1 | 12/2005 | Sherley et al. |
| 2006/0018946 A1 | 1/2006 | Prescott |
| 2006/0257378 A1 | 11/2006 | Crumpler et al. |
| 2007/0042488 A1 | 2/2007 | Bornemann |
| 2007/0069054 A1 | 3/2007 | Shomi |
| 2007/0077601 A1 | 4/2007 | Ishihara et al. |
| 2007/0077658 A1 | 4/2007 | Kobayashi et al. |
| 2007/0116680 A1 | 5/2007 | Stegemann et al. |
| 2007/0134794 A1 | 6/2007 | Mangano |
| 2007/0184033 A1 | 8/2007 | Sevrain et al. |
| 2007/0286880 A1 | 12/2007 | Vasiliev et al. |
| 2008/0014181 A1 | 1/2008 | Ariff et al. |
| 2008/0038812 A1 | 2/2008 | Elson et al. |
| 2008/0081363 A1 | 4/2008 | Hutchins et al. |
| 2008/0194017 A1 | 8/2008 | Esser et al. |
| 2009/0017438 A1 | 1/2009 | Roy et al. |
| 2009/0202500 A1 | 8/2009 | Tamai et al. |
| 2010/0035815 A1 | 2/2010 | Li et al. |
| 2010/0159507 A1 | 6/2010 | Ting et al. |
| 2010/0196334 A1 | 8/2010 | Wood et al. |
| 2010/0255052 A1 | 10/2010 | Young Anze et al. |
| 2010/0274205 A1 | 10/2010 | Morelli et al. |
| 2010/0279405 A1 | 11/2010 | Peterson et al. |
| 2010/0285588 A1 | 11/2010 | Stubbers et al. |
| 2011/0008458 A1 | 1/2011 | Gandy et al. |
| 2011/0044527 A1 | 2/2011 | Tibbe et al. |
| 2011/0053269 A1 | 3/2011 | Suggs et al. |
| 2011/0070646 A1 | 3/2011 | Brown et al. |
| 2011/0082082 A1 | 4/2011 | Li et al. |
| 2011/0150848 A1 | 6/2011 | Wood et al. |
| 2011/0177015 A1 | 7/2011 | Friedlander |
| 2011/0232234 A1 | 9/2011 | Lockwood et al. |
| 2011/0233148 A1 | 9/2011 | Antonchuk et al. |
| 2011/0318315 A1 | 12/2011 | Aggarwal et al. |
| 2012/0043405 A1 | 2/2012 | Faulker et al. |
| 2012/0172985 A1 | 7/2012 | Altman et al. |
| 2012/0202715 A1 | 8/2012 | Partida-Sanchez et al. |
| 2012/0264689 A1 | 10/2012 | Mize |
| 2012/0269774 A1 | 10/2012 | Ichim et al. |
| 2012/0310401 A1 | 12/2012 | Shah |
| 2013/0051963 A1 | 2/2013 | Taylor |
| 2013/0177614 A1 | 7/2013 | Mantyla et al. |
| 2013/0237453 A1 | 9/2013 | Chander |
| 2013/0280754 A1 | 10/2013 | Souza |
| 2013/0295673 A1 | 11/2013 | Taghizadeh et al. |
| 2014/0248245 A1 | 9/2014 | Zorin et al. |
| 2014/0276362 A1 | 9/2014 | Alvarez |
| 2014/0363883 A1 | 12/2014 | Hayes et al. |
| 2015/0079153 A1 | 3/2015 | Quick et al. |
| 2015/0104825 A1 | 4/2015 | Peyvan |
| 2015/0110750 A1 | 4/2015 | Garza et al. |
| 2015/0182739 A1 | 7/2015 | Wood et al. |
| 2015/0232807 A1 | 8/2015 | Broeckx et al. |
| 2015/0352257 A1 | 12/2015 | Early |
| 2016/0024450 A1* | 1/2016 | Quick ............... C12M 21/08 |
| | | 435/379 |
| 2016/0113967 A1 | 4/2016 | Hedrick et al. |
| 2016/0122723 A1 | 5/2016 | Retting et al. |
| 2016/0340651 A1 | 11/2016 | Maslowski et al. |
| 2017/0049932 A1 | 2/2017 | Badylak et al. |
| 2017/0306287 A1 | 10/2017 | Kawarai et al. |
| 2018/0028569 A1 | 2/2018 | Flower |
| 2018/0098840 A1 | 4/2018 | Wood et al. |
| 2018/0280575 A1 | 10/2018 | Delaney et al. |
| 2018/0298320 A1 | 10/2018 | Nelson |
| 2019/0001290 A1 | 1/2019 | Fletcher |
| 2019/0031990 A1 | 1/2019 | Timmins et al. |
| 2019/0032017 A1 | 1/2019 | Zeigler |
| 2019/0059861 A1 | 2/2019 | Lough et al. |
| 2019/0071644 A1 | 3/2019 | Chi et al. |
| 2019/0085283 A1 | 3/2019 | Cimino et al. |
| 2019/0086324 A1 | 3/2019 | Marrinucci et al. |
| 2019/0127681 A1 | 5/2019 | Wurzer et al. |
| 2019/0345439 A1 | 11/2019 | Skardal et al. |
| 2019/0367964 A1 | 12/2019 | Izar et al. |
| 2020/0033232 A1 | 1/2020 | Lin et al. |
| 2020/0086003 A1 | 3/2020 | Cho et al. |
| 2020/0093951 A1 | 3/2020 | Quick |
| 2020/0093952 A1 | 3/2020 | Quick |
| 2020/0129563 A1 | 4/2020 | Flower |
| 2020/0150005 A1 | 5/2020 | Slutter et al. |
| 2020/0182757 A1 | 6/2020 | Hamstrom et al. |
| 2020/0208086 A1 | 7/2020 | Quick et al. |
| 2020/0248117 A1 | 8/2020 | Choi et al. |
| 2020/0305418 A1 | 10/2020 | Wu et al. |
| 2020/0315405 A1 | 10/2020 | Fiola |
| 2020/0352578 A1 | 11/2020 | Torrie et al. |
| 2020/0352587 A1 | 11/2020 | Davenport et al. |
| 2020/0354675 A1 | 11/2020 | Vacher et al. |
| 2020/0384690 A1 | 12/2020 | Myers et al. |
| 2021/0085356 A1 | 3/2021 | Knowlton |
| 2021/0102875 A1 | 4/2021 | Levers et al. |
| 2021/0123838 A1 | 4/2021 | Davenport et al. |
| 2021/0139840 A1 | 5/2021 | Khalaj |
| 2021/0140856 A1 | 5/2021 | Reis et al. |
| 2021/0169636 A1 | 6/2021 | Wood et al. |
| 2021/0214673 A1 | 7/2021 | Jovanovich et al. |
| 2021/0330725 A1 | 10/2021 | Leti et al. |
| 2022/0193301 A1 | 6/2022 | Quick et al. |
| 2022/0299409 A1 | 9/2022 | Bruelhart et al. |
| 2022/0333057 A1 | 10/2022 | Tang et al. |
| 2022/0339118 A1 | 10/2022 | Bush et al. |
| 2022/0339202 A1 | 10/2022 | Bush et al. |
| 2022/0339254 A1 | 10/2022 | Bush et al. |
| 2022/0347352 A1 | 11/2022 | Bush et al. |
| 2022/0349873 A1 | 11/2022 | Bush et al. |
| 2024/0050953 A1 | 2/2024 | Mccullough et al. |
| 2024/0207841 A1 | 6/2024 | Doshi et al. |
| 2024/0209299 A1 | 6/2024 | Doshi et al. |
| 2024/0209307 A1 | 6/2024 | Doshi et al. |

FOREIGN PATENT DOCUMENTS

| | | |
|---|---|---|
| CN | 1625398 A | 6/2005 |
| CN | 1878470 A | 12/2006 |
| CN | 101423820 A | 5/2009 |
| CN | 101500512 A | 8/2009 |
| CN | 102089425 A | 6/2011 |
| CN | 102387824 A | 3/2012 |
| CN | 110368498 A | 10/2019 |
| EP | 0350887 A2 | 1/1990 |

(56) References Cited

FOREIGN PATENT DOCUMENTS

| | | |
|---|---|---|
| EP | 0444270 A1 | 9/1991 |
| EP | 0 215 274 B1 | 3/1993 |
| EP | 0 809 976 A2 | 12/1997 |
| EP | 0 751 217 A2 | 5/1999 |
| EP | 0751217 A3 | 5/1999 |
| EP | 1 357 922 A1 | 11/2003 |
| EP | 2 343 079 A2 | 7/2011 |
| EP | 2502986 A1 | 9/2012 |
| EP | 2828378 A1 | 1/2015 |
| EP | 2 367 419 B1 | 2/2016 |
| EP | 3 366 303 A1 | 8/2018 |
| EP | 2 888 353 B1 | 10/2018 |
| EP | 3 156 060 B1 | 11/2019 |
| EP | 3 366 303 B1 | 6/2020 |
| EP | 3 304 030 B1 | 3/2021 |
| ES | 2912075 T3 | 5/2022 |
| GB | 1238401 A | 7/1971 |
| GB | 2106552 | 12/2001 |
| JP | S53-96394 A | 8/1978 |
| JP | S58501817 A | 10/1983 |
| JP | H03-72872 A | 3/1991 |
| JP | 04218147 A | 8/1992 |
| JP | 2002-531176 A | 9/2002 |
| JP | 2002537851 A | 12/2002 |
| JP | 2004529872 A | 9/2004 |
| JP | 2005348666 A | 12/2005 |
| JP | 2008504816 A | 2/2008 |
| JP | 2010524498 A | 7/2010 |
| JP | 2014-193415 A | 10/2014 |
| JP | 20141993415 A | 10/2014 |
| JP | 2015134356 A | 7/2015 |
| WO | WO 83/01384 A1 | 4/1983 |
| WO | WO 90/00739 A1 | 1/1990 |
| WO | WO 95/28409 A1 | 10/1995 |
| WO | WO 97/23602 A1 | 7/1997 |
| WO | WO 98/53850 A2 | 12/1998 |
| WO | WO 98/53850 A3 | 12/1998 |
| WO | WO 98/54295 A1 | 12/1998 |
| WO | WO 98/56897 A1 | 12/1998 |
| WO | WO 99/12555 A1 | 3/1999 |
| WO | WO 99/21963 A1 | 5/1999 |
| WO | WO 99/23199 A1 | 5/1999 |
| WO | WO 00/32207 A1 | 6/2000 |
| WO | WO 00/53797 A1 | 9/2000 |
| WO | WO 01/57082 A2 | 8/2001 |
| WO | WO 02/062358 A1 | 8/2002 |
| WO | WO 02/066598 A1 | 8/2002 |
| WO | WO 03/063870 A1 | 8/2003 |
| WO | WO 2005/034843 A2 | 4/2005 |
| WO | WO 2006/008779 A1 | 1/2006 |
| WO | WO 2006/014156 A1 | 2/2006 |
| WO | WO 2006/014159 A2 | 2/2006 |
| WO | WO 2007/042818 A1 | 4/2007 |
| WO | WO 2007/092801 A2 | 8/2007 |
| WO | WO 2007/092801 A3 | 8/2007 |
| WO | WO 2008/133874 A1 | 11/2008 |
| WO | WO 2009/136173 A2 | 11/2009 |
| WO | WO 2009/136173 A3 | 11/2009 |
| WO | WO 2011/033228 A1 | 3/2011 |
| WO | WO 2012/009958 A1 | 1/2012 |
| WO | WO 2013/019154 A1 | 2/2013 |
| WO | WO 2013/030761 A1 | 3/2013 |
| WO | WO 2013/142254 A1 | 9/2013 |
| WO | WO 2014/069401 A1 | 5/2014 |
| WO | WO 2014/153072 A1 | 9/2014 |
| WO | WO 2019/232504 A2 | 12/2019 |
| WO | WO 2020/230039 A1 | 11/2020 |
| WO | WO 2021/048441 A1 | 3/2021 |
| WO | WO 2022/020080 A1 | 1/2022 |
| WO | WO 2022/231904 A1 | 11/2022 |
| WO | WO 2022/231913 A1 | 11/2022 |
| WO | WO 2024/145258 A1 | 7/2024 |

OTHER PUBLICATIONS

Adams, B.F. et al., "The role of respiratory epithelium in a rat model of obliterative airway disease," Transplantation, Feb. 2000, vol. 69, pp. 661-693.

Aneja, R. et al., "Preconditioning with high mobility group box 1 (HMGB1) induces lipopolysaccharide (LPS) tolerance", J. Leukoc Biol., Nov. 2008, vol. 84, No. 5, pp. 1326-1334.

Anonymous, "Understanding mesh sizes", ESPI Metals, in 4 pages (This refers to a webpage and there is no date apparent in the document; however, the webpage may have been publicly available in some form prior to Apr. 10, 2012—the date this reference was cited by an examiner in a related client U.S. Appl. No. 11/518,012). URL: http://www.espimetals.com/index.php/online-catalog/334-understanding-mesh-sizes.

Anonymous, "Recell patient leaflet", Absolute Makeover, Apr. 21, 2011, http://www.absolutemakeover.com.au/_literature_46887/Recell_Patient_Leaflet.

Anonymous, "Welcome to Clinical Cell Culture", C3 Clinical Cell Culture, archived Dec. 15, 2003, in 2 pages. URL: http://www.clinicalcellculture.com.

Antoni, D. et al., "Development of the Total Care Unit," ANZBA (Queenstown), 1997, in 1 page (Abstract).

Antoni, D. et al., "Three-Dimensional Cell Culture: A Breakthrough in Vivo", Int. J. Mol. Sci., Mar. 2015, vol. 16, pp. 5517-5527. URL: https://doi.org/10.3390/ijms16035517>.

Arno, A. et al., "Stem Cell Therapy: A New Treatment for Burns?", Pharmaceuticals, Oct. 2011, vol. 4, pp. 1355-1380.

Atala, A. et al., "Formation of urothelial structures in vivo from dissociated cells attached to biodegradable polymer scaffolds in vitro,", J Urol, Aug. 1992, vol. 148, pp. 658-662.

Backman, B. et al, "Scientific Visualisation as an Aide to Quantifying the Extent of Burn Injury", ANZBA (Gold Coast), 1995, in 1 page (Abstract).

Barnden, L. et al., "Adult Burn Patients Treated with a Combination of Skin Graft Techniques—What Dressing System to Use?", ANZBA (Gold Coast), 1995, in 1 page (Abstract).

Barnden, L. et al., "Designing a Tool To Facilitate and Standardise Burn Care In W. A.", ANZBA, 1996, in 1 page (Abstract).

Barnden, L. et al., "Dressings Used in the Burn Treated with Cultural Epidermal Autograft", ANZBA (Canberra), 1993, in 1 page (Abstract).

Barrera, A., "The Use of Micrografts and Minigrafts for the Treatment of Burn Alopecia", Plast. and Reconstr. Surg., Feb. 1999, vol. 103(2), pp. 581-584.

Barrientos, S. et al., "Growth factors and cytokines in wound healing", Wound Repair and Regeneration, 2008, vol. 16, pp. 585-601.

Bello, Y. et al., "Tissue-Engineered Skin in Wound Healing", Am J Clin Dermatol, 2001, vol. 2(5), pp. 305-313.

Ben-Porath, I. et al., "When cells get stressed: and integrative view of cellular senescence", The Journal of Clinical Investigation, Jan. 2004, vol. 113(1), pp. 8-13.

Bird, J. et al., "New Techniques of Managing Palmer Burns", ANZBA, May 1994, in 1 page (Abstract).

Blennerhasset, L. et al., "The Use of the Ultrasonic Aspiration as a Tissue Dissector for Excision of Burn Escar", ANZBA, 1996, p. 40 (Abstract).

Bogusiewicz, M. et al., "Local collagen turnover in human foetal membranes during full term vaginal delivery", European Journal of Obstetrics & Gynecology and Reproductive Biology, 1998, vol. 77, Iss. 2, pp. 141-143.

Booth, K. et al., "Scar Assessment for the Future", ANZBA (Canberra), 1993, in 1 page (Abstract).

Boyce, S.T. et al., "Cultivation, frozen storage and clonal growth of normal human epithelial keratinocytes in serum-free media", J. Tissue Cult. Methods, 1985, vol. 9, pp. 83-93.

Brandy, D. , "A New Instrument for the Expedient Production of Minigrafts", J. Dermatol. Surg. Oncol., 1992, vol. 18, pp. 487-492.

Brzoska, M. et al., "Epithelial differentiation of human adipose tissue-derived adult stem cells", Biochemical and Biophysical Research Communications, 2005, vol. 330, pp. 142-150.

Burgeson, R. E. et al., "The dermal-epidermal junction", Curr Op Cell Biol, 1997, vol. 9, pp. 651-658.

(56) References Cited

OTHER PUBLICATIONS

Burnouf, T. et al., "Blood-derived biomaterials and platelet growth factors in regenerative medicine", Blood Reviews, 2013, vol. 27, pp. 77-89.
Butler, C.E. et al., "Comparison of Cultured and Uncultured keratinocytes seeded into a collagen—GAG matrix for skin replacements", British Journal of Plastic Surgery, 1999, vol. 52, pp. 127-132.
Caldow, J. et al., "The Use of Self Adhesive Elastic Bandaging to Control Oedema in the Burn Injured Hand", ANZBA (Gold Coast), 1995, p. 35 (Abstract).
Cena, B. et al., "Computerised Integration of Multimodality Imaging in Scar Assessment", ANZBA (Gold Coast), 1995, p. 20 (Abstract).
Chan, R. et al., "Clonogenicity of human endometrial epithelial and stromal cells", Biol. Reprod., Feb. 2004, vol. 70, No. 6, pp. 1738-1750.
Cheng, C-F. et al., "A fragment of secreted Hsp90α carries properties that enable it to accelerate effectively both acute and diabetic wound healing in mice", The Journal of Clinical Investigation, Nov. 2011, vol. 121, No. 11, pp. 4348-4361.
Compton, C., "Wound Healing Potential of Cultured Epithelium", Wounds, Mar./Apr. 1993, vol. 5(2), pp. 97-111.
Cooper, R. et al., "The Effect of Aprotinin on Human Cultured Epidermal Cells", PAN/Asian European Tissue Repair Society Wound Healing Meeting, 1997, in 1 page (Abstract).
Costin, G.E. et al., "Human skin pigmentation: melanocytes modulate skin color in response to stress", The FASEB Journal, Apr. 2007, vol. 21, pp. 976-994.
Definition of "suspension", Dictionary.com, accessed Feb. 7, 2024, in 4 pages. URL: https://www.dictionary.com/browse/suspension.
Dejong, H. et al., "Pathways in Therapy for Burns Patients", ANZBA (Queenstown), 1997, in 1 page (Abstract).
Deluca, M., et al., "Human Epithelial Cells Induce Human Melanocyte Growth In Vitro but Only Skin Keratinocytes Regulate Its Proper Differentiation in the Absence of Dermis", The Journal of Cell Biology, Nov. 1988, vol. 107, pp. 1919-1926.
Devalia, J. L. et al., "Culture and comparison of human bronchial and nasal epithelial cells in vitro", Resp. Med., 1990, vol. 84, pp. 303-312.
Ding, Y.-L. et al., "Recent Advances in Burn Wound Management in China", Acta Chirurgiae Plasticae, 1989, vol. 31(2), pp. 84-91.
Dzubow, "Scar Revision by Punch-Graft Transplants", J. Dermatol. Surg. Oncol., Dec. 1985, vol. 11(12), pp. 1200-1202.
Early Burn Management Report, PNAZBA, 1997, in 1 page (Abstract).
Edgar, D. et al., "Silicone Oil Revisited", ANZBA (Manly), 1998, PO-18:49, in 1 page (Abstract).
Edgar, D. et al., "Playing in a Team can be a Pain", ANZBA (Tasmania), 1999, p. 65 (Abstract).
Edgar, D. et al., "The Good Oil?", ANZBA (Tasmania), 1999, p. 37 (Abstract).
"Education—The Key to Better Management of the Burn Victim: An education project in Western Australia", Presentation, Rural National Health Meeting, 1995, in 4 pages (Abstract).
Eisinger, M. et al., "Human epidermal cell cultures: Growth and differentiation in the absence of dermal components or medium supplements", PNAS, 1979, vol. 76, pp. 5340-5344.
Elliget, K. et al., "Human Bronchial Epithelial Cell Culture", Specialized Vertebrate Cultures—Respir. Sys., 1992, Module 13B:3, pp. 1-17.
"Epithelium", Wikipedia, accessed Apr. 6, 2023, in 10 pages. URL: https://en.wikipedia.org/wiki/Epithelium.
Falabella, R. et al., "Surgical Combination Therapy for Vitiligo and Piebaldism", Dermatol. Surg., 1995, vol. 21, pp. 852-857.
Falabella, R., "Repigmentation of Leukoderma by Minigrafts of Normally Pigmented, Autologous Skin", J.Dermatol. Sur. Oncol., Dec. 1978, vol. 4, pp. 916-919.
Fong, J. et al., "The Use of Clinical Indicators to Measure a Minimum Standard of Care For Early Burn Management", ANZBA (Queenstown), 1997, in 1 page.
Franklin, W. et al., "Expansion of Bronchial Epithelial Cell Populations by In Vitro Culture of Explants from Dysplastic and Histologically Normal Sites", Am. J. Respir Cell. Mal. Biol., 1996, vol. 15, pp. 297-304.
Fraulin, F.O.G. et al., "Autotransplantation of epithelial cells in the pig via an aerosol vehicle", J Burn Care Rehabil, 1998, vol. 19, pp. 337-345.
Freitas, Jr., "Nanomedicine, vol. I: Basic Capabilities", 1999 (last updated Feb. 20, 2003), Landes Bioscience, Georgetown, TX, in 18 pages (only the Summary, Table of Contents and section 8.5.1 Cytometrics of this book are submitted for this reference). URL: https://www.nanomedicine.com/NMI.htm.
Fulda, S. et al. "Cellular Stress Responses: Cell Survival and Cell Death", International Journal of Cell Biology, 2010, Article ID No. 214074, pp. 1-23.
Gallico, III, G. et al., "Permanent Coverage of large Burn Wounds with Autologous Cultured Human Epithelium", The New England Journal of Medicine, Aug. 16, 1984, vol. 311, No. 7, pp. 448-451.
Gauthier, Y. et al., "Autologous grafting with noncultured melanocytes: A simplified method for treatment of depigmented lesions", Journal of the American Academy of Dermatol, 1992, vol. 26, No. 1, Part 1, 1992, pp. 191-194.
Giele, H. et al., "An alternative technique for the harvesting of cultured epithelial cell sheets", Meth. Cell Sci., 1995, vol. 17, pp. 233-236.
Giele, H. et al., "Anatomical Variations in Pressures Generated by Pressure Garments", Plast. Reconstruct. Surg., Feb. 1998, vol. 101, vol. 2, pp. 399-406.
Giele, H. P. et al., "Direct measurement of cutaneous pressures generated by pressure garments", Burns, 1997, vol. 23(2), pp. 137-141.
Giele, H. P. et al., "Early Use of Pressure Masks to Avoid Facial Contracture During the Pregrafting Phase", J. Burn Care Rehabil., Nov./Dec. 1995, vol. 16, pp. 641-645.
Giele, H. P. et al., "Management of full thickness burns to lactating breasts", Burns, 1994, vol. 20(3), pp. 278-280.
Gospodarowicz. D. et al., "The Role of Growth Factors and Extracellular Matrices in the Control of Mammalian Cell Proliferation", The Biology of Normal Human Growth (M. Ritzen et al., ed), 1991, Raven Press, pp. 1-19.
Goulet, F. et al., "Morphologic and Functional Properties of Bronchial Cells Isolated from Normal and Asthmatic Subjects", Am. J. Respir. Cell. Mal. Biol., 1996, vol. 15, pp. 312-318.
Gramlich, G., "ReCell ein Erfahrungsbericht," Internet article, Online, Apr. 21, 2011, http://www.hagenmuehle.de/documents/MicrosoftWord-RecellVeroffentlichungInternet_000.pdf.
Griffiths, T. et al., "The Influence of Geography on Burn Outcome", ANZBA, 1994, in 3 pages (Abstract).
Griffiths, T. et al., "The Use of Epidermal Derived Factors to Influence Wound Healing", ANZBA (Gold Coast), 1995, p. 11 (Abstract).
Griffiths, T. et al., "Itch", ANZBA (Queenstown), 1997, in 1 page (Abstract).
Guedon, I. et al., "Culture and cytogenetic studies of adult human keratinocytes using a new growth factor", Differentiation, 1981, vol. 19, No. 2, pp. 109-114.
Habberfield, S. et al., "Burn Unit Support Groups—A Burning Issue", ANZBA (Canberra), 1993, p. 46 (Abstract).
Haberfeld, S. et al., "Psychological Aspects of Burn Injury: Research Issues", ANZBA (Gold Coast), 1995, p. 67 (Abstract).
Haberfeld, S. et al., "Psychological Reactions to Trauma: A Survey of Burns Unit Staff", ANZBA, 1996, p. 42 (Abstract).
Harvey, S., "Chapter 42: Blood, fluids, electrolytes, and hematologic drugs", in *Remington's Pharmaceutical Sciences*, 17th ed., 1985, Gennaro, A. et al., ed., Mack Publishing Company: Easton, PA, pp. 816-842.
Hentzer, B et al., "Suction Blister Transplantation for Leg Ulcers", Acta Dermatovener (Stockholm), 1975, vol. 55, pp. 207-209.
Hicks, W. et al., "Isolation and characterization of basal cells from human upper respiratory epithelium", Experimental Cell Research, 1997, vol. 237, pp. 357-363.

(56) References Cited

OTHER PUBLICATIONS

Hirobe, T., "Selective growth and serial passage of mouse melanocytes from neonatal epidermis in a medium supplemented with bovine pituitary extract", J. Exp. Zool., 1991, vol. 257, pp. 184-194.

Hirobe, T., "Melanocyte stimulating hormone induces the differentiation of mouse epidermal melanocytes in serum-free culture", J. Cell. Phys., Aug. 1992, vol. 152, No. 2, pp. 337-345.

Holmes et al., "A Comparative Study of the ReCell Device and Autologous Split-Thickness Meshed Skin Graft in the Treatment of Acute Burn Injuries", Journal of Burn Care & Research, Sep./Oct. 2018, vol. 39, No. 5, pp. 694-702.

Hornum, A. et al., "Tragic Tales—Paediatric Burns in Motor Vehicles", ANZBA, 1996, in 1 page (Abstract).

Hornum, A. et al., "Use of Retention Dressings in the Paediatric Population for Partial Thickness Burn Injury", ANZBA, May 1994, in 1 page (Abstract).

Hornum, A. et al., "The Impact of Integra™ Dermal Template Reconstruction on Paediatric Burn Care", ANZBA, 1999, p. 82 (Abstract).

Hornum, A. et al., "The Post Operative Management of Paediatric Burns Patients Treated with Cultured Epithelial Autograft in Fluid Suspension", ANZBA (Gold Coast), 1995, p. 18 (Abstract).

Humphrey, S., "Burns Education in Intensive Care", ANZBA, 1998, PO-19, p. 49 (Abstract).

Hunyadi, J. et al., "Keratinocyte grafting: Covering of skin defects by separated autologous keratinocytes in a fibrin net," The Journal of Investigative Dermatology, 1987, vol. 89, pp. 119-120.

Inayama, Y. et al., "In Vitro and In Vivo Growth and Differentiation of Clones of Tracheal Basal Cells", Am. J. Pathol., Mar. 1989, vol. 134(3), pp. 539-549.

Inayama, Y. et al., "The Differentiation Potential of Tracheal Basal Cells", Lab. Invest., 1988, vol. 58(6), pp. 706-717.

Ito, Y. et al., "Stability of Frozen Serum Levels of Insulin-like Growth Factor-I, Insulin-like Growth Factor-II, Insulin-like Growth Factor Binding Protein-3, Transforming Growth Factor β, Soluble Fas, and Superoxide Dismutase Activity for the JACC", Journal of Epidemiology, Mar. 2005, vol. 15, pp. S67-S73.

Jackson, W M. et al., "Concise Review: Clinical Translation of Wound Healing Therapies Based on Mesenchymal Stem Cells," Stem Cells Translational Medicine, 2012 (first published online Dec. 7, 2011), vol. 1, pp. 44-50.

Jensen, P. et al., "Cultivation at Low Temperature as a Measure to Prevent Contamination with Fibroblasts in Epithelial Cultures from Human Skin," The Journal of Investigative Dermatology, 1981, vol. 77, No. 2, pp. 210-212.

Jones, R. T. et al., "Method for the Culture of Human Bronchial Epithelial Cells from Tissues Obtained at Extended Postmortem Intervals", Annual Meeting Abstracts, Mar. 1987, Abstract/Section 99, in 1 page.

Ke, Y. et al., "Cell Density Governs the Ability of Human Bronchial Epithelial Cells to Recognize Serum and Transforming Growth Factor Beta-1 as Squamous Differentiation-inducing Agents", Am. J. Pathol., Oct. 1990, vol. 137(4), pp. 833-843.

Kisker-Biotech dry block heat and water baths product catalog, printed May 3, 2002, in 3 pages.

Kopecek, J., "Hydrogel Biomaterials: A Smart Future?", Biomaterials, Dec. 2007, vol. 28(34), pp. 5185-5192. URL: https://www.ncbi.nlm.nih.gov/pmc/articles/PMC2212614/.

Lechner, J. et al., "Chapter 1: In Vitro Human Bronchial Epithelial Model Systems for Carcinogenesis Studies", In Vitro Models for Cancer Research, 1985, vol. VI, pp. 3-17.

Lechner, J. et al., "Clonal Growth of Normal Adult Human Bronchial Epithelial Cells in a Serum-Free Medium", In Vitro, Jul. 1982, vol. 18(7), pp. 633-642.

Lechner, J. et al., "Induction of squamous differentiation of normal human bronchial epithelial cells by small amounts of serum", Differentiation, 1984, vol. 25, pp. 229-237.

Lee, M. et al., "Management of Inhalation Injury", ANZBA (Manly), 1998, 0-34, p. 39 (Abstract).

Lee, S.-S. et al., "An easy method for preparation of postage stamp autografts", Burns, 2000, vol. 26, pp. 741-749.

Liddiard, K. et al., "Pressure Management of the Cultured Epithelial Autograft", ANZBA (Canberra), 1993, p. 38 (Abstract).

Liddiard, K. et al., "Scar management of the Cultured Epithelial Autograft", ANZBA (Gold Coast), 1995, p. 37 (Abstract).

Liddiard, K. et al., "The Direct Measurement of Cutaneous Pressure Generated by Pressure Garments", International Symposium on Hypertrophic Scars (Hong Kong), 1995, p. 36 (Abstract).

Lin, S-D. et al., "Allogeneic micros kin grafting of rabbits' skin wounds", Burns, vol. 1993, vol. 19(3), pp. 208-214.

Lin, S-D. et al., "Microskin grafting of rabbit skin wounds with Biobrane overlay", Burns, 1992, vol. 8(5), pp. 390-394.

Lindquist, S. et al., "The Heat-Shock Proteins", Annu. Rev. Genet., 1988, vol. 22, pp. 631-677.

Ling, Hyaluronan, Section II, Soft Tissue Repair by HA and HA Derivatives, Chapter XI. Postoperative Adhesion Prevention and Soft Tissue Repair by Hyaluronan, Hyaluronic Acid, Beijing, The China Light Industry Press, 2000, pp. 222-227.

Liu, X. et al., "A Biofabricated Vascularized Skin Model of Atopic Dermatitis for Preclinical Studies", Biofabrication, published online Apr. 9, 2020, vol. 12(3), pp. 1-24.

Lucas, M., "Mini- and Micrografts Exclusively versus Standard Grafts Mixed with Mini- and Micrografts", 1993, p. 388.

MacDiarmid et al., "Separation of Epidermal Tissue from Underlying Dermis and Primary Keratinocyte Culture", Methods in Molecular Biology, vol. 174, 2001, pp. 401-410.

Magnusson, M. et al., "Epidemiological Differences of Burn Injuries in Aboriginal and Nonaboriginal Children", ANZBA (Tasmania), 1999, p. 77 (Abstract).

Magnusson, M. et al., "The Effect of Skin Graft Storage on Keratinocytes", ANZBA (Manly), 1998, 0-33, p. 39, in 1 page (Abstract).

Magnusson, M. et al., "The Proliferative Capacity of Keratinocytes Isolated from Skin Stored After Meshing vs Non-Meshed", International Symposium on Hypertrophic Scars (Hong Kong), 1999. p. 51.

Magnusson, M. et al., "Transepidermal Water Loss as a Quantitative Method for Evaluating Epithelialisation", ANZBA (Tasmania), 1999, p. 31 (Abstract).

Magnusson, M. et al., "Transepidermal Water Loss as a Quantitative Method for Evaluating Epithelialisation", Princess Margaret Hospital for Children Res. Advances Seminar, 1999, p. 50.

Majid, I., "Grafting in vitiligo: How to get better results and how to avoid complications", Journal of Cutaneous and Aesthetic Surgery, Apr.-Jun. 2013, vol. 6.2, pp. 83-89.

Mansilla, E. et al., "Outstanding survival and regeneration process by the use of intelligent acellular dermal matrices and mesenchymal stem cells in a burn pig model", Transplantation Proceedings, 2010, vol. 42, pp. 4275-4278.

Mardovin, W. et al., "Micrografts: The "Super" Expansion Graft", J. Burn Care Rehabil., 1992, vol. 13, pp. 556-559.

May, A. L. et al., "Assessment of adhesion assays for use with keratinocytes", Exp. Dermatol., 2001, vol. 10(1), pp. 62-69.

Mayshar, Y. et al., "Fibroblast growth factor 4 and its novel splice isoform have opposing effects on the maintenance of human embryonic stem cell self-renewal", Stem Cells, Jan. 2008, vol. 26, No. 3, pp. 767-774.

Merriam-Webster Online Medical Dictionary, Definition of "suspension", accessed Sep. 2, 2008, in 1 page. URL: http://www2.merriamwebster.com/cgi- bin/mwmednlm?book=Medical&va=suspension.

Merriam-Webster's College Dictionary, Random House, 1991, p. 997.

Mesenchymal Stem Cell—Wikipedia, the free encyclopedia, downloaded Sep. 30, 2016, 9 total pages.

Milara, J. et al., "The JAK2 pathway is activated in idiopathic pulmonary fibrosis", Respiratory Research, 2018, vol. 19 No. 24, pp. 1-12.

Millipore (primary mesenchymal; pp. 1-2; downloaded on Oct. 3, 2016.

(56) References Cited

OTHER PUBLICATIONS

Mulekar, S. et al., "Treatment of vitiligo lesions by ReCell vs. conventional melanocyte-keratinocyte transplantation: a pilot study", The British Journal of Dermatology, Jan. 1, 2008, vol. 158(1), pp. 45-49.

Mizuno, H. et al., "Concise Review: Adipose-Derived Stem Cells as a Novel Tool for Future Regenerative Medicine", Stem Cells, Mar. 2012, vol. 30, pp. 804-810.

Navarro, F. A, et al., "Sprayed keratinocyte suspensions accelerate epidermal coverage in a porcine microwound model", J. Burn Care Rehabil., 2000, vol. 21, pp. 513-518.

Nielson, J. et al., "Case Presentation", ANZBA, 2000, p. 71 (Abstract).

Nickoloff, B. et al., "Further characterization of the keratinocyte somatomedin-C/insulin-like growth factor I receptor and the biological responsiveness of cultured keratinocytes to SM-C/IGF-I", Dermatologica, 1988, vol. 177, No. 5, pp. 265-273.

Noel-Hudson, M. S. et al: "Human epidermis reconstructed on synthetic membrane: influence of experimental conditions on terminal differentiation", In Vitro Cell. Dev. Biol., Jul./Aug. 1995, vol. 31, No. 7, pp. 508-515.

Notarnicola, A. et al., "Effect of Shock Wave Treatment on Platelet-Rich Plasma Added to Osteoblast Cultures", Ultrasound in Med. & Biol., Jan. 2011, vol. 37, No. 1, pp. 160-168.

Okuda, K. et al., "Platelet-Rich Plasma Contains High Levels of Platelet-Derived Growth Factor and Transforming Growth Factor-β and Modulates the Proliferation of Periodontally Related Calls in Vitro", J. Periodontal., Jun. 2003, vol. 74, No. 6, pp. 849-857.

Olsson, M. J. et al, "Leucoderma treated by transplantation of a basal cell layer enriched suspension", British Journal of Dermatology, 1998, vol. 138, pp. 644-648.

Osborne, C. S. et al., "Investigation into the biological stability of collagen/chondroitin-6-sulphate gels and their contraction by fibroblasts and keratinocytes: the effect of crosslinking agents and diamines", Biomaterials, Feb. 1999, vol. 20, No. 3, pp. 283-290.

Papini, R. et al., "Current concepts in the management of burns with inhalation injury", Care Crit. III., 1999, vol. 15(2), pp. 61-66.

Papini, R. et al., "Fluid Resuscitation Tissue Perfusion and Wound Salvage", ANZBA, 1998, 0-30, pp. 37 (Abstract).

Papini, R. et al., "Rapid Epithelial Cell Autograft", ANZBA (Manly), 1998, 0-31, p. 38 (Abstract).

Perrott, E. et al., "Heel Pain—Repercussions for Functional Outcome in Major Burns", ANZBA (Manly), 1998, 0-29, p. 37 (Abstract).

Petersen, M. et al., "Enhanced synthesis of collagenase by human keratinocytes cultures on type I or type IV collagen", J. of Investigative Dermatology, Mar. 1990, vol. 94, No. 3, pp. 341-346.

Product No. 352070 of BD e-Catalog: Centrifuges and test tubes, printed May 3, 2002, in 3 pages.

Product No. 352360 of BD e-Catalog: Centrifuges and test tubes, printed May 3, 2002, in 2 pages.

Pye, R. J., "Cultured Keratinocytes as Biological Wound Dressings", Eye, 1998, pp. 174-177 (abstract only).

Mareengroup, "ReCell procedure in Marseille", YouTube, video published Jun. 26, 2010 (retrieved on May 6, 2023), in 1 page. URL: https://www.youtube.com/watch?v=c-DgW82bWTk.

Regnier, M. et al., "Integration of Langerhans cells into a pigmented reconstructed human epidermis", J. Invest. Dermatol., Oct. 1997, vol. 109, No. 4, pp. 510-512.

Reynolds, E., "The boy with spray-on skin: Two-year-old horrifically scalded by split cup of tea makes amazing recovery after pioneering surgery", DailyMail, Feb. 17, 2012, in 9 pages. URL: https://www.dailymail.co.uk/health/article-2102612/The-boy-spray-skin-Two-year-old-burned-cup-tea-makes-recovery-pioneering-surgery.html.

Robinson, C., "Culture of Conducting Airway Epithelial Cells in Serum-Free Medium", Tiss. Cult. Meth., 1991, vol. 13, pp. 95-102.

Salgado, M. et al., "Comparison between conducted healing and the use of skin grafts for the treatment of skin wounds in rabbits", Journal of Medicine and Life, Jul.-Sep. 2008, vol. 1, No. 3, pp. 269-274.

Savandra, J. et al., "The Influence of Surgery on the Genetic Predisposition to Form Hypertrophic Scars in the Paediatric Scald Population", ANZBA (Manly), 1998, 0-32, p. 38 (Abstract).

Shimizu, T. et al., "Expression of "Cell-type-specific" Markers during Rat Tracheal Epithelial Regeneration", Am. J. Respir. Cell Mal. Biol., 1992, vol. 7, pp. 30-41.

Shirakata, Y. et al., "Heparin-binging EGF-like growth factor accelerates keratinocyte migration and skin wound healing", J. Cell. Sci., 2005, vol. 118, No. 11, pp. 2363-2370.

Shore, J.W. et al., "Results of buccal mucosal grafting for patients with medically controlled ocular cicatricial pemphigoid", Ophthalmology, 1992, vol. 99, pp. 383-395.

Silla, R. et al., "'Milton Solution:' Does it have a place in burn treatment?", ANZBA, 2000, p. 52 (Abstract).

Simman, R. et al., "Use of Hyaluronic Acid-Based Biological Bilaminar Matrix in Wound Bed Preparation: A Case Series", ePlasty, Feb. 22, 2018, vol. 18, pp. 151-161.

Skinner, A. et al., "A Possible Alternative to Custom made Pressure Garments for Scar Manipulation", ANZBA, May 1994, in 1 page (Abstract).

Skinner, A. et al., "The Clinical Use of Hydrophobic Fabric Garments in the Paediatric Population", ANZBA, 1996, p. 34 (Abstract).

Skinner, A. et al., "Sunburn—An Unnecessary Cause of Pain", ANZBA (Queenstown), 1997, in 1 page (Abstract).

Skinner, A. et al., "The Comparison of Pressure Garment Implementation & Removal from 1991-1994", ANZBA (Gold Coast), 1995, p. 36 (Abstract).

Skouge, J. W., "Techniques for Split-Thickness Skin Grafting", J. Dermatol. Surg. Oncol., Aug. 1987, vol. 13(8), pp. 841-849.

Smith, M. et al., "Heterotopic Ossification in Burns: Conservative and Surgical Management", ANZBA (Canberra), 1993, p. 20 (Abstract).

Smithwick, S. et al., "Have Changes in Attitude to the Use of Blood Products Impacted Upon Their Use with the Treatment of A Patient with Major Burn Injury", ANZBA (Queenstown), 1997, in 1 page (Abstract).

Smithwick, S. et al., "Self Harm", ANZBA (Perth), 2000, in 1 page (Abstract).

Smithwick, S. et al., "The Impact of Major Orthopaedic Injuries on Burn Nursing Care", ANZBA (Gold Coast), 1995, p. 33 (Abstract).

Smithwick, S. et al., "The impact of religious belief on the management of the burn injury", Presentation, 1994, in 3 pages.

Smithwick, S. et al., "Stress Management in the Burn Unit", ANZBA (Canberra), 1993, p. 27 (Abstract).

Solotoff, S., "Treatment for Pitted Acne Scarring—Postauricular Punch Grafts followed by Dermabrasion", J. Dermatol. Surg. Oncol., Oct. 1986, vol. 12(10), pp. 1079-1084.

Sperring, B. et al., "Continuing to Care—Burn Management in the Outpatient Setting", ANZBA, 1996, p. 29 (Abstract).

Stoner, M. et al., "Cultured Epithelial Auto graft Made Quick and Easy 1) Laboratory", ANZBA, 1996, p. 41 (Abstract).

Stoner, M. et al., "Systemic factors influencing the growth of cultured epithelial autograft", Burns, 1996, vol. 22(3), pp. 197-199.

Stoner, M. et al., "The Treatment of Hypopigmentation with Cultured Epithelial Cell", ANZBA (Gold Coast), 1995, p. 32 (Abstract).

Stoner, M. et al., "Treatment of Burns to the Sole of the Foot with Site Specific Cultured Epithelial Autograft", ANZBA (Gold Coast), 1995, p. 17 (Abstract).

Stoner, M. et al., "Treatment of Burns to the Sole of the Foot with Site Specific Cultured Epithelial Autograft", Presentation at The International Symposium on Hypertrophic Scars (Hong Kong), 1995, p. 14 (Abstract).

Stoner, M. et al., "Treatment of burns to the sole of the foot with site specific cultured epithelial autograft", Presentation at The International Symposium on Hypertrophic Scar (Hong Kong) pp. 1-7 (1995) (Abstract).

Stoner, M. et al., "When It Absolutely, Positively Has To Be There!—The Logistics of Long Distance Transport of Cultured Epithelial Autograft", ANZBA (Tasmania), 1999, p. 64 (Abstract).

Stoner, M. et al., "Why Use Cultured Epithelial Autograft as a Suspension?", ANZBA, 1998, 0-39, p. 41 (Abstract).

Stoner, M. et al., "'Take' of Cultured Epithelial Auto graft Confirmed by the Presence of Cytokeratin 9", The Surgical Res. Soc. Australasia Ann. Sci. Meeting (Fremantle), 1997, in 1 page (Abstract).

(56) References Cited

OTHER PUBLICATIONS

Stoner, M. et al., "Cultured Airway Epithelium for the Treatment of Tracheal Burns", PAN/Asian European Tissue Repair Society Wound Healing Meeting, 1997, in 1 page (Abstract).
Stoner, M. et al., "The Development of a Unique Technique of Cultured Epithelial Autograft Application", ANZBA (Queenstown), 1997, in 1 page (Abstract).
Stoner, M. et al., "The Development of a Unique Technique of Cultured Epithelial Autograft Application", The Surgical Res. Soc. Australasia Ann. Sci. Meeting (Fremantle), 1997, in 1 page (Abstract).
Stoner, M. et al., "The Treatment of Hypopigmented Lesions with Cultured Epithelial Autograft", J. Burn Care Rehabil. 2000, vol. 21(1), pp. 50-54.
Stoner, M. et al., "The Use of Epithelial Cell Suspension with Meshed Split-Thickness Autograft Using Un-Cultured Keratinocytes in a Pig Model", ANZBA (Tasmania), 1999, p. 63 (Abstract).
Straino, S. et al., "High-Mobility Group Box 1 Protein in Human and Murine Skin: Involvement in Wound Healing", Journal of Investigative Dermatology, 2008, vol. 128, pp. 1545-1553.
Suri, S. et al., "Photopatterned collagen-hyaluronic acid interpenetrating polymer network hydrogels", Acta Biomaterialia, May 2009, vol. 5, pp. 2385-2397.
Svensjo, T. et al., "Autologous keratinocyte suspensions accelerate epidermal wound healing in pigs", J. Surgical Res., 2001, vol. 99, pp. 211-221.
Tamai, K. et al., "PDGFRα-positive cells in bone marrow are mobilized by high mobility group box 1 (HMGB1) to regulate injured epithelia", PNAS, Apr. 2011, vol. 108(16), pp. 6609-6614.
Tan, C. et al., "The Management of Paediatric Palm Burn Injuries", ANZBA, 1996, p. 65 (Abstract).
Teepe, R. G. C. et al., "Fresh versus cryopreserved cultured allografts for the treatment of chronic skin ulcers", Brit. J. Dermatol., 1990, vol. 122, pp. 81-89.
"The current uses of cultured epidermis in Perth and its possible future", Royal Australasian College of Surgeons, Scientific Meeting, Aug. 7, 1992, in 4 pages (Abstract).
Tkáčová, J. et al., "Heat Shock Proteins (HSPs): a Review", Scientific Papers: Animal Science and Biotechnologies, 2012, vol. 45 (1), pp. 349-353.
Van Geel, N. et al., "A Review on Non-Cultured Epidermal Cellular Grafting in Vitiligo", Journal of Cutaneous and Aesthetic Surgery, Jan.-Apr. 2011, vol. 24(1), pp. 17-22.
Vetivex Hartmann's Solution for Injection (3000 mL), California Pet Pharmacy, downloaded Oct. 18, 2023, in 2 pages.
Vollberg, T. M. et al., "Identification of Multiple Stages in the Program of Squamous Differentiation in Tracheobrochial Epithelial Cells", 1984, in 7 pages.
Wang, W. et al, "Histological changes in human skin 32 days after death and the potential forensic significance", Scientific Reports (Nature Publisher Group), 2020, vol. 10(1), in 7 pages.
Watt, F. et al., "Cell-Extracellular Matrix Interactions in Normal and Diseased Skin", Cold Spring Harb Perspect Biol., Apr. 2011, vol. 3(4), in 15 pages. doi: 10.1101/cshperspect.a005124.
Wenkel, H. et al., "Long term results after autologous nasal mucosal transplantation in severe mucus deficiency syndromes", British Journal of Ophthalmology, 2000, vol. 84, pp. 279-284.
Wheeland, R. G., "The Technique and Current Status of Pinch Grafting", J. Dermatol. Surg. Oncol., Aug. 1987, vol. 13(8), pp. 873-880.
White, S. A. et al., "Is Hartmann's the solution?", Anaesthesia, 1997, vol. 52, pp. 422-427.
Williams, P., "Intensive Care Burns—An Experience", ANZBA, 1998, PL-5, p. 23 (Abstract).
Wood, F. et al., "Advances in Burn Care Over 30 Years at Royal Perth Hospital", ANZBA, 1996, p. 70 (Abstract).
Wood, F. M. et al., "Implication of basement membrane development on the underlying scar in partial thickness burn injury", Burns, 1996, vol. 22(6), pp. 459-462.
Wood, F. M. et al., "The Clinical Use of Integra for Dermal Reconstruction", Tissue Engineering Meeting (Orlando), 1999, in 1 page (Abstract).
Wood, F. M. et al., "The Implication of Basic Membrane Development on the Underlying Scar in Partial Thickness Burn Injury", International Symposium on Hypertrophic Scars (Hong Kong), 1995, p. 28 (Abstract).
Wood, F. M. et al., "The Use of Cultured Epithelial Autograft in Paediatric Burn Management", European Club for Paediatric Burns, Scientific Sessions (Zurich), 1996, in 1 page (Abstract).
Wood, F. M. et al., "Western Australian Skin Culture Unit—A 5 Year Review", Tissue Engineering Meeting (Orlando), 1999, in 1 page (Abstract).
Wood, F. et al., "Augmented Clinical Assessment of Burn Injuries: Do You Believe What You See?", ANZBA (Queenstown), 1997, in 1 page (Abstract).
Wood, F. M. et al., "Current difficulties and the possible future directions in scar assessment", Burns, 1996, vol. 22(6), pp. 455-458.
Wood, F. et al., "Scar management of cultured epithelial autograft", Burns, 1996, vol. 22, No. 6, pp. 451-454.
Wood, F. et al., "Scar Management of the Cultured Epithelial Autograft", International Symposium on Hypertrophic Scars (Hong Kong), 1995, p. 19 (Abstract).
Wood, F. et al., "The Current Difficulties and the possible future direction in scar assessment", International Symposium on Hypertrophic Scars (Hong Kong), 1995, p. 20 (Abstract).
Wood, F. et al., "The Role of Integra Dermal Template in Scar Reconstruction Post Burn Injury", ANZBA (Tasmania), 1999, p. 79 (Abstract).
Wood, F. et al., "Wound Bed Preparation with Dermal Preservation", ANZBA, 1996, in 1 page (Abstract).
Wood, F. M., "Advances in the use of cultured skin in wound care", Second Australian Wound Management Association, 1998, in 1 page (Abstract).
Wood, F., "Clinical Indications for the Use of Integra", ANZBA, 1997, in 1 page (Abstract).
Wood, F. M., "Dermal reconstruction in the repair of full thickness skin loss", The Second Australian Wound Management Association Conference (Queensland), 1998, in 1 page (Abstract).
Wood, F., "Dermal Replacement for Use with Cultured Epidermal Autograft", ANZBA (Canberra), 1993, p. 36 (Abstract).
Wood, F., "Early Burn Excision", Oral Presentation, Indonesian Surgeons Association Congress, Jul. 1996, pp. 1-4 (Abstract).
Wood, F., "Experience of the First Two Years of the Skin Culture Laboratory in Western Australia", ANZBA (Gold Coast), 1995, p. 10 (Abstract).
Wood, F., "Facial Burn Management", ANZBA (Queenstown), 1997, in 1 page (Abstract).
Wood, F., "Facial Burn Management", PAN/Asian European Tissue Repair Society Wound Healing Meeting, 1997, in 1 page (Abstract).
Wood, F., "Integra 12 Months On", ANZBA (Manly), 1998, 0-38, in 1 page (Abstract).
Wood, F. M., "Long distance wound care", Second Australian Wound Management Association, 1998, in 1 page (Abstract).
Wood, F., "Major Burns Disaster Plan", ANZBA (Tasmania), 1999, p. 66 (Abstract).
Wood, F. M., "Quality assurance in burn patient care: the James Laing Memorial Essay, 1994", Burns, 1995, vol. 21(8), pp. 563-568.
Wood, F., "Skin Grafting to Achieve Minimal Scarring", ANZBA (Canberra), 1993, p. 40 (Abstract).
Wood, F. et al., "Tailored Wound Healing", ANZBA (Tasmania), 1999, p. 30 (Abstract).
Wood, F., "Teamwork", ANZBA (Manly), 1998, PL-6, p. 23 (Abstract).
Wood, F., "The Clinical Indications For the Use of Cultured Epithelial Autografts", Oral Presentation at the Indonesian Surgeons Association Congress, Jul. 1996, pp. 1-4 (Abstract).
Wood, F., "The Ethics of Burn Care", ANZBA (Manly), 1998, 0-36-38:40, in 1 page (Abstract).
Wood, F. M., "The First Four Years of the Skin Culture Laboratory in W.A", The Surgical Res. Soc. Australasia Ann. Sci. Meeting (Fremantle), 1997, in 1 page (Abstract).

(56) References Cited

OTHER PUBLICATIONS

Wood, F. M. et al., "The Use of Tissue Culture Techniques for the Treatment of the Partial Thickness Burn Injury", Primary Intent. (Australia), Nov. 1993, vol. 1(1), pp. 16-17.

Wright, J. et al., "The Use of Intranasal Fentanyl PCA for Pain Control During Burn Wound Dressing Change", ANZBA, 1996, p. 60 (Abstract).

Wu, F. et al., "Cultured Epithelial Autograft Made Quick and Easy 2) Surgery", ANZBA, 1996, p. 42 (Abstract).

Wu, R. et al., "Growth and differentiation of human nasal epithelial cells in culture. Serum-free, hormone-supplemented medium and proteoglycan synthesis", Am. Rev. Resp. Dis., 1985, vol. 132(2) pp. 311-320 (Abstract).

Wu Xi Qing Gong Da Xue Tian Jin Qing, *Food Analysis*, Wuxi University of Light Industry Beijing: China Light Industry Press, Jun. 2008, ISBN: 978-7-5019-0565-2, pp. 128-129.

Wu, Y. et al., "Mesenchymal Stem Cells Enhance Wound Healing Through Differentiation and Angiogenesis", Stem Cells, Jul. 2007, vol. 25, pp. 2648-2659.

Wyle, L. et al., "Sensation Following Integra Dermal Replacement of Full Thickness Burns", ANZBA (Tasmania), 1999, p. 83 (Abstract).

Young, A. et al., "Human Melanocytes and Keratinocytes Exposed to UVB or UVA In Vivo Show Comparable Levels of Thymine Dimers", The Journal of Investigative Dermatology, vol. 11, No. 6, Dec. 1998, pp. 936-940.

Zhang, M.-L. et al., "Microskin Grafting in the Treatment of Extensive Burns: A Preliminary Report", J. Trauma, 1988, vol. 28(6), pp. 804-807.

Zhang, M.-L. et al., "Microskin grafting. I. Animal experiments", Burns, 1986, vol. 12(8), pp. 540-543.

Zhang, M.-L. et al., "Microskin grafting. II. Clinical report", Burns, 1986, vol. 12(8), pp. 544-548.

International Search Report and Written Opinion mailed May 6, 2024, for PCT Application No. PCT/US2023/085844, 17 pages.

\* cited by examiner

TISSUE HEALING

RELATED APPLICATIONS

This application claims priority to U.S. Provisional Patent Application No. 63/435,446, filed Dec. 27, 2022 and U.S. Provisional Patent Application No. 63/533,586, filed Aug. 18, 2023, both of which are hereby incorporated by reference in their entireties.

TECHNICAL FIELD

The present invention generally relates to the field of regenerative medicine.

BACKGROUND

Within the field of regenerative medicine, it is generally known that manually-prepared regenerative epidermal suspensions, such as are generally disclosed in U.S. Pat. No. 9,029,140 and U.S. patent application Ser. No. 17/690,941, both of which disclosures are hereby incorporated by reference herein in their entirety, aid in tissue repair. While the exact and full pathways that are assisted or enhanced by such suspensions are not completely known, the beneficial effects of regenerative epidermal suspensions on such pathways are well-documented. It is also well-documented that the process of producing regenerative epidermal suspension by hand and without the aid of automation can be arduous and leaves open the possibility for user error and variability.

Other disclosures, such as U.S. Pat. Nos. 11,124,752, 8,162,247, 10,801,001, 8,286,899, and even 10,857,544, disclose related efforts to automate tissue processing and regenerative epidermal suspension production. Each of these disclosures has merit, but none fully solve the problem of how to both automate and improve the production of regenerative epidermal suspensions.

It is clear therefore that on the one hand, regenerative epidermal suspensions and suspensions containing cellular-derived biomolecules are critical elements in tissue regeneration, while on the other hand it is equally evident that the current state of automation in the art is in need of improvement.

Accordingly, there exists a need for improved systems for the automated preparation of regenerative epidermal suspensions and related methods of use.

SUMMARY

From a first aspect, there is provided, a system for automated preparation of a regenerative epidermal suspension may comprise a base unit, a cartridge, and a pestle. In some embodiments, the system may further comprise an accompanying set of tools.

In some embodiments, the base unit may comprise (a) a housing comprising a tissue processing area and a heating element; (b) a cartridge, comprising (i) a cartridge top cover having an upper cartridge surface, (ii) a well plate situated under the cartridge top cover, wherein the at least one well plate comprises at least one well, (iii) a mortar cup (or cup), (iv) a raised processing opening disposed on the upper cartridge surface, wherein the raised processing opening is configured to receive the mortar cup (or cup), and (v) a mortar screen (or screen) transversely disposed within the mortar cup (or cup); and (c) a pestle comprising a pestle head having at least one disaggregation side.

In some embodiments, a system for automated preparation of a regenerative epidermal suspension may comprise a base unit. In some embodiments, the base unit may comprise a housing having an upper housing section, a middle housing section, and a lower housing section. The tissue processing area may be dispensed between a lower surface of the upper housing section, a front side of the middle housing section, and an upper side of the lower housing section.

In some embodiments, a cover may be rotatedly connected to the upper housing section, wherein the cover may be configured to close over the tissue processing area. At least one upper motor may be situated within the upper housing section. A power supply may be coupled to the upper motor.

The base unit may further comprise a pestle shaft (or shaft). The upper motor may be configured at least to actuate the pestle shaft (or shaft), wherein the pestle shaft (or shaft) may extend into the tissue processing area. At least one lower motor may be situated within the lower housing section, wherein the at least one lower motor may be configured to rotate a well plate. A heating element may be disposed on the upper side of the lower housing section. A power supply may be electronically coupled to the at least one upper motor and the lower motor.

In a set of embodiments, the cartridge may comprise a lower cartridge surface, and at least one side cartridge surface. The upper cartridge surface may comprise at least one, for example at least three, upper surface openings, for example cartridge top cover openings.

A well plate may be situated under the upper cartridge surface, wherein the well plate comprise at least one well. For example, at least three wells. The at least three wells may each comprise a well opening, wherein the well plate may be configured to rotate such that one or more well openings may align with one or more upper surface openings.

One or more raised processing elements may be disposed along an interior side of at least one well, for example along a distal bottom side of at least one well.) A raised processing opening may be disposed on the upper cartridge surface, wherein the raised processing opening may be configured to receive a mortar cup (or cup). A mortar screen (or screen) may be transversely disposed within the mortar cup (or cup). The mortar cup (or cup) may comprise at least one tab.

The pestle may comprise a pestle top cap, wherein the pestle top cap may comprise an opening configured to receive the pestle shaft (or shaft). The pestle may comprise a pestle spring; and/or a pestle spring cap configured to receive the pestle spring. The pestle may further comprise a pestle bottom cap; and/or a pestle body which may be configured to receive the pestle bottom cap.

The pestle may comprise a pestle head having at least one disaggregation side, wherein the pestle head may be configured to receive the pestle body. The pestle head may have at least one raised surface element disposed along the at least one disaggregation side. The pestle body may be configured to nest within the pestle head.

In some embodiments, the system may further comprise a set of tools, comprising at least one syringe, for example two syringes. The set of tools may further comprise at least one spray nozzle. In some embodiments, the system may further comprise at least one vial of enzyme solution and/or at least one vial of buffer solution.

In some embodiments, the raised surface element may comprise a plurality of pips disposed along the at least one disaggregation side. In some embodiments, at least one raised lateral element may be disposed along the surface of the pestle head.

In some embodiments, the disaggregation side may comprise a distal end and at least one side. The distal end may comprise a curved surface, where the curved surface may comprise a plurality of pips. The curved surface may comprise a raised spiral element.

The distal end may comprise a conical surface, where the conical surface may comprise a plurality of pips. The conical surface may comprise a raised spiral element.

In some embodiments, the distal end of the disaggregation side may comprise an inset terminus, wherein the inset terminus may comprise an exterior side and a terminal side. A plurality of pips may be disposed along the terminal side. A raised spiral element may be disposed along the terminal side.

In some embodiments, an interior ridge may be disposed along an interior side of the mortar cup (or cup), wherein the interior ridge may be configured to receive the raised lateral element such that the pestle head and mortar cup (or cup) may removably mate. In some embodiments, when the pestle head and mortar cup (or cup) removably mate, such as but not limited to the removable mating resulting from one or more raised lateral elements being in contact with an interior side of the mortar cup (or cup), the pestle may be able to lift, turn, or otherwise manipulate the mortar cup (or cup).

In some embodiments, the at least one upper motor may be configured to actuate the pestle shaft (or shaft) and by extension the pestle such that the pestle head moves either back and forth along a Y axis which may generate vertical force, in a rotational motion which may generate rotational force, or in both vertical and rotational motions which may generate grinding force. In some embodiments, the actuation of the pestle shaft (or shaft) may cause the pestle head, and in some embodiments the pestle head with at least one raised surface element disposed on the distal side of the pestle head, to apply the vertical, rotational, or grinding force, or a combination of two or more such forces, against a tissue sample. In some embodiments, the tissue sample may be disposed along a mortar screen (or screen) within the mortar cup (or cup). In some embodiments, the mortar cup (or cup) may be disposed within a well such that the mortar screen (or screen) is in contact with one or more raised processing elements which may be disposed along the interior of the well. In such embodiments, it is contemplated that the additional counterpressure provided by the plurality of raised processing elements may enhance the disaggregation effect of the vertical, rotational, or grinding forces, or the combination of two or more such forces, applied by the actuation of the pestle against the tissue sample.

In some embodiments, the mortar screen (or screen) may be configured to separate out particulates above 10 microns in size. In some embodiments, the mortar screen (or screen) may be configured to separate out particulates above 100 microns in size.

In some embodiments, the heating element may be configured to heat an effective amount of enzyme solution to an effective temperature. In some embodiments, the at least one well may be configured to retain buffer solution in the range of 1 ml to 100 ml. In some embodiments, the at least one well may be configured to retain buffer solution in the range of 1 ml to 500 ml. In some embodiments, at least one well is configured to receive a quantity of enzyme solution.

In some embodiments, the mortar screen (or screen) may be flat and disposed perpendicularly relative to the sides of the mortar cup (or cup). In some embodiments, the mortar screen (or screen) may be conical. The mortar cup (or cup) may comprise an inset mortar cup (or cup).

From a second aspect there is provided a method for automated preparation of a regenerative epidermal suspension. The method may comprise receiving, by a processor, an initiation signal, wherein the initiation signal indicates that a cartridge has been placed on a sensor.

The cartridge may contain (i) a cartridge top surface comprising a raised processing area, at least two openings, a mortar cup (or cup) disposed within the raised processing area, a mortar screen (or screen) disposed within the mortar cup (or cup), a tissue sample disposed within the mortar cup (or cup), and a pestle having a pestle head at its terminus, wherein the pestle is disposed within the mortar cup (or cup) and wherein the pestle rests on the tissue sample; (ii) a well plate and at least three wells disposed along the well plate, wherein a first well contains a quantity of enzyme, a second well contains a first quantity of buffer, and a third well contains a second quantity of buffer.

The method may further comprise activating a housing motor, wherein the housing motor is configured to operate a pestle shaft (or shaft). At least one base plate motor may be activated, wherein the at least one base plate motor is configured to spin the well plate.

The method may further comprise executing, by the base plate motor and the housing motor, at least one sequence. The at least one sequence may comprise actuating, by the housing motor, the pestle head within the mortar cup (or cup) in the presence of the enzyme solution for an effective amount of time, wherein said actuating may comprise moving the pestle head up and down along a vertical axis.

The at least one sequence may further comprise raising, by the housing motor, the mortar cup (or cup) to an upper position. The at least one sequence may further comprise pressing, by the housing motor, the pestle head against the tissue sample, wherein the tissue sample may be disposed along the mortar screen (or screen), wherein said pressing may comprise pressing the pestle head at least once, for example three times, and wherein each press may comprise an effective amount of force.

The at least one sequence may further comprise rotating, by the base plate motor, the well plate such that the well containing the mortar cup (or cup), tissue sample, and pestle head may be in fluidic contact with the first quantity of buffer. The at least one sequence may further comprise actuating, by the housing motor, the pestle head within the mortar cup (or cup) in the presence of the buffer solution for an effective amount of time. Said actuating may comprise moving the pestle head up and down along a vertical axis.

The at least one sequence may further comprise raising, by the housing motor, the mortar cup (or cup) to the upper position. The at least one sequence may further comprise pressing, by the housing motor, the pestle head against the tissue sample, wherein the tissue sample may be disposed along the mortar screen (or screen). Said pressing may comprise pressing the pestle head at least once, for example three times. Each press may comprise an effective amount of force.

The at least one sequence may further comprise rotating, by the base plate motor, the well plate such that the well containing the mortar cup (or cup), tissue sample, and pestle head may be in fluidic contact with the second quantity of buffer. The at least one sequence may further comprise actuating, by the housing motor, the pestle head within the mortar cup (or cup) in the presence of the second buffer solution. The pestle head may exert a rotational force and a grinding force on the tissue sample for an effective amount of time.

The at least one sequence may further comprise raising, by the housing motor, the mortar cup (or cup) to an upper position above the well plate. The at least one sequence may further comprise pressing, by the housing motor, the pestle head against the tissue sample, wherein the tissue sample may be disposed along the mortar screen (or screen). Said pressing may comprise pressing the pestle head at least once, for example three times. Each press may comprise an effective amount of force.

The at least one sequence may further comprise rotating, by the base plate motor, the well plate such that the well containing the second quantity of buffer may be disposed underneath one of the at least two openings. The at least one sequence may further comprise receiving, by a sensor, a completion signal, wherein the completion signal may be configured to indicate that a regenerative epidermal suspension is present within at least one well.

In some embodiments, a system for automated preparation of a regenerative epidermal suspension may comprise a non-transitory, tangible computer-readable medium having stored thereon computer-executable instructions, which, when executed by a computer processor, enable performance of a method of operating the system as described herein.

In some examples, a system for automated preparation of a regenerative epidermal suspension may comprise base unit comprising a tissue processing area, a cartridge configured to be received in the tissue processing area, comprising, a cover comprising an opening configured to receive a tissue sample, and a well plate situated under the cover and configured to rotate relative to the cover; and a tissue disaggregator configured to mechanically separate tissue when the tissue sample is positioned within the cartridge. The system may further comprise a heating element disposed within the base unit. The heating element may be configured to produce heat sufficient to improve enzyme efficiency of an enzyme positioned within the well plate. The tissue disaggregator may comprise a pestle. The base unit may comprise a tissue disaggregator shaft. The disaggregator shaft may be configured to be attached to the tissue disaggregator. The system may further comprise a cup comprising a screen disposed within the cup. The screen may be transversely oriented within the cup. The opening may comprise a raised portion and is configured to receive the cup. The well plate may comprise a well and the well plate is configured to rotate to align the well with the opening. The well plate may comprise a plurality of wells and the well plate may be configured to rotate to align each of the wells with the opening. The well plate may comprise a buffer well configured to receive a buffer and an enzyme well configured to receive an enzyme. The well plate may be configured to rotate to position the enzyme well under the opening when enzyme is to be used to disaggregate a tissue. The well plate may be configured to rotate to position the buffer well under the opening when buffer is to be applied to the tissue. The system may further comprise a processor configured to operate the tissue disaggregator and rotate the well plate.

In some examples, a system for automated preparation of a regenerative epidermal suspension may comprise a base unit comprising a tissue processing area, a cartridge configured to be received in the tissue processing area, comprising a cover comprising a raised processing opening configured to receive a cup, and a well plate situated under the cover and configured to rotate relative to the cover, the well plate comprising a well, and a tissue disaggregator configured to mechanically separate tissue when a tissue sample is positioned within the cup. The well plate may comprise at least a first well configured to receive an enzyme solution and a second well configured to receive a buffer solution, wherein the well plate may be configured to rotate to align either the first well or the second well with the raised processing opening. The cup may be configured to be lowered and raised into a well of the well plate.

The system of any one of claims 16-18, wherein the base unit comprises a heating element disposed within a housing.

The system of any one of claims 16-19, wherein the cartridge comprises the cup and a screen disposed within the cup.

In certain examples, a cartridge for preparation of a regenerative epidermal suspension may comprise a cover comprising a raised processing opening, a cup configured to be received within the raised processing opening, wherein the cup comprises a screen, and a well plate positioned under the cover and comprising a well, the well plate configured to rotate relative to the cover such that the well aligns with the raised processing opening. The screen may be positioned transversely within the cup. The screen may be configured to separate out particulates above 100 microns in size. The screen may be configured to separate out particulates above 50 microns in size. The screen may be configured to separate out particulates above 10 microns in size. The cartridge may include a docking spindle configured to connect to a base unit. The docking spindle may be configured to rotate the well plate. The well may comprise raised processing elements configured to enhance disaggregation of a tissue sample. The raised processing elements may be configured to enhance disaggregation of a tissue sample subjected to vertical, rotational, or grinding forces. The cup may be configured to be raised or lowered within the raised processing opening to position the cup in the well. The cover may comprise a plurality of openings. The cover may comprise a buffer opening. The well plate may comprise a plurality of openings. The well plate may comprise a buffer well and an enzyme well. The well plate may be configured to rotate such that the buffer well is positioned beneath the buffer opening. The well plate may be configured to rotate such that the enzyme well is positioned beneath the raised processing opening. The cup may be configured to receive a tissue disaggregator.

In some examples, a cartridge for preparation of a regenerative epidermal suspension may comprise a cover comprising an opening configured to receive a tissue sample; and a well plate positioned under the cover and comprising a well, the well plate configured to be rotated relative to the cover such that the well aligns with the opening. The cartridge may be configured to lower the tissue sample into the well aligned with the opening. The well plate may comprise a buffer well and an enzyme well, and the well plate is configured to rotate to align either the buffer well or the enzyme well with the opening. The cartridge may further comprise a cup receivable within the opening of the cover, the cup being moveable between a raised position above the well to a lowered position within the well.

In particular examples, a method for automated preparation of a regenerative epidermal suspension may comprise receiving, by a processor, an initiation signal, wherein the initiation signal indicates that a cartridge has been placed on a sensor, wherein the cartridge may comprise a cover, a cup containing a tissue sample, and a well plate situated beneath the cover, the well plate comprising a first well containing a quantity of enzyme solution and a second well containing a quantity of buffer solution. The method may include executing a sequence, wherein the sequence comprises actuating a tissue disaggregator against the tissue sample in the presence of the enzyme solution with the cup positioned in the first well, raising the cup to an upper position, rotating the well plate to position the second well beneath the cup, lowering the cup to a lower position within the second well and actuating the tissue disaggregator against the tissue sample in the presence of the buffer solution with the cup positioned in the second well. The tissue disaggregator may exert a rotational force on the tissue sample. The tissue disaggregator may exert a grinding force on the tissue sample. The tissue disaggregator may comprise a pestle. The tissue disaggregator comprises a raised surface element. The tissue disaggregator may comprise a plurality of pips. The tissue sample may be disposed along a screen disposed within the cup. The screen may be positioned transversely within the cup. The screen may be configured to separate out particulates above 100 microns in size. The screen may be configured to separate out particulates above 50 microns in size. The screen may be configured to separate out particulates above 10 microns in size.

In some examples, a method for automated preparation of a regenerative epidermal suspension (such as described in the previous paragraph) may comprise activating a housing motor, the housing motor configured to operate the tissue disaggregator. The housing motor may be configured to raise and lower the cup. The method may further comprise pressing the tissue disaggregator against the tissue sample a plurality of times when the cup is positioned in the first well and the second well. The method may further comprise actuating the tissue disaggregator against the tissue sample when the cup is in the upper position. The method may further comprise activating a base plate motor, the base plate motor configured to rotate the well plate. The method may further comprise rotating the well plate to position the cup in fluidic contact with a second quantity of buffer solution. The second quantity of buffer solution may be contained within a third well of the well plate. The method may further comprise actuating the tissue disaggregator against the tissue sample in the presence of the second quantity of buffer solution with the cup positioned in the third well, wherein the third well comprising one or more raised processing elements. The method may further comprise receiving a completion signal indicating that a regenerative epidermal suspension is present. The tissue disaggregator may be actuated against the tissue sample in the presence of the enzyme solution with the cup positioned in the first well for an amount of time effective to at least partially separate the tissue sample. The tissue disaggregator may be actuated against the tissue sample in the presence of the enzyme solution with the cup positioned in the first well for an amount of time effective to at least partially separate the tissue sample. The tissue disaggregator may be actuated against the tissue sample in the presence of the buffer solution with the cup positioned in the second well with an amount of force effective to at least partially separate the tissue sample. In some aspects, a non-transitory, tangible computer-readable medium having stored thereon computer-executable instructions, which when executed by a computer processor enable performance of the method as described herein this section or elsewhere in the specification.

In certain examples, a method of treating a tissue site may comprise collecting a tissue sample and placing the tissue sample in a cartridge comprising a well plate, the tissue sample comprising keratinocytes, positioning the cartridge within a base unit, the base unit comprising a tissue disaggregator, activating the base unit to rotate the well plate and operate the tissue disaggregator, wherein the well plate is rotated to align one or more wells in the well plate with the tissue sample and the tissue disaggregator, and wherein operation of the tissue disaggregator separates the tissue sample to form a regenerative epidermal suspension; and providing the regenerative epidermal suspension to a tissue site such that healing of the tissue site is enhanced. The tissue sample may comprise a skin sample. The regenerative epidermal suspension may comprise a mixed population of viable cells. The regenerative epidermal suspension may comprise fibroblasts. The regenerative epidermal suspension may comprise melanocytes. The tissue site may be a burn tissue site. The tissue site may be a full-thickness skin defect. The cartridge may comprise a cover comprising a raised processing opening. The method may further include placing the tissue sample in a cup positioned within the raised processing opening. Activating the base unit may cause the cup to be lowered into a well of the well plate. In certain examples, the tissue disaggregator may be a pestle. The well plate may comprise an enzyme well. The method may comprise placing an enzyme within the enzyme well, the enzyme configured to separate tissue. The well plate may be positioned such that the enzyme well is positioned beneath the tissue sample. Activating the base unit may cause the tissue aggregator to act on the tissue sample in the presence of enzyme in the enzyme well. The well plate may comprise a buffer well. The method may comprise placing a buffer within the buffer well. Activating the base unit may cause the well plate to rotate such that the buffer well is positioned beneath the tissue sample. Activating the base unit may cause the tissue aggregator to act on the tissue sample in the presence of the buffer in the buffer well. The well may comprise one or more raised processing elements.

DETAILED DESCRIPTION

Figure 1:
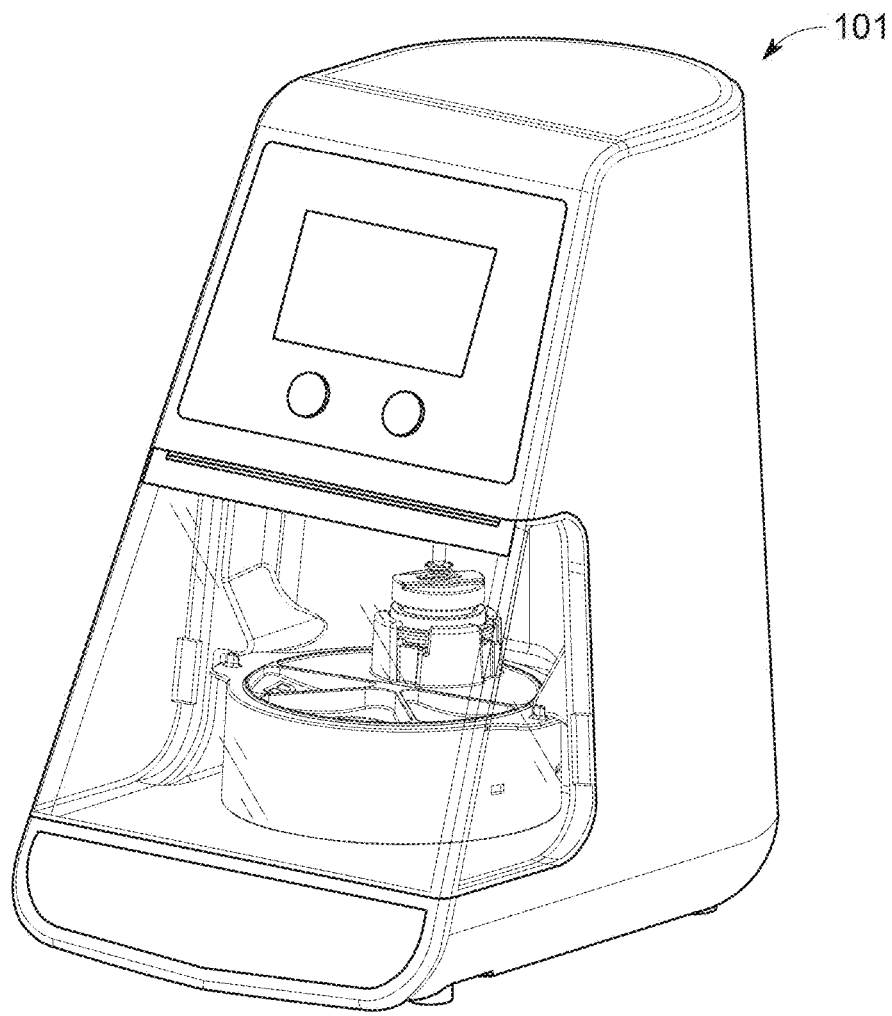
FIG. 1 is a front perspective view of a system for automated preparation of a regenerative epidermal suspension according to one or more embodiments of the present disclosure.

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims. For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

The devices, apparatuses, compositions, suspensions, methods and systems described herein may be used to treat a tissue site. Such a tissue site may be a wound site, a burn site, a full-thickness skin defect, a vitiligo lesion, a site undergoing and/or suitable for re-pigmentation, a user or surgeon created wound, a trauma, and/or any suitable injury or defect.

In some embodiments, one or more systems for automated preparation of a regenerative epidermal suspension comprises a base unit, a cartridge, and a tissue disaggregator. One of skill in the art will understand that a tissue disaggregator may be used to separate and/or disaggregate tissue. A tissue disaggregator may take many forms, such as a pestle, grinder, blade(s), various cutting and blunt instruments, cutting screens or any suitable tool. Although reference to a pestle is made throughout the specification, any suitable tissue disaggregator may be used. In some embodiments, the system may further comprise a set of accompanying tools.

The base unit may, in some embodiments, comprise a housing, a front cover, and a tissue processing area. In some embodiments, the housing may comprise one or more side panels, a housing top surface, a display with one or more buttons, a touchscreen, or both one or more buttons and a touchscreen, a base frontplate, and two or more base footpads. The base unit may further comprise a pestle shaft (or shaft), a power supply, one or more circuit boards having one or more memory units, and one or more motors. In some embodiments, the tissue processing area may comprise one or more heating elements, a docking spindle, one or more lighting elements, one or more side cartridge alignment protrusions, one or more rear cartridge alignment protrusions, and one or more control feedback sensors.

The cartridge assembly—or herein simply "cartridge"—may comprise a cartridge top cover, a raised processing area, one or more upper processing shelves, an "A", "B", "C", and "D" opening in the cartridge top cover, one or more cartridge tabs, a mortar top cap, a mortar polymer ring, a mortar cup (or cup), a mortar screen (or screen), a well plate, an "A", "B", and "C" well within the well plate, one or more raised processing elements within the "C" well, a well heater cup disposed underneath the "A" well of the well plate, a drive sleeve, a cartridge bottom cover, a cartridge chip, a bottom cover opening in the cartridge bottom cover, and a docking spindle opening in the bottom cover opening in the cartridge bottom cover. One of skill in the art will understand that the term "mortar cup" is interchangeable with the word "cup" and should not indicate that a pestle must be used with a cup. As will further be understood by one of skill in the art, a suitable container or any suitable receiving receptacle may be used in place of the mortar cup or cup, herein this section and throughout the specification. One of skill in the art will further understand that the term "mortar screen" is interchangeable with the term "screen" and should not indicate that a pestle must be used with the screen. As will further be understood by one of skill in the art, any suitable screen may be used in place of the mortar screen, herein this section and throughout the specification The pestle assembly—or herein simply "pestle"—may comprise a pestle top cap, a pestle spring, one or more pestle retention wires, a pestle spring cap, a pestle bottom cap, a pestle body, and a pestle head. In some embodiments, the pestle may further comprise a pestle shaft (or shaft).

As may be perceived in greater detail herein, the pestle head of the present disclosure may comprise at least one exterior side and a distal side, or "terminus" as used herein. In some embodiments, the terminus is planar. In some embodiments, the terminus is dome-shaped.

In some embodiments, the terminus comprises an inset terminus, wherein a column having a smaller circumference than the exterior side extends distally from the terminus. Relatedly, in some embodiments, the mortar cup (or cup) may comprise a sidewall, a distal opening, and a screen disposed across the distal opening. In some embodiments, the mortar cup (or cup) distal opening and screen may be configured to be perpendicular to the sidewall, thereby corresponding to the planar terminus embodiment of the pestle head. In some embodiments, the mortar cup (or cup) distal opening and screen may be curved, thereby corresponding to the dome-shaped terminus embodiment of the pestle head. In some embodiments, the mortar cup (or cup) distal opening and screen may be configured to comprise an inset opening with a screen disposed across the inset opening, thereby corresponding to the inset terminus embodiment of the pestle head. Relatedly, in some embodiments, the raised portion of one or more wells, such as but not limited to Well C, may be generally planar, curved, or inset so as to align with the planar, dome-shaped, or inset pestle head and related planar, curved, or inset distal end and configuration of the mortar cup (or cup).

The tools that accompany the cartridge and pestle may include, but are not limited to, one or more vials of buffer solution, one or more vials of enzyme solution, one or more vials of sterile water, one or more syringes, one or more needles, one more scalpels, one or more labels, and one or more spray nozzles.

An automated method of preparing a regenerative epidermal suspension may, in some embodiments, comprise (i) starting position verification; (ii) user set up; and (iii) one or more tissue processing sequences. One or more methods disclosed herein may further comprise post-processing by a user.

In embodiments, a system for automated preparation of a regenerative epidermal suspension may first verify the following starting positions: the mortar cup (or cup) is resting on the one or more upper processing shelves within the cartridge, the well plate is in the "A" position, and the pestle shaft (or shaft) is raised.

User setup may comprise, in some embodiments, the steps of: (a) powering on the system, (b) inserting a predetermined quantity of buffer into Well B (buffer well) and Well C through openings "B" and "C" in the cartridge top cover respectively, (c) inserting a predetermined quantity of enzyme solution into Well A (enzyme well) through opening "A" in the cartridge top cover, (d) obtaining a tissue sample, (e) placing the tissue sample in the mortar cup (or cup) within the raised processing area of the cartridge top cover, (f) placing the pestle on top of the tissue sample in the mortar cup (or cup) within the raised processing area of the cartridge top cover, (g) lifting the front cover, (h) placing the cartridge into the tissue processing area such that the cartridge chip aligns with one or more control feedback sensors, and such that the heating element is aligned with the well heating cup, (i) closing the front cover, and (j) pressing one or more buttons on the display to initiate processing.

One or more tissue processing sequences performed by the system may comprise, in embodiments, (a) the pestle shaft (or shaft) may lower and insert into the pestle cap through an opening in a top side of the pestle cap, (b) the pestle shaft (or shaft) may turn to engage the pestle body, (c) one or more raised elements disposed along an exterior side of the pestle body may engage with one or more recessed elements disposed along an interior side of the pestle head, (d) the pestle shaft (or shaft) may press, turn, or both press and turn the pestle body such that one or more raised lateral elements disposed on the exterior of the pestle head contacts an interior side of the mortar cup (or cup) and causes the mortar cup (or cup) to slip off the one or more upper processing shelves and lower into Well A (enzyme well), wherein when the mortar cup (or cup) is in Well A (enzyme well) the enzyme solution may pass through the mortar screen (or screen) and contact the tissue sample, (e) the heating element may warm the well heater cup, which in turn may warm the enzyme solution in Well A (enzyme well), (f) the pestle shaft (or shaft) may actuate the pestle up and down vertically in a predetermined sequence, (g) after a predetermined amount of time, the pestle shaft (or shaft) may rotate the pestle such that the pestle turns the mortar cup (or cup) in the opposite direction, which may raise the mortar cup (or cup) into the "up" position, wherein when the mortar cup (or cup) is in the "up" position, the edges of the mortar cup (or cup) may rest on the one or more upper processing shelves, (h) after a predetermined amount of time, the pestle shaft (or shaft) may press the pestle downward three times such that the pestle presses the tissue sample against the mortar screen (or screen), wherein such downward pressing may be performed at a predetermined pound force sufficient to squeeze the enzyme solution off of the tissue sample, (i) the well plate may rotate to align Well B (buffer well) underneath the raised processing area, (j) the pestle shaft (or shaft) may turn the pestle such that the pestle head engages with the mortar cup (or cup) and causes the mortar cup (or cup) to slip off the one or more upper processing shelves and lower into Well B (buffer well), wherein when the mortar cup (or cup) is in Well B (buffer well) the buffer solution may pass through the mortar screen (or screen) and contact the tissue sample, (k) the pestle shaft (or shaft) may actuate the pestle up and down vertically in a predetermined sequence, (l) after a predetermined amount of time, the pestle shaft (or shaft) may rotate the pestle such that the pestle turns the mortar cup (or cup) in the opposite direction, which raises the mortar cup (or cup) into the "up" position, wherein when the mortar cup (or cup) is in the "up" position, the edges of the mortar cup (or cup) rest on the one or more upper processing shelves, (m) after a predetermined amount of time, the pestle shaft (or shaft) may press the pestle downward three times such that the pestle presses the tissue sample against the mortar screen (or screen), wherein such downward pressing may be performed at a predetermined pound force sufficient to squeeze the buffer solution off of the tissue sample, (n) the well plate may rotate to align Well C underneath the raised processing area, (o) the pestle shaft (or shaft) may turn the pestle body such that the pestle head engages with the mortar cup (or cup) and causes the mortar cup (or cup) to slip off the one or more upper processing shelves and lower into Well C, wherein when the mortar cup (or cup) is in Well C the buffer solution may pass through the mortar screen (or screen) and contact the tissue sample, (p) the pestle shaft (or shaft) may rotate in a predetermined sequence, causing the pestle head to exert rotational and grinding forces on the tissue sample in the presence of the buffer solution, wherein the mortar screen (or screen) and raised processing elements may comprise the surfaces against which the tissue sample receives the rotational and grinding forces and may provide the related counterpressure, (q) after a predetermined amount of time, the pestle shaft (or shaft) may rotate the pestle body and pestle head such that the pestle turns the mortar cup (or cup) in the opposite direction, which raises the mortar cup (or cup) into the "up" position, wherein when the mortar cup (or cup) is in the "up" position, the edges of the mortar cup (or cup) rest on the one or more upper processing shelves, (r) after a predetermined amount of time, the pestle shaft (or shaft) may press the pestle downward three times such that the pestle presses the tissue sample against the mortar screen (or screen), wherein such downward pressing may be performed at a predetermined pound force sufficient to squeeze the buffer solution off of the tissue sample, (s) the well plate may rotate to align Well C underneath the "D" opening in the cartridge top cover, and (t) the sensor may send a signal to the one or more memory units to record the processing event.

In embodiments wherein the pestle shaft (or shaft) comprises a part of the pestle, the above-described sequence may alternatively comprise: (a) a retrieving element may lower from the upper housing portion and removably mate with the pestle shaft (or shaft), (b) the pestle shaft (or shaft) may turn to engage the pestle body, (c) one or more raised elements disposed along an exterior side of the pestle body may engage with one or more recessed elements disposed along an interior side of the pestle head, (d) the pestle shaft (or shaft) may press, turn, or both press and turn the pestle body such that one or more raised lateral elements disposed on the exterior of the pestle head contacts an interior side of the mortar cup (or cup) and causes the mortar cup (or cup) to slip off the one or more upper processing shelves and lower into Well A, wherein when the mortar cup (or cup) is in Well A the enzyme solution may pass through the mortar screen (or screen) and contact the tissue sample, (e) the heating element may warm the well heater cup, which in turn may warm the enzyme solution in Well A, (f) the pestle shaft (or shaft) may actuate the pestle up and down vertically in a predetermined sequence, (g) after a predetermined amount of time, the pestle shaft (or shaft) may rotate the pestle such that the pestle turns the mortar cup (or cup) in the opposite direction, which may raise the mortar cup (or cup) into the "up" position, wherein when the mortar cup (or cup) is in the "up" position, the edges of the mortar cup (or cup) may rest on the one or more upper processing shelves, (h) after a predetermined amount of time, the pestle shaft (or shaft) may press the pestle downward three times such that the pestle presses the tissue sample against the mortar screen (or screen), wherein such downward pressing may be performed at a predetermined pound force sufficient to squeeze the enzyme solution off of the tissue sample, (i) the well plate may rotate to align Well B (buffer well) underneath the raised processing area, (j) the pestle shaft (or shaft) may turn the pestle such that the pestle head engages with the mortar cup (or cup) and causes the mortar cup (or cup) to slip off the one or more upper processing shelves and lower into Well B, wherein when the mortar cup (or cup) is in Well B the buffer solution may pass through the mortar screen (or screen) and contact the tissue sample, (k) the pestle shaft (or shaft) may actuate the pestle up and down vertically in a predetermined sequence, (l) after a predetermined amount of time, the pestle shaft (or shaft) may rotate the pestle such that the pestle turns the mortar cup (or cup) in the opposite direction, which raises the mortar cup (or cup) into the "up" position, wherein when the mortar cup (or cup) is in the "up" position, the edges of the mortar cup (or cup) rest on the one or more upper processing shelves, (m) after a predetermined amount of time, the pestle shaft (or shaft) may press the pestle downward three times such that the pestle presses the tissue sample against the mortar screen (or screen), wherein such downward pressing may be performed at a predetermined pound force sufficient to squeeze the buffer solution off of the tissue sample, (n) the well plate may rotate to align Well C underneath the raised processing area, (o) the pestle shaft (or shaft) may turn the pestle body such that the pestle head engages with the mortar cup (or cup) and causes the mortar cup (or cup) to slip off the one or more upper processing shelves and lower into Well C, wherein when the mortar cup (or cup) is in Well C the buffer solution may pass through the mortar screen (or screen) and contact the tissue sample, (p) the pestle shaft (or shaft) may rotate in a predetermined sequence, causing the pestle head to exert rotational and grinding forces on the tissue sample in the presence of the buffer solution, wherein the mortar screen (or screen) and raised processing elements may comprise the surfaces against which the tissue sample receives the rotational and grinding forces and may provide the related counterpressure, (q) after a predetermined amount of time, the pestle shaft (or shaft) may rotate the pestle body and pestle head such that the pestle turns the mortar cup (or cup) in the opposite direction, which raises the mortar cup (or cup) into the "up" position, wherein when the mortar cup (or cup) is in the "up" position, the edges of the mortar cup (or cup) rest on the one or more upper processing shelves, (r) after a predetermined amount of time, the pestle shaft (or shaft) may press the pestle downward three times such that the pestle presses the tissue sample against the mortar screen (or screen), wherein such downward pressing may be performed at a predetermined pound force sufficient to squeeze the buffer solution off of the tissue sample, (s) the well plate may rotate to align Well C underneath the "D" opening in the cartridge top cover, and (t) the sensor may send a signal to the one or more memory units to record the processing event.

Post-processing by a user may comprise the steps of (a) raising the front cover, (b) inserting one or more syringes into Well C through the "D" opening in the cartridge top cover, (c) drawing up the regenerative epidermal suspension into the syringe, and (d) treating one or more treatment areas on a patient with the regenerative epidermal suspension. In some embodiments, the step of treating a patient with the regenerative epidermal suspension may comprise replacing the syringe's needle with a spray nozzle, then spraying the regenerative epidermal suspension on the treatment site.

Following processing, the system may raise the pestle shaft (or shaft) through the opening in the pestle top cap, and a user may remove the used cartridge and pestle. In embodiments wherein the pestle additionally comprises the pestle shaft (or shaft), the retrieving element may release the pestle shaft (or shaft), allowing the user to remove the used cartridge and pestle.

In some embodiments, a system for automated preparation of a regenerative epidermal suspension may comprise a non-transitory, tangible computer-readable medium having stored thereon computer-executable instructions, which, when executed by a computer processor, enable performance of a method may comprise (a) receiving, by a processor, an initiation signal, wherein the initiation signal indicates that a cartridge has been placed on a sensor, wherein the cartridge contains (i) a cartridge top surface comprising a raised processing area, at least two openings, a mortar cup (or cup) disposed within the raised processing area, a mortar screen (or screen) disposed within the mortar cup (or cup), a tissue sample disposed within the mortar cup (or cup), and a pestle having a pestle head at its terminus, wherein the pestle is disposed within the mortar cup (or cup) and wherein the pestle rests on the tissue sample; (ii) a well plate and at least three wells disposed along the well plate, wherein a first well contains a quantity of enzyme, a second well contains a first quantity of buffer, and a third well contains a second quantity of buffer; (b) activating a housing motor, wherein the housing motor is configured to operate a pestle shaft (or shaft); (c) activating at least one base plate motor, wherein the at least one base plate motor is configured to spin the well plate; (d) executing, by the base plate motor and the housing motor, at least one sequence, wherein the at least one sequence comprises the steps of (i) actuating, by the housing motor, the pestle head within the mortar cup (or cup) in the presence of the enzyme solution for an effective amount of time, wherein said actuating comprises moving the pestle head up and down along a vertical axis; (ii) raising, by the housing motor, the mortar cup (or cup) into an upper position, wherein said raising comprises actuating the pestle shaft (or shaft), which may actuate the pestle, which may be removably mated to the mortar cup (or cup) via contact between one or more raised lateral elements disposed on the pestle head and an interior side of the mortar cup (or cup), wherein said contact is sufficient to enable the pestle to lift, turn, or otherwise manipulate the mortar cup (or cup); (iii) pressing, by the housing motor, the pestle head against the tissue sample, wherein the tissue sample is disposed along the mortar screen (or screen), wherein said pressing comprises pressing the pestle head three times, and wherein each press comprises an effective amount of force; (iv) rotating, by the base plate motor, the well plate such that the well containing the mortar cup (or cup), tissue sample, and pestle head is in fluidic contact with the first quantity of buffer; (v) actuating, by the housing motor, the pestle head within the mortar cup (or cup) in the presence of the buffer solution for an effective amount of time, wherein said actuating comprises moving the pestle head up and down along a vertical axis; (vi) raising, by the housing motor, the mortar cup (or cup) to the upper position; (vii) pressing, by the housing motor, the pestle head against the tissue sample, wherein the tissue sample is disposed along the mortar screen (or screen), wherein said pressing comprises pressing the pestle head three times, and wherein each press comprises an effective amount of force; (viii) rotating, by the base plate motor, the well plate such that the well containing the mortar cup (or cup), tissue sample, and pestle head is in fluidic contact with the second quantity of buffer; (ix) actuating, by the housing motor, the pestle head within the mortar cup (or cup) in the presence of the second buffer solution such that the pestle head exerts a rotational force and a grinding force on the tissue sample for an effective amount of time; (x) raising, by the housing motor, the mortar cup (or cup) to an upper position above the well plate; (xi) pressing, by the housing motor, the pestle head against the tissue sample, wherein the tissue sample is disposed along the mortar screen (or screen), wherein said pressing comprises pressing the pestle head three times, and wherein each press comprises an effective amount of force; (xi) rotating, by the base plate motor, the well plate such that the well containing the second quantity of buffer is disposed underneath one of the at least two openings; and (xii) receiving, by a sensor, a completion signal, wherein the completion signal is configured to indicate that a regenerative epidermal suspension is present within at least one well.

One of skill in the art will understand that the initiation signal may be sent once the sensor detects the presence of the cartridge, and this may or may not start the sequence. However, in some examples, a user may start the sequence with a use start signal, such as by using a button, tap, switch, or any suitable mechanisms. In some examples, this signal may only be effective once the initiation signal from the sensor has been sent.

In some embodiments, the predetermined pound force sufficient to squeeze a solution off of the tissue sample may comprise 1-10 pounds of force, 2-5 pounds of force, 10-20 pounds of force, 20 pounds of force, or more than 20 pounds of force.

One or more embodiments of the present disclosure may be implemented as a program product for use with a computer system. The program(s) of the program product defines functions of the embodiments (including the methods described herein) and can be contained on a variety of computer-readable storage media. Illustrative computer-readable storage media include, but are not limited to: (i) writable storage media (e.g., a hard disk, a portable drive such as a USB stick or a floppy disk) on which alterable information is stored, or (ii) non-writable storage media (e.g., read-only memory devices within a computer such as CD-ROM disks readable by a CD-ROM drive) on which information is permanently stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media. In preferred embodiments, the computer-readable storage media of the present invention may comprise one or more printed circuit board assemblies communicatively coupled to one or more memory units housed within the enclosure of the present invention.

In general, the routines executed to implement the embodiments of the invention may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

As used herein, the term "digital" refers to any action, version, construct, representation, or other element that exists primarily or solely in a computer program or electronic medium.

As used herein, "effective", such as but not limited to an effective amount of time or an effective amount of one or more solutions means an amount sufficient to accomplish the intended task. By way of illustration and not limitation, an effective amount of enzyme solution may comprise between 1 and 100 ml of enzyme solution and an effective amount of buffer solution may comprise 1 to 200 ml of buffer solution. Likewise, in some embodiments and again for purposes of illustration and not limitation, an effective amount of time for a tissue sample to be in contact with the enzyme solution may comprise 5 to 30 minutes or in some embodiments 5 to 45 minutes or in some embodiments 5 to 60 minutes or longer. In some embodiments, an effective amount of time to heat the enzyme solution may be 1 to 15 minutes, 1 to 30 minutes or longer than 30 minutes. In some embodiments, the enzyme solution may comprise a pre-mixed solution comprising, at least, a quantity of enzyme in buffer solution, along with one or more additional elements.

The enzyme in the enzyme solution, in some embodiments may comprise but is not limited to one or more of trypsin, dispase, collagenase, trypsin-EDTA, thermolysin, pronase, hyaluronidase, elastase, papain and pancreatin. In some variations, one or more enzymes such as trypsin, dispase, collagenase, trypsin-EDTA, thermolysin, pronase, hyaluronidase, elastase, papain and pancreatin may be traditionally sourced, such as for example via fermentation, or may be recombinant- or animal-derived. In some variations, an enzyme solution may be formed by mixing lyophilized enzyme with an appropriate volume of fluid (e.g., water). In one or more embodiments, the enzyme may comprise a recombinant trypsin, dispase, collagenase, trypsin-EDTA, thermolysin, pronase, hyaluronidase, elastase, papain or pancreatin enzyme, or more than one such recombinant enzyme. When the enzyme used is trypsin, the enzyme solution is preferably free of calcium and magnesium.

FIG. 1 generally discloses an embodiment of a system for automated preparation of a regenerative epidermal suspension 101. Various elements of view in FIG. 1 will be elucidated in greater detail below.

Figure 2:
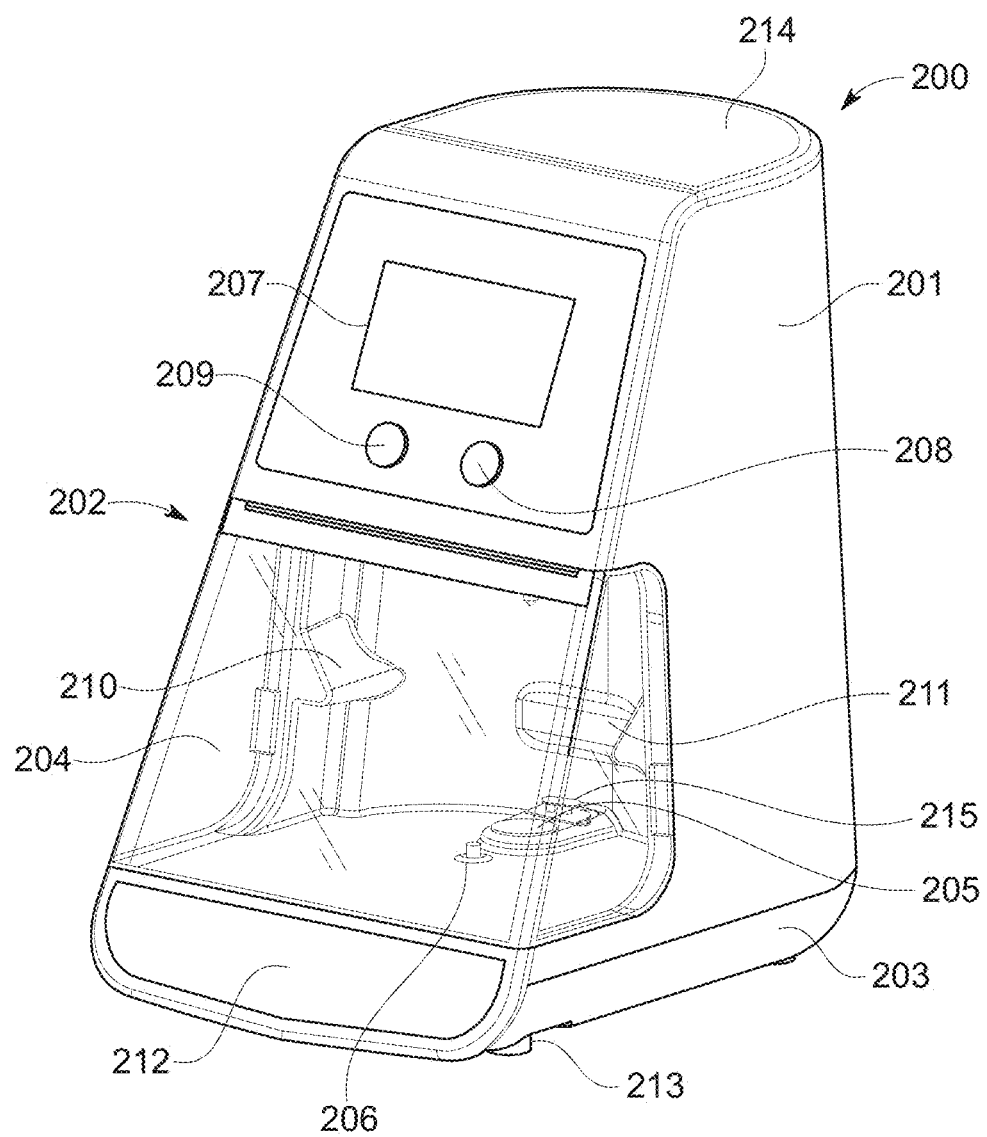
FIG. 2 is a front perspective view of a base unit according to one or more embodiments of the present disclosure.

FIG. 2 illustrates an embodiment of a base unit according to an embodiment of the present disclosure, more specifically, FIG. 2 illustrates base unit 200, housing 201, tissue processing area 202, housing base 203, front cover 204, heating element 205, docking spindle 206, display 207, menu button 1 208, menu button 2 209, side cartridge alignment protrusions 210, rear cartridge alignment protrusion 211, base frontplate 212, base pads 213, housing top surface 214, and control feedback sensor 215.

As can be seen in FIG. 2, it is contemplated that in at least one embodiment, base unit 200 and its housing 201 may generally comprise a countertop-sized unit that widens from the housing top surface 214 towards its base and ultimately base pads 213. In some embodiments, the front end of housing 201 extending from display 207 to base front plate may be generally planar, as can be seen in FIG. 2. Moreover, in some embodiments, two, three, four, five, or more base pads 213 are contemplated. Base unit 200 may further comprise one or more computer processing elements, such as but not limited to one or more printed circuit board assemblies, one or more hard drives, one or more circuit boards, one or more motherboards, one or more central processing units, one or more computer memory elements, one or more pieces of random access memory, and one or more processors (none shown). Moreover, in addition or alternative to the shape of base unit 200 as generally shown in FIG. 1 and FIG. 2, base unit 200 may comprise shapes such as a cylinder, a cube, a sphere, a pyramid, a cuboid, a hexagonal prism, or any other shape that would enable performance of the present disclosure. As may be contemplated by those of skill in the art, certain related elements may in such embodiments comprise different shapes as well. By way of illustration and not limitation, were base unit 200 to be shaped as a cylinder, front cover 204 and display 207 may be curved to match. Similarly, it is contemplated that such related configuration or design changes may be made in order to practice the invention across different embodiments. In some embodiments, base unit 200 may itself be comprised of different subassemblies that may be used in conjunction with each other to produce one or more regenerative epidermal suspensions.

Heating element 205 is generally shown in FIG. 2 as a metal plate configured to conduct heat through well heater cup 318, as is discussed more fully below. In some embodiments, however, other heating means are contemplated, such as but not limited to chemical heat elements such as a blister pack that heats when activated, radiation-heating elements, or other heating elements known in the art.

In some embodiments, front cover 204 may comprise a flat cover. In some embodiments, front cover 204 may comprise a rounded cover. In some embodiments, front cover 204 may be shaped approximately as three sides of a square. In some embodiments, front cover 204 may taper downwards, such that the upper portion of front cover 204 may be narrower than the bottom portion of front cover 204. Conversely, in some embodiments, the upper portion of front cover 204 may be wider than the lower portion of front cover 204. In some embodiments, front cover 204 may be translucent, clear, or otherwise "see-through." In some embodiments, front cover 204 may be partially translucent and partially opaque. In some embodiments, front cover 204 may be opaque. In some embodiments, front cover 204 may be omitted.

As will be seen by comparing the cartridge top cover 301 generally and cartridge tab(s) 308 more specifically, descriptions of which follow, a user may observe that cartridge alignment protrusions 210 and rear cartridge alignment protrusion 211 may be configured, in some embodiments, to hold cartridge 300 in place during one or more processing sequences. In embodiments wherein cartridge top cover 301 is of a different height, cartridge alignment protrusions 210 and rear cartridge alignment protrusion 211 may in turn be placed either lower or higher, or one higher and the other lower, within tissue processing area 202. In one or more alternative embodiments, tabs or protrusions may extend from front cover 204 to removably mate with cartridge alignment protrusions 210.

Docking spindle 206, in some embodiments, may be configured to align with drive sleeve 319. In some embodiments, however, docking spindle 206 may take any shape that may be advantageous to mate with drive sleeve 319, or comparable element, that may be configured to rotate well plate 313. By way of illustration and not limitation, docking spindle 206, or its comparable element, may mate with drive sleeve 319, or its comparable element, may reversibly mate via magnetic connection mating, Luer locking, snap-fit mating, bayonet-style mating, air hose style quick-connect mating, press-fit mating, "Mix2Vial" mating, and any other form of temporary, reversible, or in some embodiments permanent mating methods known in the relevant art.

In some embodiments, control feedback sensor 215 may comprise a temperature sensor, an electro-mechanical sensor, a pressure sensor, a vibration sensor, a light sensor, a sensor having two or more such properties, or two or more sensors working as a unit. As used herein, "sensor" and "control feedback sensor" encompass both one sensor and two or more communicatively coupled sensors. Tissue processing sensor 215 may further comprise a chip, which in some embodiments may comprise a programmable chip. In some embodiments, the one or more programmable chips in or connected to control feedback sensor 215 may be configured to receive and store information sufficient to indicate that a particular cartridge assembly 300 is a new cartridge assembly 300 or is a used cartridge assembly 300. In additional or alternative embodiments, cartridge assembly 300 may further comprise one or more cartridge assembly programmable sensors (not shown). In such embodiments, control feedback sensor 215 may be configured to cause the cartridge assembly sensor to read as new or used. In some embodiments, control feedback sensor may be configured to communicate with the one or more computer elements via Bluetooth, near-field communication (NFC), inter-integrated circuit serial communication (I2C), serial peripheral interface (SPI), or any other such communications element.

Additionally, FIG. 2 also shows the terminus of pestle shaft (or shaft) 401. In some embodiments, one or more motors (not shown) may actuate pestle shaft (or shaft) 401 up and down, rotationally, laterally, or in more than one such motion, within tissue processing area 202. In some embodiments, therefore, pestle shaft (or shaft) 401 may extend further into tissue processing area 202 than is generally shown in FIG. 2.

Figure 3A:
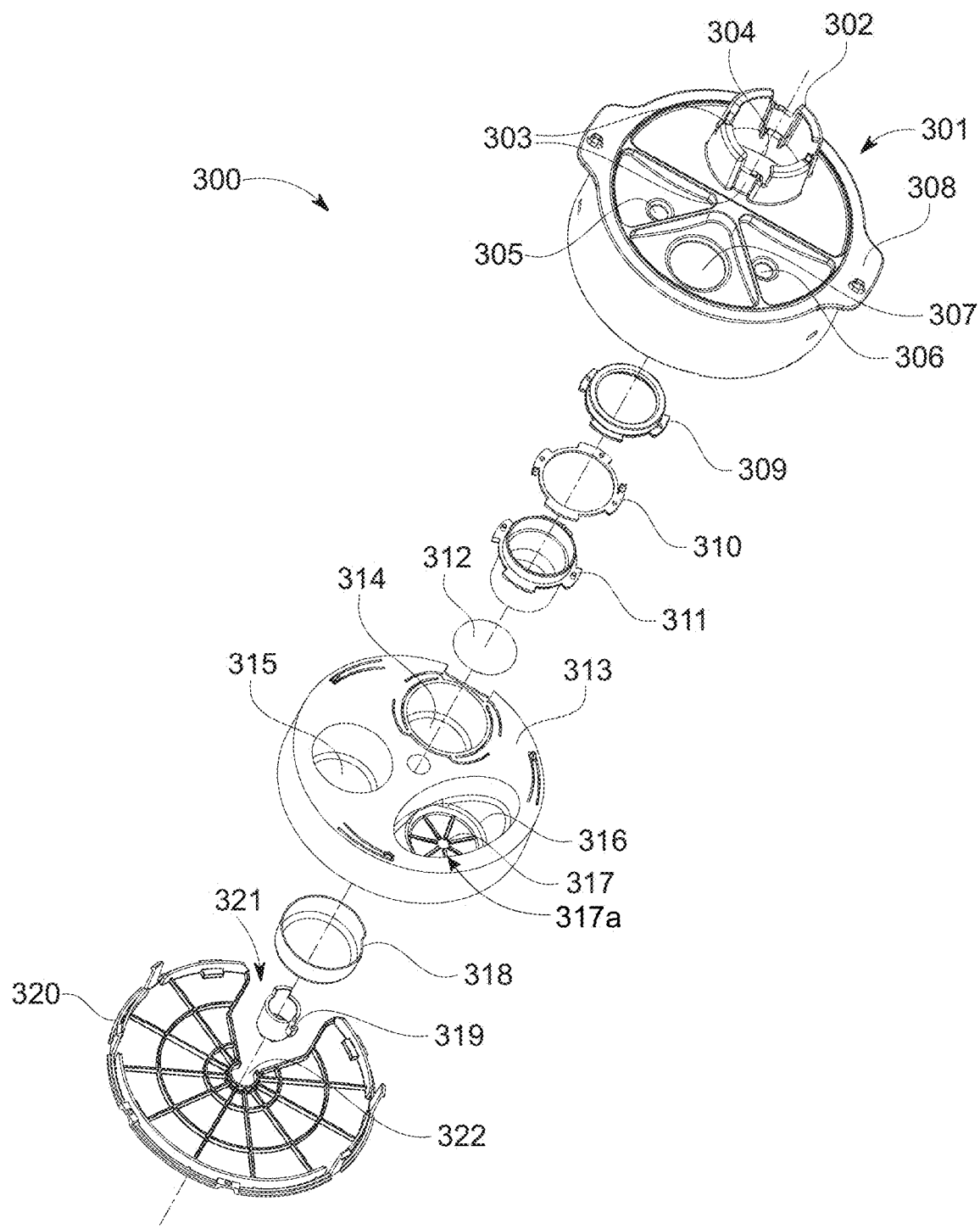
FIG. 3A is an exploded perspective view of a cartridge assembly according to one or more embodiments of the present disclosure.

Turning attention to FIG. 3A, the reader can observe an exploded perspective view of a cartridge assembly according to an embodiment of the present disclosure. More specifically, FIG. 3A tends to show cartridge assembly 300, cartridge top cover 301, raised processing area 302, upper processing shelf 303, "A" opening 304, "B" opening 305, "C" opening 306, "D" opening 307, cartridge tab 308, mortar top cap 309, mortar polymer ring 310, mortar cup (or cup) 311, mortar screen (or screen) 312, well plate 313, Well A 314, Well B 315, Well C 316, raised processing elements 317, lower well portion 317a, well heater cup 318, drive sleeve 319, cartridge bottom cover 320, bottom cover opening 321, docking spindle opening 322, and connection tabs 325.

In some embodiments, such as generally shown in FIG. 3A, cartridge top cover 301 may be generally disc shaped. In other embodiments, cartridge top cover 301 may be square-shaped, spherical, cube shaped, oblong, star-shaped, triangular, or any other shape capable of carrying out the present system and/or method. Similarly, in some embodiments, any of "A" opening 304, "B" opening 305, "C" opening 306, and/or "D" opening 307 may be larger or smaller than generally shown in FIG. 3A. As well, in some embodiments, any of "A" opening 304, "B" opening 305, "C" opening 306, and/or "D" opening 307 may be of a different shape than a circle, such as for example an oval, a square, a diamond, or a triangle.

As can be seen in FIG. 3A, it is contemplated that in some embodiments one or more of mortar top cap 309, mortar polymer ring 310, and/or mortar cup (or cup) 311 may comprise one or more wing-shaped tabs on its upper surface. As may be inferred by an examination of raised processing area 302, upper processing shelf 303, and "A" opening 304, such wing-shaped tabs may be configured to rest mortar cup (or cup) 311 in either a raised or lowered position within raised processing area 302, such as for purposes of illustration and not limitation by either resting on one or more upper processing shelves 303 or lowering down with "A" opening 304 to a lower position within raised processing area 302, such as but not limited to a position wherein mortar screen (or screen) 312, mortar cup (or cup) 311, and a tissue sample are positioned within Well A 314, Well B 315, or Well C 316 in the presence of either enzyme solution or buffer solution.

In some embodiments, mortar screen (or screen) 312 may comprise one or more of a membrane filter, a 100 micron filter, a 50 micron filter, a 25 micron filter, a 10 micron filter, a 5 micron filter, a 1 micron filter, a magnetic filter, a microbead filter, a magnetic microbead filter, antibody/antigen receptors used as a filter, one or more size exclusion column(s), one or more centrifuges, or filtration via ionic exchange/polarity column. As used herein, unless context indicates otherwise, the terms "screen" and "filter" are interchangeable.

In some embodiments, well plate 313 may be configured to rotate Well A 314, Well B 315, or Well C 316 underneath "A" opening 304 and raised processing area 302, such that one or more wells that were originally located under "A" opening 304, "B" opening 305, "C" opening 306, or "D" opening 307 may be rotated to align under "A" opening 304 and raised processing area 302. It is contemplated that such rotation may be achieved, in some embodiments, when mortar cup (or cup) 311 is in the upper position and resting on upper processing shelves 303.

In some embodiments, one or more of Well A 314, Well B 315, or Well C 316 may be pre-filled with processing media. This processing media may include, but not limited to, sterile water, buffer, enzyme, or a combination thereof.

Turning attention to raised processing elements 317, as is discussed in more detail elsewhere herein, in some embodiments one or more motors of the present system may drive the pestle shaft (or shaft) 401 such that it causes pestle head 407 to apply rotational and grinding forces against a tissue sample in the presence of either enzyme solution or buffer solution, or both, inside of mortar cup (or cup) 311 and against mortar screen (or screen) 312 while pestle 400 is within mortar cup (or cup) 311 and mortar screen (or screen) 312, and wherein mortar cup (or cup) 311 and mortar screen (or screen) 312 are in contact with such fluid while in Well A 314, Well B 315, or Well C 316. In some embodiments, while within Well C 316, mortar screen (or screen) 312 may rest on raised processing elements 317. In such embodiments, when pestle 400 exerts rotational and grinding force on the tissue sample within mortar cup (or cup) 311 and against mortar screen (or screen) 312, it is contemplated that raised processing elements 317 may provide additional friction surfaces that may in some embodiments enhance the mechanical disaggregation caused by the rotational and grinding forces of pestle cap 407. For example, it is contemplated that one or more raised processing elements 317 may keep one or more pieces of the tissue sample in place while pestle head 407 grinds on said tissue sample piece, thereby achieving enhanced mechanical disaggregation of the tissue sample piece. In some embodiments, raised processing elements 317 may comprise a separate plate that rests in one or more of Well A 314, Well B 315, or Well C 316. In some embodiments, the one or more raised processing elements 317 may be configured as one or more straight line raised ridges that radiate out from a central point. In some embodiments, the one or more raised processing elements 317 may be configured as one or more spiral-shaped ridges. In alternative embodiments, the one or more raised processing elements 317 may comprise a plurality of pips or dots. In such embodiments, such pips or dots may be randomized in their placement, placed in a grid formation, be placed in a spiral orientation, or in any geometrical pattern.

Lower well portion 317a may, in some embodiments, comprise the recessed portion of Well C 316, which as may be seen in FIG. 3A, may in some embodiments comprise one or more raised processing elements 317 on the surface of lower well portion 317a. In some embodiments, lower well portion 317a may be generally curved, flat, conical, or inset. In some embodiments, the shape of lower well portion 317a may be configured to align with the terminal portion of pestle head 407 and the shape of mortar screen (or screen) 312. By way of illustration and not limitation, should the terminal portion of pestle head 407 be flat, mortar screen (or screen) 312 may be flat and lower well portion 317a may be either flat or slightly curved. As well, should the terminal portion of pestle head 407 be curved, mortar screen (or screen) 312 may be curved and lower well portion 317a may be curved. Similarly, should the terminal portion of pestle head 407 be conical, conical mortar screen (or screen) 707 may be provided and lower well portion 317a may be conical, such as for example, alternative lower well portion 322. And, should the terminal portion of pestle head 407 be inset such as for example shown in FIG. 5I and FIG. 5J, inset mortar cup (or cup) 710 may be provided and lower well portion 317a may be inset such as for example inset lower well portion 801. In some embodiments, the diameter of pestle head 407 may be configured to fit within the lower opening of mortar cup (or cup) 311 or the lower opening of inset mortar cup (or cup) 710.

Similarly, as may be disclosed in more detail elsewhere herein, in some embodiments the diameter of the lower opening of mortar cup (or cup) 311 may comprise 2 cm. In some embodiments, the diameter of the lower opening of inset mortar cup (or cup) 710 may comprise 2 cm. Relatedly, in some embodiments, the diameter of pestle head 407 may comprise 2 cm or slightly less than 2 cm. In related embodiments, the diameter of lower well portion 317a may comprise 2 cm or slightly larger than 2 cm. In some embodiments, the diameter of inset lower well portion 801 may comprise 2 cm or slightly larger than 2 cm. In some embodiments, the diameter of mortar screen (or screen) 312 may comprise 2 cm or slightly larger than 2 cm.

Similarly, in some embodiments the diameter of the lower opening of mortar cup (or cup) 311 may comprise 1 cm. In some embodiments, the diameter of the lower opening of inset mortar cup (or cup) 710 may comprise 1 cm. Relatedly, in some embodiments, the diameter of pestle head 407 may comprise 1 cm or slightly less than 1 cm. In related embodiments, the diameter of lower well portion 317a may comprise 1 cm or slightly larger than 1 cm. In some embodiments, the diameter of inset lower well portion 801 may comprise 1 cm or slightly larger than 1 cm. In some embodiments, the diameter of mortar screen (or screen) 312 may comprise 1 cm or slightly larger than 1 cm.

Relatedly, in some embodiments the diameter of the lower opening of mortar cup (or cup) 311 may comprise 2 cm to 5 cm. In some embodiments, the diameter of the lower opening of inset mortar cup (or cup) 710 may comprise 2 cm to 5 cm. Relatedly, in some embodiments, the diameter of pestle head 407 may comprise 2 cm to 5 cm. In related embodiments, the diameter of lower well portion 317a may comprise 2 cm to 5 cm. In some embodiments, the diameter of inset lower well portion 801 may comprise 2 cm to 5 cm. In some embodiments, the diameter of mortar screen (or screen) 312 may comprise 2 cm to 5 cm.

As well, in some embodiments the diameter of the lower opening of mortar cup (or cup) 311 may be greater than 5 cm. In some embodiments, the diameter of the lower opening of inset mortar cup (or cup) 710 may be greater than 5 cm. Relatedly, in some embodiments, the diameter of pestle head 407 may be greater than 5 cm. In related embodiments, the diameter of lower well portion 317a may be greater than 5 cm. In some embodiments, the diameter of inset lower well portion 801 may be greater than 5 cm. In some embodiments, the diameter of mortar screen (or screen) 312 may be greater than 5 cm.

Similarly, in some embodiments the diameter of the lower opening of mortar cup (or cup) 311 may be less than 1 cm. In some embodiments, the diameter of the lower opening of inset mortar cup (or cup) 710 may be less than 1 cm. Relatedly, in some embodiments, the diameter of pestle head 407 may be less than 1 cm. In related embodiments, the diameter of lower well portion 317a may be less than 1 cm. In some embodiments, the diameter of inset lower well portion 801 may be less than 1 cm. In some embodiments, the diameter of mortar screen (or screen) 312 may be less than 1 cm.

As may be generally seen in FIG. 3A, one or more of Well A 314, Well B 315, or Well C 316 may be shaped generally as cylinders and accordingly comprise at least one sidewall and at least one distal or bottom side. It is contemplated that in some embodiments, one or more of Well A 314, Well B 315, or Well C 316 may comprise shapes other than cylinders, such as spherical, cuboid, or any other geometric shape. The at least one raised processing element may be disposed along one or more of the at least one sidewall or distal bottom end of one or more of Well A 314, Well B 315, or Well C 316.

It is contemplated that, in some embodiments, the diameter of Well C 316 may be narrower or wider, or its vertical length deeper or shallower, to allow for differences in buffer solution, which in turn may allow for differences in the present disclosure's regenerative epidermal solution's expansion ratio. By way of illustration and not limitation, in some embodiments, the diameter of Well C 316 may be either narrower or shallower, or both narrower and shallower, to support processing either a smaller volume of buffer, such as 5 mls, or a larger volume of buffer, such as 500 mls, by a system for automated preparation of a regenerative epidermal suspension according to at least one embodiment of the present disclosure.

As may be seen when comparing FIG. 2 and FIG. 3A, in some embodiments, cartridge bottom cover 320, bottom cover opening 321, and docking spindle opening 322 may be configured such that they are configured to wrap around heating element 205, docking spindle 206, and control feedback sensor 215. In other embodiments, cartridge bottom cover 320 may comprise a shape with no cutout, such that cartridge bottom cover 320 is configured to rest on top of one or more of heating element 205, docking spindle 206, and control feedback sensor 215. It is contemplated that in some embodiments, one or more motors in housing 201 may drive docking spindle 206 such that docking spindle 206 turns against drive sleeve 319, which then may rotate well plate 313 within cartridge top cover 301.

In some embodiments, cartridge assembly 300 and its constituent parts, such as but not limited to cartridge top cover 301, raised processing area 302, "A" opening 304, "B" opening 305, "C" opening 306, "D" opening 307, well plate 313, Well A 314, Well B 315, Well C 316, heater cup 318, drive sleeve 319, and cartridge bottom cover 320 may be configured in a linear format. By way of illustration and not limitation, in some embodiments, cartridge top cover 301 may be generally rectangular in shape, with raised processing area 302 and its "A" opening 304, "B" opening 305, "C" opening 306, and "D" opening 307 disposed in a line along the top edge of cartridge top cover 301. Correspondingly, in such embodiments and by way of illustration and not limitation, well plate 313 may be generally rectangular also, with Well A 314, Well B 315, and Well C 316 disposed in a line. In such embodiments, cartridge bottom cover 320 may also be configured in a rectangle shape. It should be appreciated that in the above example, a linear arrangement of such elements as raised processing area 302, "A" opening 304, "B" opening 305, "C" opening 306, "D" opening 307, Well A 314, Well B 315, Well C 316, heater cup 318, or drive sleeve 319 does not necessarily necessitate a rectangular configuration of elements such as but not limited to cartridge top cover 301, well plate 313, and cartridge bottom cover 320. Rather, cartridge top cover 301, well plate 313, and cartridge bottom cover 320, and any other element discussed herein, may be configured in a different shape, such as an oval, a square, or a circle and still be configured to support a linear motion and processing sequence.

As may be appreciated by those of skill in the art, in alternative embodiments it is contemplated that one or more of "A" opening 304, "B" opening 305, "C" opening 306, "D" opening 307, Well A 314, Well B 315, or Well C 316 may be labeled with alternative identifying marks such as numbers, symbols, colors, color coding, or other sequential or nonsequential identifying marks. By way of illustration and not limitation, in some embodiments "A" opening 304, "B" opening 305, "C" opening 306, and "D" opening 307 may be numbered 1, 2, 3, and 4, while Well A 314, Well B 315, and Well C 316 may retain their alphabetic designations. Again alternatively and solely for purposes of example, in some embodiments "A" opening 304, "B" opening 305, "C" opening 306, and "D" opening 307 may retain their alphabetic designations, while Well A 314, Well B 315, and Well C 316 may be numbered 1, 2, 3, and 4.

In some embodiments, the tissue sample may be harvested via corkscrew slicer such as a food processor, by electroporation, by biopsy, by punch biopsy, by dermatome, by DermaBlade, or by any other instrument or method known in the relevant art for skin sample acquisition and/or tissue sample acquisition.

In some embodiments, deactivation of the enzyme may be accomplished in one or more of Well A 314, Well B 315, or Well C 316 by rinsing the tissue sample in buffer, one or more trypsin inhibitors, by vacuum removal, by semipermeable membrane, by an enzyme-specific receptor in a column filtration process, by pressure differential, by magnetic microbeads, or by any other method known in the relevant art.

In some embodiments, fluid transfer within cartridge assembly 300 may be accomplished by syringe plunger/pulling action, by magnetic fluid transfer, by motorized fluid transfer for example a stepper, by vacuum pressure, by fluidic pressure, by gravity, by concentration gradient, or any other such mechanism known in the art.

In some embodiments, the regenerative epidermal suspension may be applied to a patient by direct spray on a treatment area via a spray nozzle, direct spray on a treatment area via an ultrasonic or piezoelectric atomizer, direct spray on a treatment area via a rotating spray nozzle having variable spray patterns, by dripping on a treatment area using a dripper or a syringe, by application to a dressing or media, by combining the regenerative epidermal suspension with a foam, by combining the regenerative epidermal suspension with an electrospun bandage, by combining the regenerative epidermal suspension with a wearable such as but not limited to a glove or socks, by combining the regenerative epidermal suspension with elements required to make a paste, by combining the regenerative epidermal suspension with elements required to make a salve, by combining the regenerative epidermal suspension with elements required to make a balm, by combining the regenerative epidermal suspension with elements required to make a "lipstick" style applicator, or by any other application or combination known in the art.

Remaining with FIG. 3A, an observer may discern that Well C 316 may in some embodiments comprise an oval-shaped upper well portion, one or more moon-shaped lower well shelfs, a lower well portion with in some embodiments raised processing elements 317 disposed along the lower well portion, and an inner well portion located at the center of the lower well portion. As may be generally seen in FIG. 3A, in some embodiments, the lower well portion may comprise a shallow fluid receptacle. Also as may be seen in FIG. 3A, in some embodiments, the lower well portion may generally comprise a circular shape. A viewer of FIG. 3A may also perceive that the inner well portion may itself also be circular, and may as mentioned in some embodiments be disposed in the center of the lower well portion.

Still with attention to FIG. 3A, as may be discerned by those of skill in the art, lower well portion, together with raised processing elements 317, may slope towards the inner well portion at a variety of degrees. FIG. 3A discloses a relatively flat slope, but as may be seen in FIG. 7, other embodiments may provide for an inner well portion having steeper slopes. Inner well portion may in some embodiments be shaped as a shallow tray with a slight slope towards its center, as generally disclosed in FIG. 3A, or may be more conical, as depicted in FIG. 7. As may be appreciated by those of skill in the art, raised processing elements 317 may, in such alternative embodiments of lower well portion, comprise more or fewer elements than shown in FIG. 3A, or may comprise a different orientation than shown. Additionally, in some embodiments, inner well portion may comprise a flat surface, may itself comprise a depression, or may in some embodiments comprise a raised element.

Figure 3B:
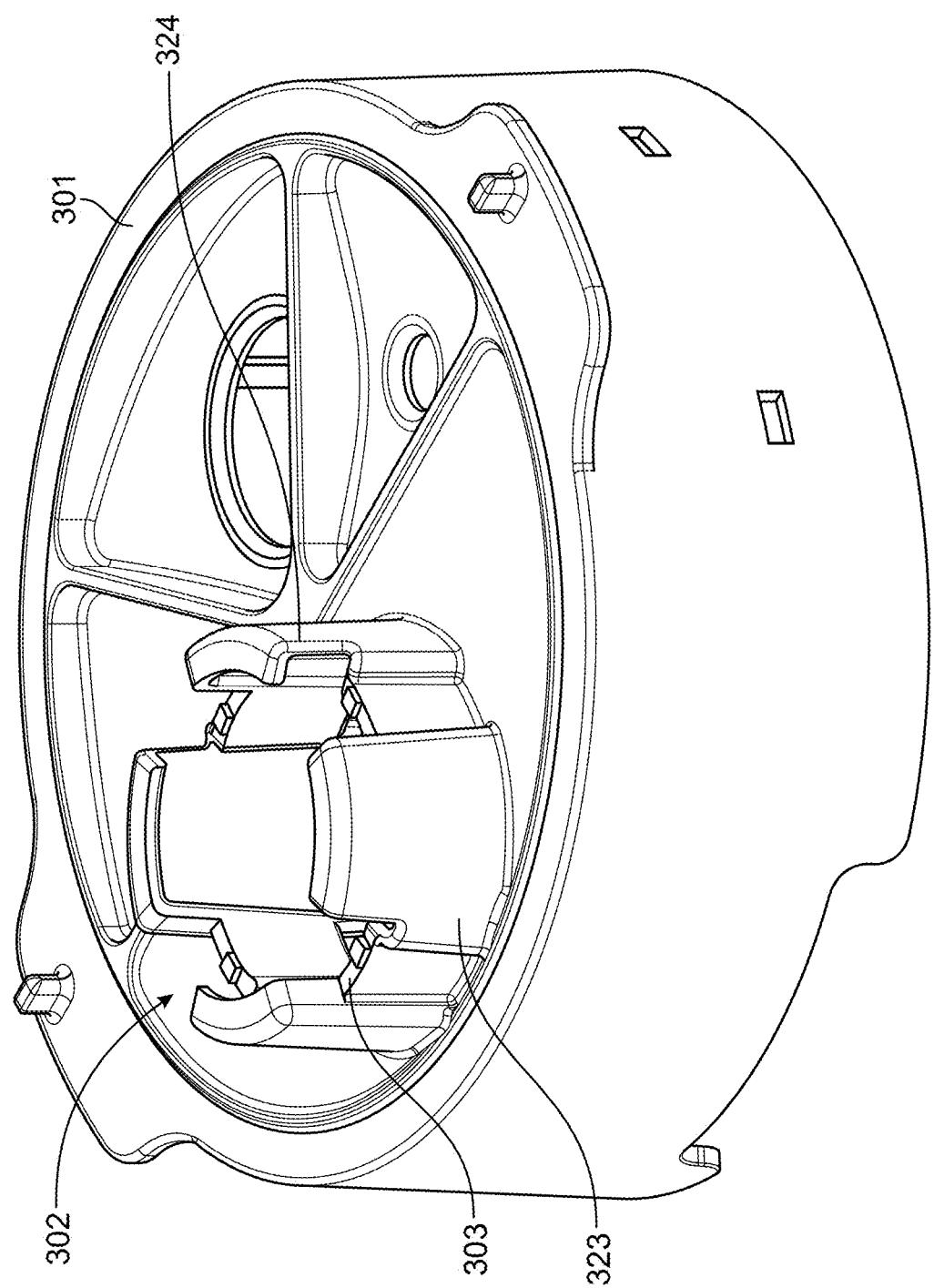
FIG. 3B is a top perspective view of a cartridge top cover according to one or more embodiments of the present disclosure.

FIG. 3B shows additional detail on cartridge top cover 301, raised processing area 302, and upper processing shelf 303, among other elements. As can be seen in FIG. 3B, raised processing area 302 may generally comprise one or more vertical elements 323, each of which may further comprise a cutout 324. As may be seen in reference to FIG. 7A, raised processing area 302 may be configured that cutout 324 may be configured to allow passage of one or more mortar cup (or cup) tabs 701 through its interior, and upper processing shelf 303 may be configured such that a mortar cup (or cup) tab 701 may rest upon the surface of upper processing shelf, thereby creating space under mortar cup (or cup) 311 and the lower portions of raised processing area 302. Such space may, in some embodiments, enable well plate 313 to rotate one or more of Well A 314, Well B 315, or Well C 316 underneath mortar cup (or cup) 311. Accordingly and in the reverse, the present system may be configured such that by turning pestle 400 while pestle 400 is removably mated to mortar cup (or cup) 311, mortar cup (or cup) tabs 701 may twist off of upper processing shelf 303, pass through cutout 324, and allow mortar cup (or cup) 311 to lower within vertical element 323 to a lower position, wherein at least a portion of mortar cup (or cup) 311 may be inside of Well A 314, Well B 315, or Well C 316 in a lower position within raised processing area 302.

Figure 3C:
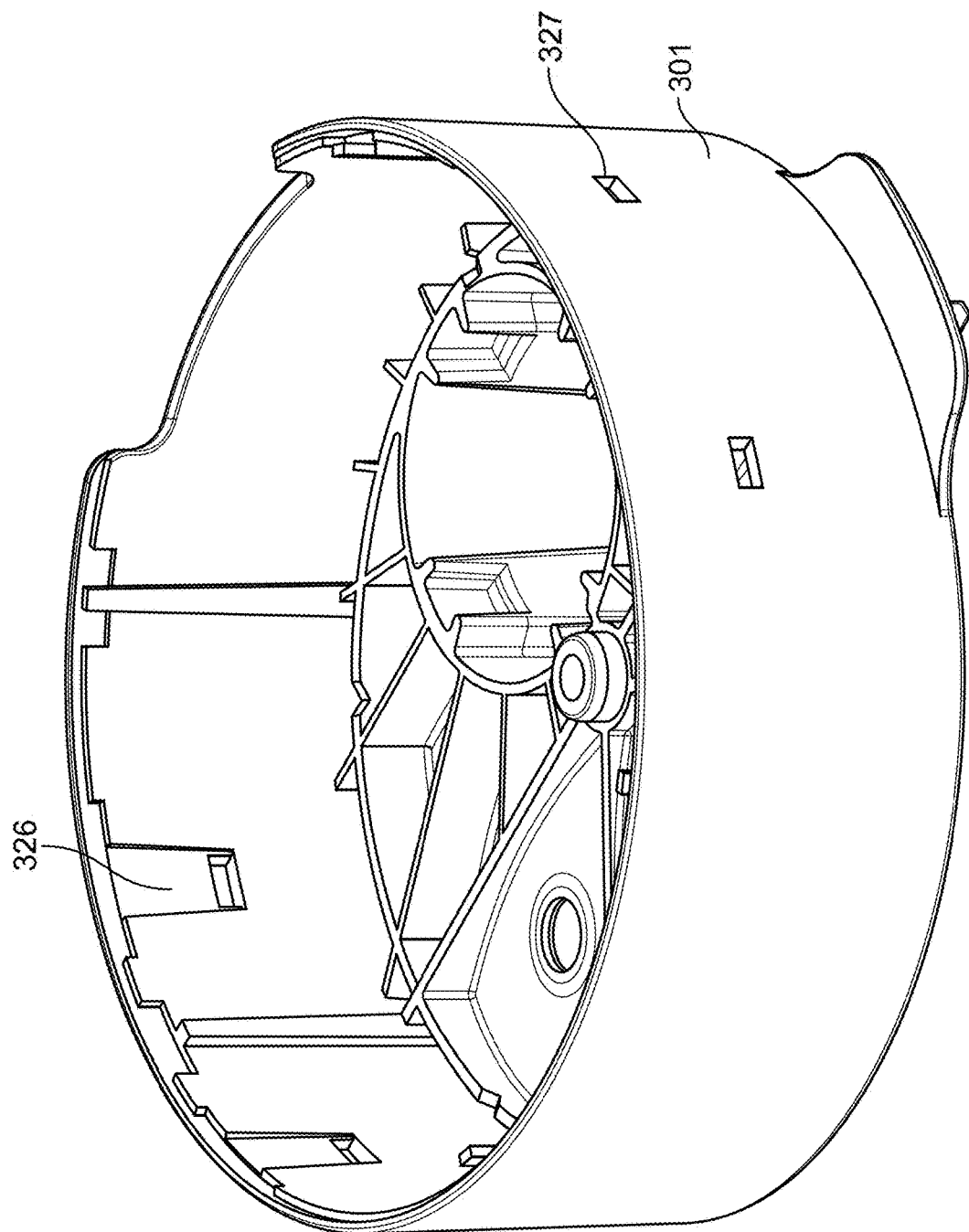
FIG. 3C is a bottom perspective view of a cartridge top cover according to one or more embodiments of the present disclosure.

FIG. 3C generally discloses a bottom perspective view of cartridge top cover 301. In FIG. 3C, a viewer may perceive connection tab cutout 326, each of which in some embodiments may be configured to receive a connection tab 325 and connection tab locking opening 327. In some embodiments, when assembled, each connection tab 325 may slide through connection tab cutout and the terminus of each connection tab 325 may extend through a connection tab locking opening 327, thereby securing cartridge bottom cover 320 to cartridge top cover 301.

Figure 3D:
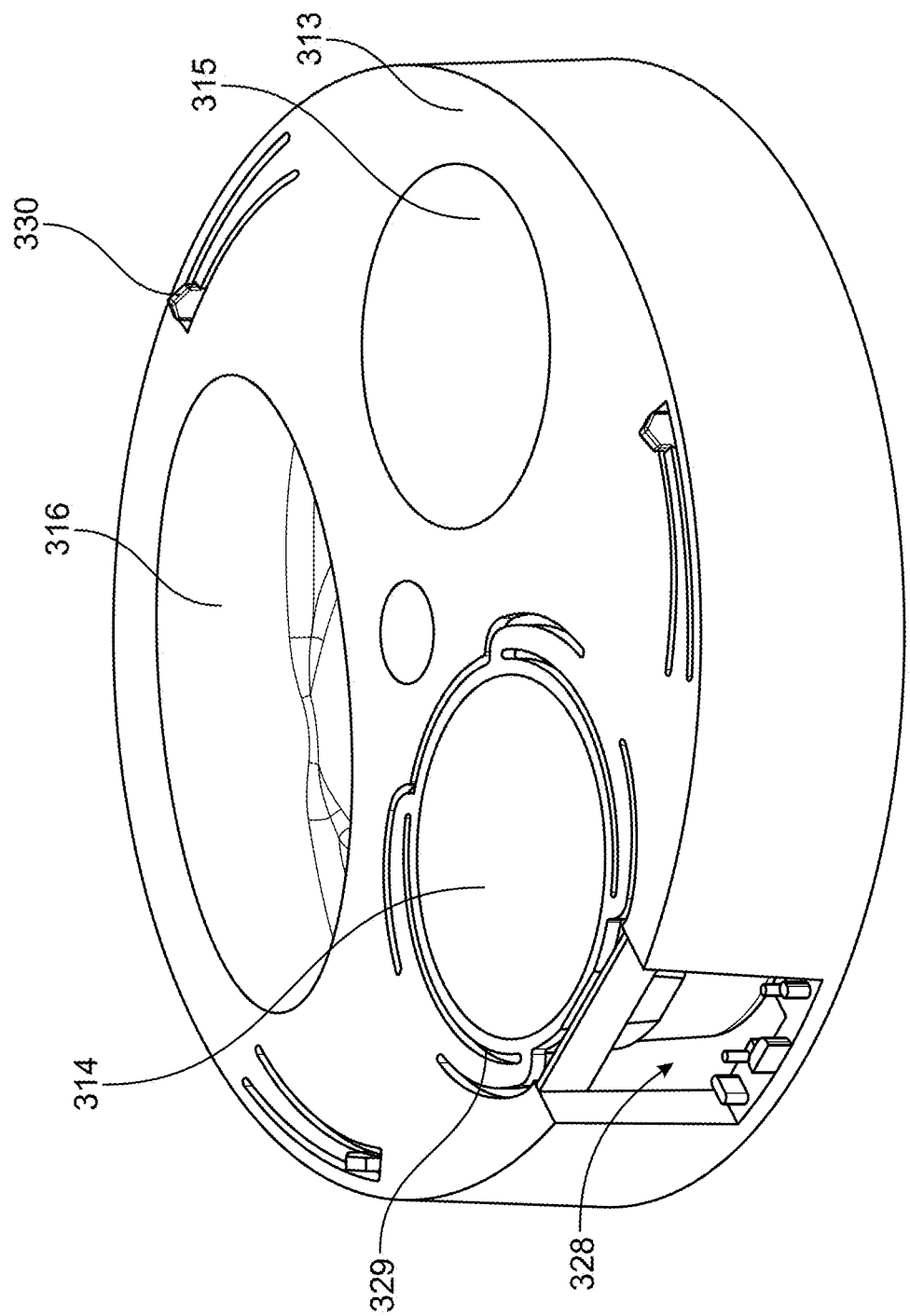
FIG. 3D is a top perspective view of a well plate according to one or more embodiments of the present disclosure.

FIG. 3D generally discloses a top perspective view of well plate 313, along with Well A 314, Well B 315, and Well C 316. In FIG. 3D, a viewer may also perceive component opening 328, raised processing area cutouts 329, and tab stop 330.

Figure 3E:
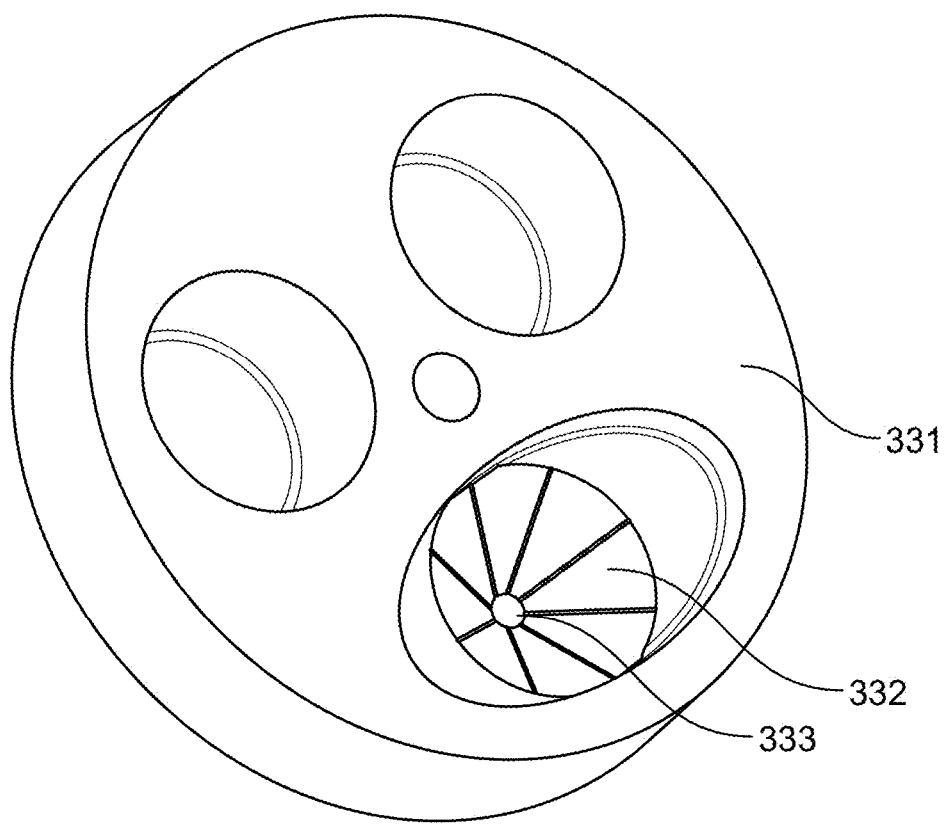
FIG. 3E is a top perspective view of an alternative embodiment of a well plate according to one or more embodiments of the present disclosure.

FIG. 3E generally discloses alternative well plate 331, alternative lower well portion 332, and alternative inner well portion 333. In some embodiments, such as but not limited to embodiments configured to prepare a cell suspension for treatment of smaller areas, the present invention may provide for a smaller Well A 314, Well B 315, or Well C 316, as well as a more conical lower well portion, such as alternative lower well portion 332. Additionally, in some embodiments, the circumference of alternative lower well portion 332 may be smaller than the circumference of the lower well portion shown in FIG. 3A. Accordingly, and by way of non-limiting example, the steeper slope and smaller size of alternative lower well portion 332 may enable the effective processing and collection of smaller skin samples or smaller fluid volumes.

Figure 3F:
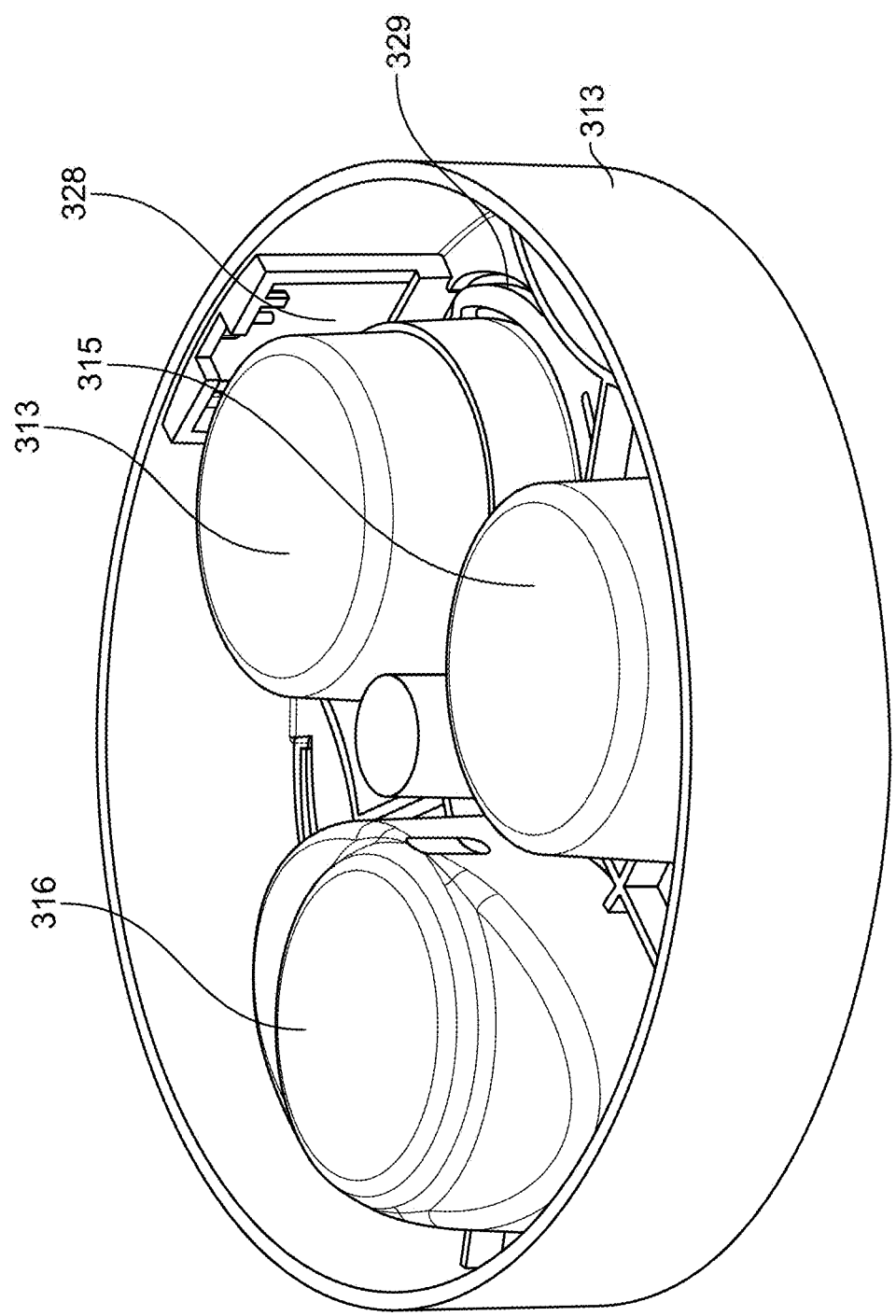
FIG. 3F is a bottom perspective view of a well plate according to one or more embodiments of the present disclosure.

FIG. 3F generally discloses the underside of an embodiment of well plate 313, along with the undersides of Well A 314, Well B 315, and Well C 316 as well as component opening 328 and raised processing area cutouts 329.

Figure 3G:
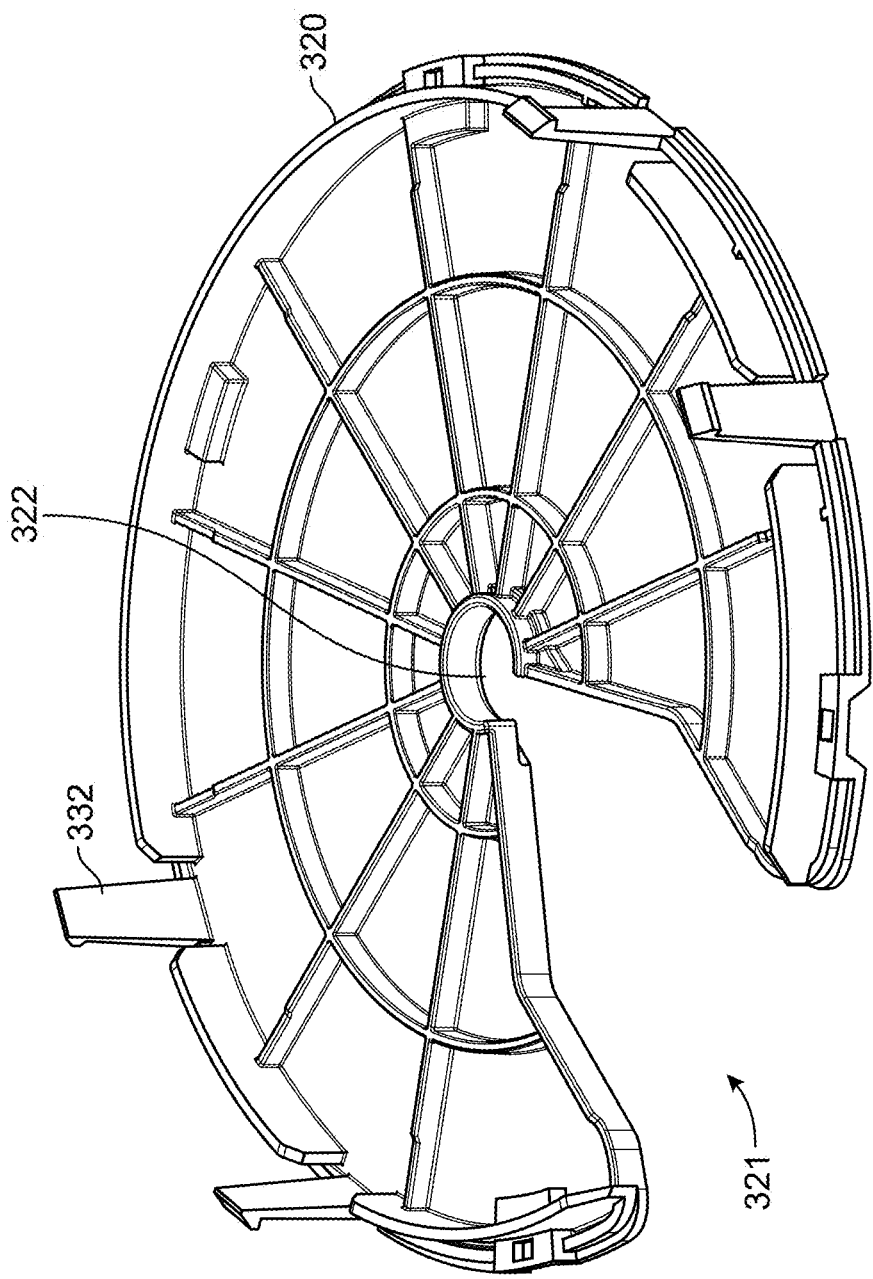
FIG. 3G is a top perspective view of a cartridge bottom cover according to one or more embodiments of the present disclosure.

FIG. 3G generally discloses a top perspective view of cartridge bottom cover 320, connection tabs 323, bottom cover opening 321, and docking spindle opening 322. Although a viewer may perceive that in some embodiments cartridge bottom cover 320 comprises a plurality of raised elements radiating outward from cartridge bottom cover 320 as generally disclosed in FIG. 3G, such a configuration is shown in FIG. 3G for illustration purposes only and other embodiments are contemplated, such as a smooth surface for the top side of cartridge bottom cover 320, a grid pattern for the top side of cartridge bottom cover 320. In some embodiments, a smooth surface for the top side of cartridge bottom cover 320 and the other related elements of cartridge 300 for example cartridge top cover 301 and well plate 313, may comprise an alternative shape, such as a square or a rectangle.

Figure 3H:
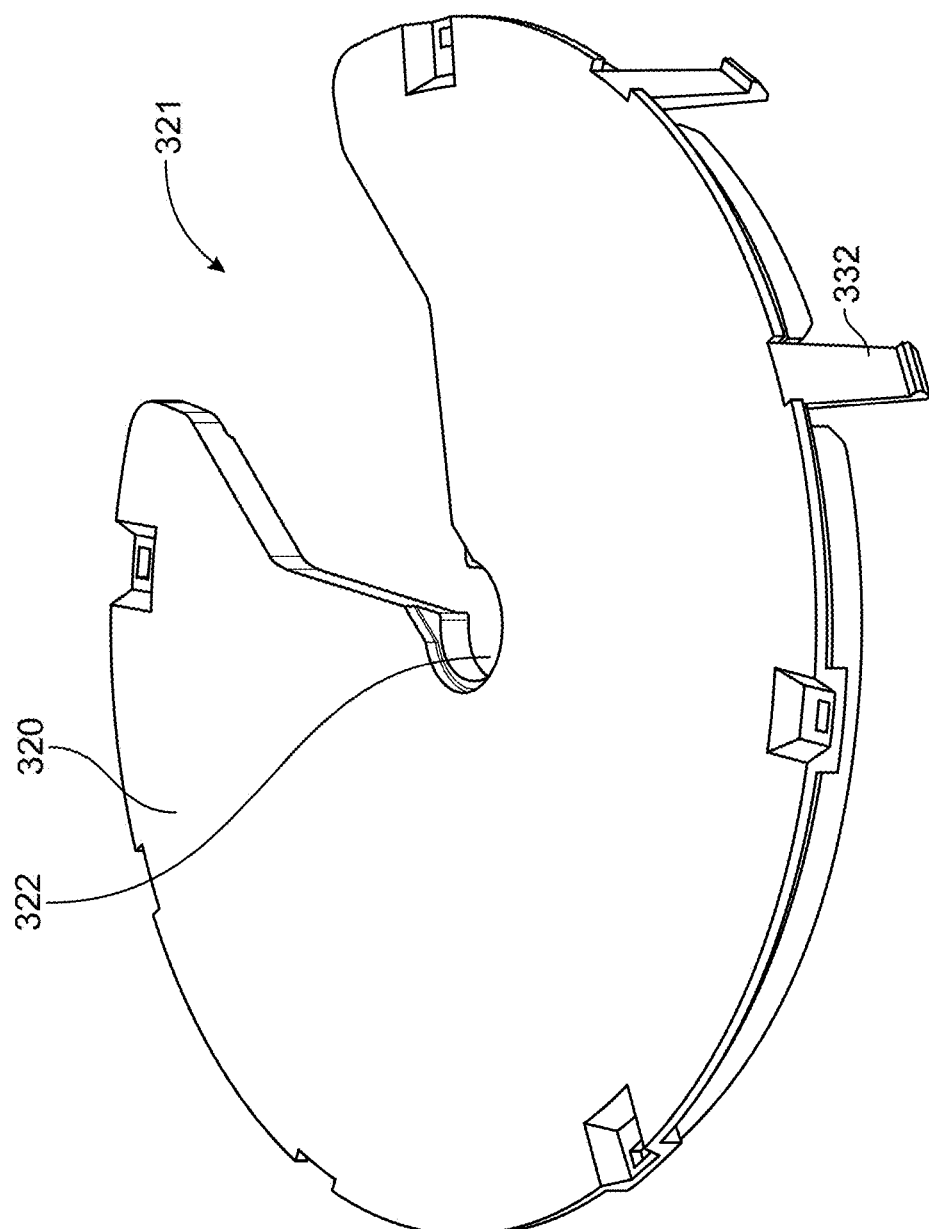
FIG. 3H is a bottom perspective view of a cartridge bottom cover according to one or more embodiments of the present disclosure.

FIG. 3H generally discloses a bottom perspective view of cartridge bottom cover 320, connection tabs 323, bottom cover opening 321, and docking spindle opening 322.

Figure 4:
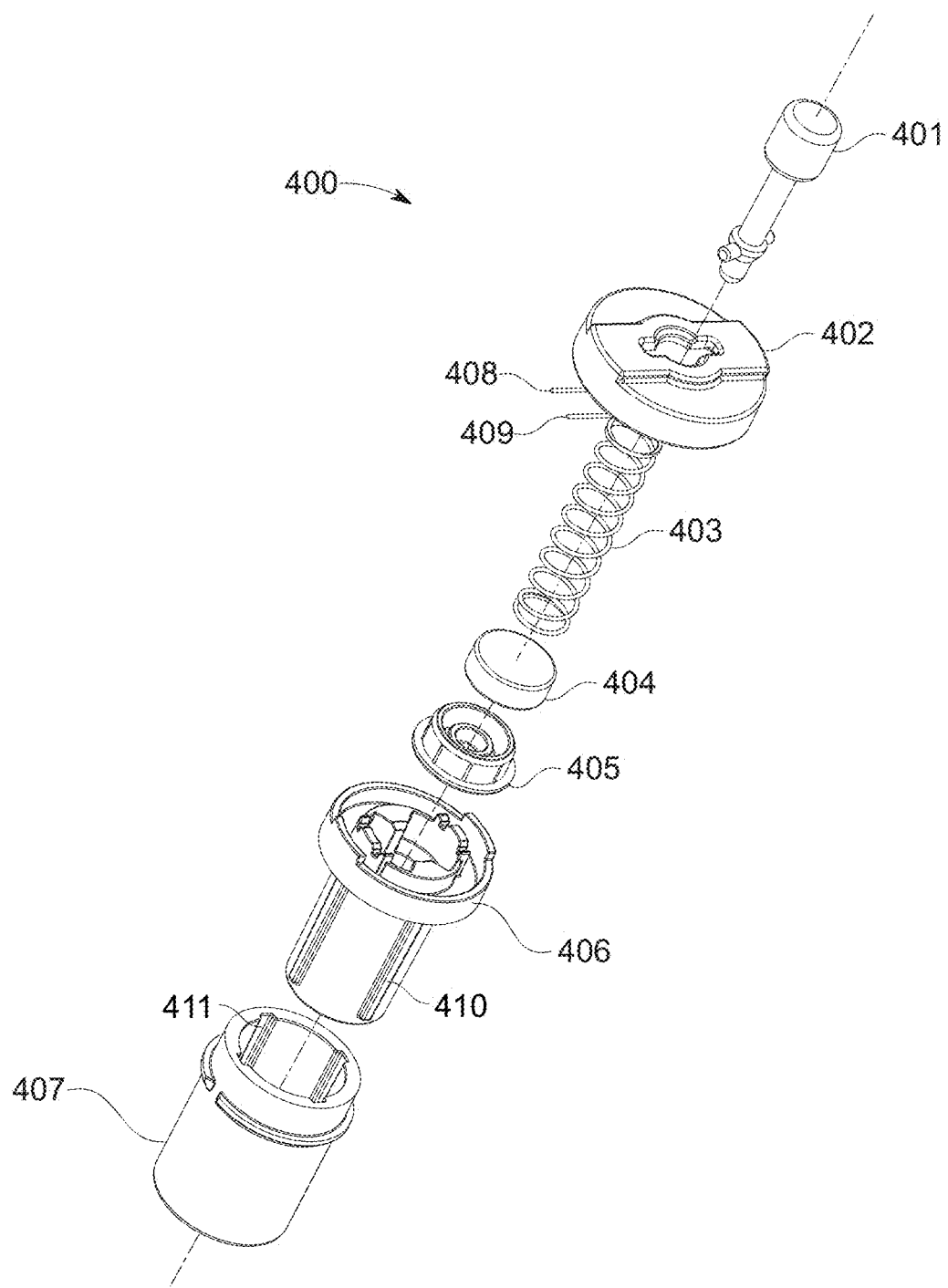
FIG. 4 is an exploded perspective view of a pestle assembly according to one or more embodiments of the present disclosure.

With respect to FIG. 4, the viewer may observe an exploded perspective view of a pestle 400 in accordance with an embodiment of the present disclosure. More specifically, FIG. 4 tends to disclose pestle 400, pestle shaft (or shaft) 401, pestle top cap 402, pestle spring 403, pestle spring cap 404, pestle bottom cap 405, pestle body 406, pestle head 407, pestle retention wire 1 408, pestle retention wire 2 409, pestle body ridge 410, and pestle head interior notches 411.

In some embodiments, pestle 400, may comprise pestle top cap 402, pestle spring 403, pestle spring cap 404, pestle bottom cap 405, pestle body 406, pestle head 407, pestle retention wire 1 408, and pestle retention wire 2 409. In such embodiments, pestle shaft (or shaft) 401 may comprise an element of base unit 200, and pestle 400 may comprise the other elements shown in FIG. 4.

However, in some embodiments, pestle 400 may comprise all of pestle shaft (or shaft) 401, pestle top cap 402, pestle spring 403, pestle spring cap 404, pestle bottom cap 405, pestle body 406, pestle head 407, pestle retention wire 1 408, and pestle retention wire 2 409.

In some embodiments, it is contemplated that one or more elements shown in FIG. 4 may be absent in alternative embodiments of pestle 400. For example, by way of illustration and not limitation, in some embodiments, pestle 400 may comprise simply pestle top cap 402, pestle body 406, and pestle head 407. In some embodiments, pestle 400 may comprise simply pestle top cap 402 and pestle head 407. In other embodiments, pestle 400 may comprise an alternative pestle head 407 having a closed top and a notch in the closed top configured to receive pestle shaft (or shaft) 401.

Similarly, in some embodiments, pestle 400 may comprise pestle top cap 402, pestle spring 403, pestle spring cap 404, pestle bottom cap 405, pestle body 406, and pestle head 407, but not pestle retention wire 1 408, and pestle retention wire 2 409. As well, in some embodiments, pestle 400 may comprise pestle top cap 402, pestle spring cap 404, pestle bottom cap 405, pestle body 406, and pestle head 407, but not pestle spring 403, pestle retention wire 1 408, and pestle retention wire 2 409.

In some embodiments, pestle spring 403 may instead comprise a force sensor, a transducer element, a force transducer, a force measuring sensor, a load sensor, a load cell, a tension force sensor, a compression force sensor, a tensile force sensor, a load pin, a load bearing, a stress sensor, a customized sensor, a pressure sensor, or another comparable element.

In some embodiments, pestle 400 may provide the rotational and/or grinding force on a tissue sample within mortar cup (or cup) 311 and against the sidewalls of mortar cup (or cup) 311, as well as against mortar screen (or screen) 312. As can be seen in more detail in FIG. 5, pestle head 407 may be configured to provide friction surfaces that convey these rotational and grinding forces against the tissue sample. In other embodiments, however, pestle 400 may be configured in different structures suitable for an alternative method of tissue disaggregation. Without limitation, in some embodiments, such tissue disaggregation may be accomplished by means of ultrasonic disaggregation, piezoelectric disaggregation, rotary disaggregation via one or more blades, linear disaggregation via one or more blades, blender, punch-through disaggregation, punch-through disaggregation via a mesh or filter, multi-stage punch-through disaggregation, grating such as via a cheese grater-shaped blade surface, "slap chop" disaggregation, spiral grinding disaggregation such as but not limited to a pestle having raised spiral grooves configured to grind tissue against a mortar wall, string slicer disaggregation, shaver disaggregation, actuation disaggregation such as but not limited to actuation in the presence of microbeads, microbubble disaggregation or cavitation disaggregation, magnetic disaggregation, and electromagnetic disaggregation. In some embodiments, pestle 400 may either be configured differently or substituted with a different assembly suitable for such alternate disaggregation means.

In some embodiments, pestle shaft (or shaft) 401 may mate with pestle top cap 402 in the lock-and-key style generally shown in FIG. 4. In other embodiments, however, and for purposes of illustration and not limitation. Pestle shaft (or shaft) 401 may mate with pestle top cap 402 via magnetic connection mating, Luer locking, snap-fit mating, bayonet-style mating, air hose style quick-connect mating, press-fit mating, "Mix2Vial" mating, and any other form of temporary, reversible, or in some embodiments permanent mating methods known in the relevant art. Relatedly, pestle shaft (or shaft) 401 may generally comprise the key shape disclosed in FIG. 4, or may be shorter, longer, wider, narrower, or may have one or more protrusions useful for connecting with pestle top cap 402. In some embodiments, pestle shaft (or shaft) 401 may comprise a component of housing 201 rather than an element of the pestle 400.

In some embodiments, when pestle shaft (or shaft) 401 inserts through pestle top cap 402, pestle shaft (or shaft) 401 may compress pestle spring 403 against pestle spring cap 404. In turn, such force may cause pestle spring cap 404 to make contact with pestle bottom cap 405, which may then make contact with pestle body 406, which in some embodiments may be in removable mated contact with pestle head 407. In some embodiments, therefore, one or more motors housed within housing 201 may turn, agitate, actuate, or otherwise manipulate pestle 400 by turning, agitating, actuating, or otherwise manipulating pestle shaft (or shaft) 401.

For purposes of illustrating the foregoing, in some embodiments, one or more motors housed within housing 201 may turn pestle shaft (or shaft) 401 such that one or more raised protrusions on one or more sides of pestle shaft (or shaft) 401 may make contact with one or more elements on the underside of pestle top cap 402. In such embodiments, when pestle shaft (or shaft) 401 makes such contact with pestle top cap 402, pestle top cap 402 may turn pestle body 406, which may also then turn pestle head 407. In such embodiments, therefore, when the one or more motors turns pestle shaft (or shaft) 401 within pestle 400, it causes pestle head 407 to generate rotational forces, which when pestle head 407 is in contact with a tissue sample, applies rotational force to the tissue sample.

In addition, in some embodiments, the above-described sequence, wherein one or more motors within housing 201 may be configured to press pestle shaft (or shaft) 401 against pestle spring 403, which then presses against pestle spring cap 404, which then presses against pestle bottom cap 405, which then makes contact with pestle body 406, which may itself already be in mated contact with pestle head 407. In embodiments, when pestle head 407 is in contact with a tissue sample, the foregoing sequence may thereby cause pestle head 407 to apply pressure to the tissue sample, which in some embodiments may be disposed along mortar screen (or screen) 312. In some embodiments, the pestle spring 403 force constant may be adjusted to apply a particular spring force in the pestle spring 403 axis through the pestle body 406 and pestle head 407. Such pressure on the tissue sample may provide a grinding force on the tissue, and when such pressure is applied in combination with one or more turning motions by pestle head 407 against the tissue sample, it may apply both rotational and grinding forces against the tissue sample.

In some embodiments, the sequence described above, wherein one or more motors housed within housing 201 turn pestle head 401 such that pestle shaft (or shaft) 401 makes contact with one or more elements on the underside of pestle top cap 402, and wherein such contact turns pestle top cap 402, which turns pestle body 406, which also then turns pestle head 407, may be useful to raise or lower mortar cup (or cup) 311 within raised processing area 302. In some embodiments, by way of illustration and not limitation, a clockwise turning motion by pestle shaft (or shaft) 401 against pestle top cap 402 may cause mortar cup (or cup) 311 and pestle 400 to raise up onto upper processing area 303 such that one or more tabs on mortar top cap 309, mortar polymer ring 310, or mortar cup (or cup) 311 cause mortar cup (or cup) 311 and pestle 400 to rest on the upper processing area 303, which in some embodiments may enable well plate 313 to rotate Well A 314, Well B 315, or Well C 316 underneath raised processing area 302. In some embodiments, a counterclockwise turning motion by pestle shaft (or shaft) 401 against pestle top cap 402 may cause mortar cup (or cup) 311 and pestle 400 to raise up onto upper processing area 303 such that one or more tabs on mortar top cap 309, mortar polymer ring 310, or mortar cup (or cup) 311 cause mortar cup (or cup) 311 and pestle 400 to rest on the upper processing area 303, which in some embodiments may enable well plate 313 to rotate Well A 314, Well B 315, or Well C 316 underneath raised processing area 302.

In some embodiments, a clockwise turning motion by pestle shaft (or shaft) 401 against pestle top cap 402 may cause mortar cup (or cup) 311 and pestle 400 to lower from upper processing area 303 into one or more of Well A 314, Well B 315, or Well C 316, wherein one or more tissue processing steps may be carried out. In some embodiments, a counterclockwise turning motion by pestle shaft (or shaft) 401 against pestle top cap 402 may cause mortar cup (or cup) 311 and pestle 400 to lower from upper processing area 303 into one or more of Well A 314, Well B 315, or Well C 316, wherein one or more tissue processing steps may be carried out. In certain preferred embodiments, the turning motion applied by pestle shaft (or shaft) 401 against pestle top cap 402 is counterclockwise.

As may be seen in FIG. 4, in some embodiments, pestle 400 may comprise four pestle head interior notches 411, which in some embodiments may correspond to four pestle body ridges 410, disposed on pestle body 406. In some embodiments, pestle 400 may comprise three pestle head interior notches 411, which in some embodiments may correspond to three pestle body ridges 410. In some embodiments, pestle 400 may comprise two pestle head interior notches 411, which in some embodiments may correspond to two pestle body ridges 410. In some embodiments, pestle 400 may comprise one pestle head interior notch 411, which in some embodiments may correspond to one pestle body ridge 410. In some embodiments, pestle 400 may comprise five or more pestle head interior notches 411, which in some embodiments may correspond to five or more pestle body ridges 410.

Figure 5A:
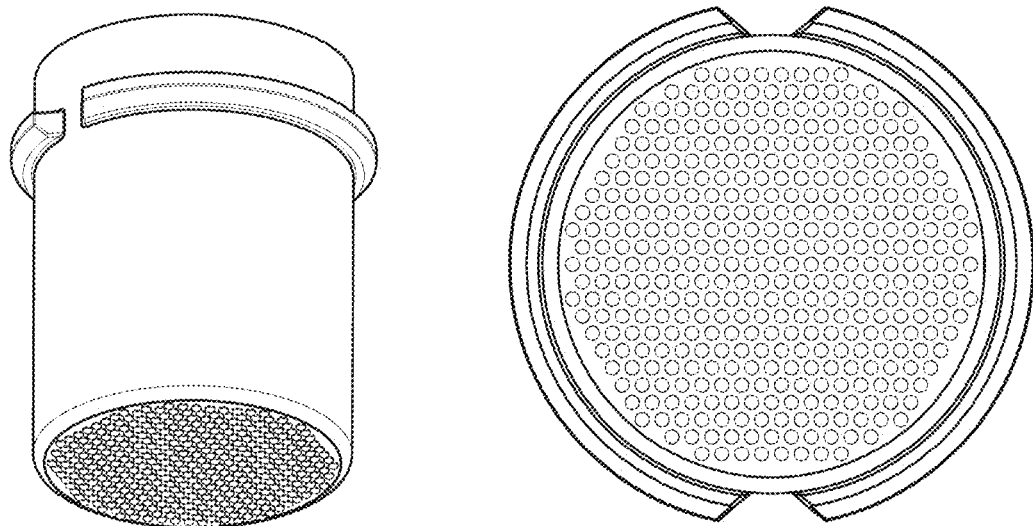
FIGS. 5A-5J generally disclose a series of non-limiting embodiments of a pestle head according to the present disclosure.
Figure 5B:
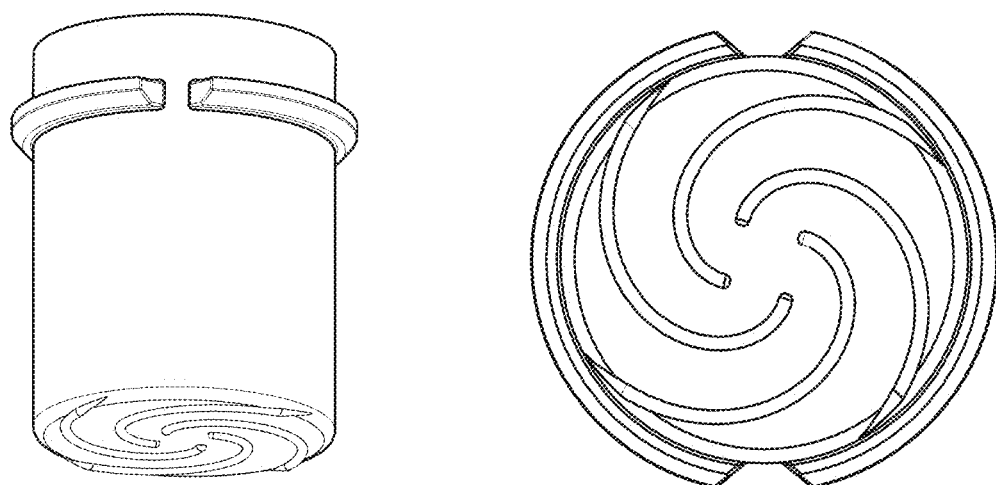

FIGS. 5A-5H illustrate a series of alternative embodiments of a pestle head 407 according to various embodiments of the present disclosure. More specifically, FIG. 5A tends to show a pestle head 407 with a smooth exterior and raised bumps or "pips" on its terminus. FIG. 5B tends to show a pestle head 407 with a smooth exterior and a raised spiral shape on its terminus.

Figure 5C:
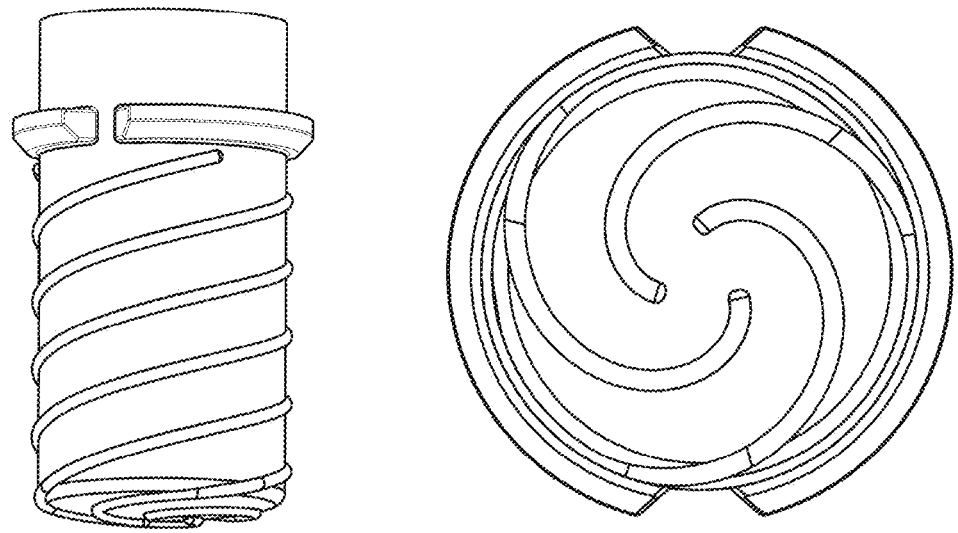
Figure 5D:
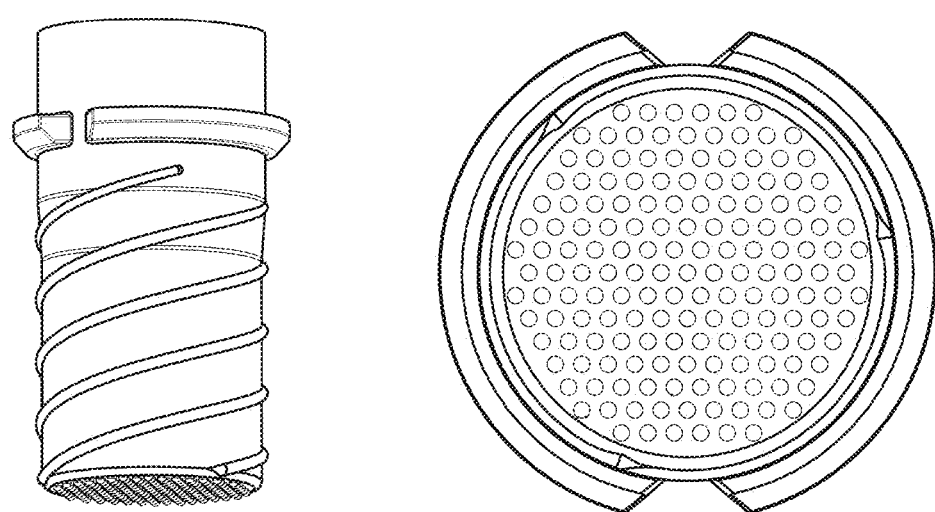
Figure 5E:
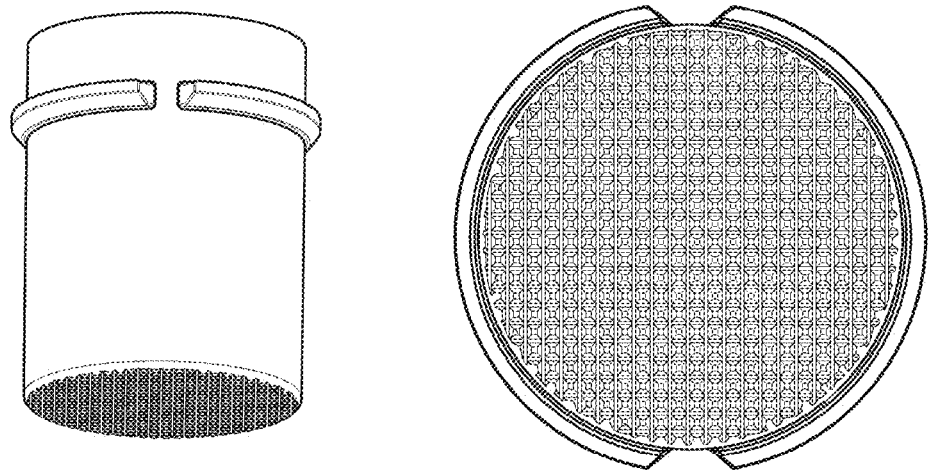
Figure 5F:
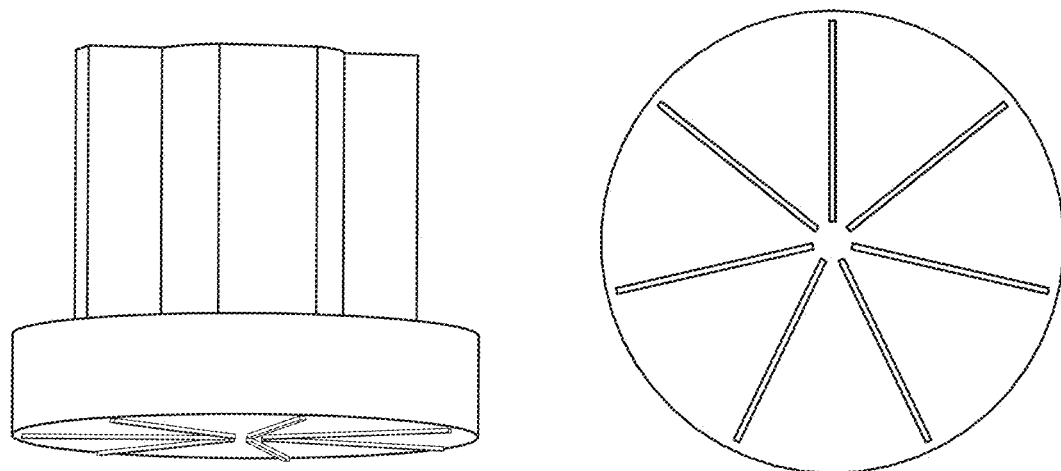

FIG. 5C tends to show a pestle head 407 with a raised spiral pattern on its exterior and a raised spiral shape on its terminus. FIG. 5D tends to show a pestle head 407 with a raised spiral pattern on its exterior and raised bumps or "pips" on its terminus. FIG. 5E tends to show a pestle head 407 with a smooth exterior and a raised waffle pattern on its terminus. FIG. 5F tends to show a pestle head 407 with an exterior comprised of repeating right angles and a raised radiating line pattern on its terminus. In some embodiments, the pestle head 407 may be composed of one or more rubbers such as but not limited to silicone rubber, natural rubber, butadiene rubber, butyl rubber or IIR, ethylene propylene diene monomer or EPM or EPDM, fluoroelastomers or FKM/Viton, isoprene rubber, nitrile rubber or NBR, or styrene butadiene rubber; metals such as but not limited to stainless steel, copper, titanium, cobalt chrome, aluminum, magnesium, gold, platinum, silver, iridium, tantalum; any type of plastic such as but not limited to polycarbonate, polypropylene, acrylonitrile butadiene styrene or ABS, polyethylene, polymethyl methacrylate, polyvinyl chloride or PVC, polyethylene terephthalate glycol or PETG, polylactic Acid PLA, or any combination of such materials or other types of rubber, metal, or plastic known in the art. In some embodiments, the pestle head 407 may be detachable and replaceable.

Figure 5G:
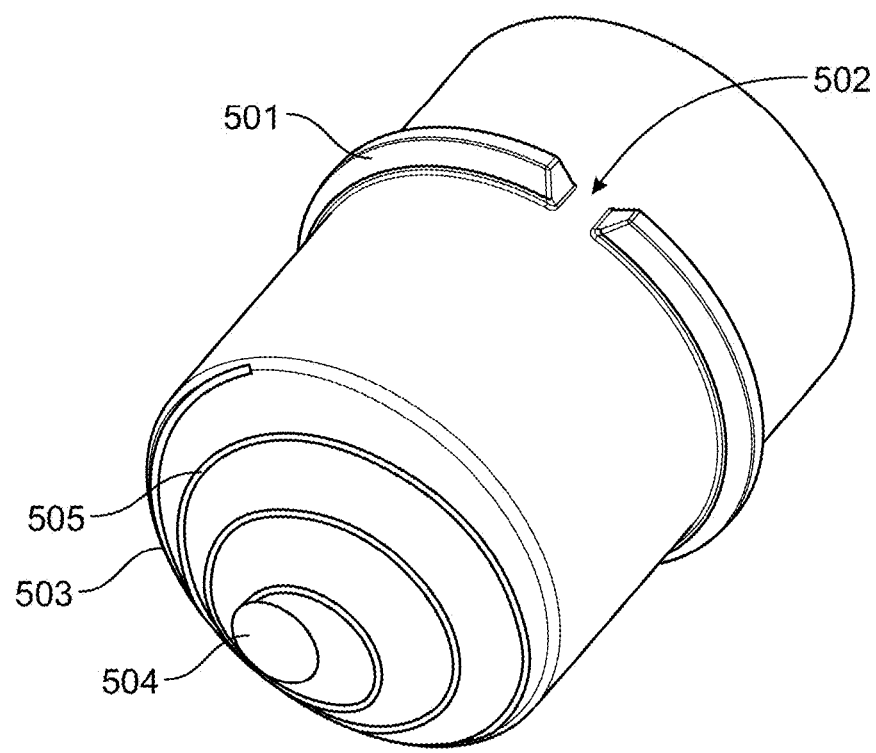
Figure 5H:
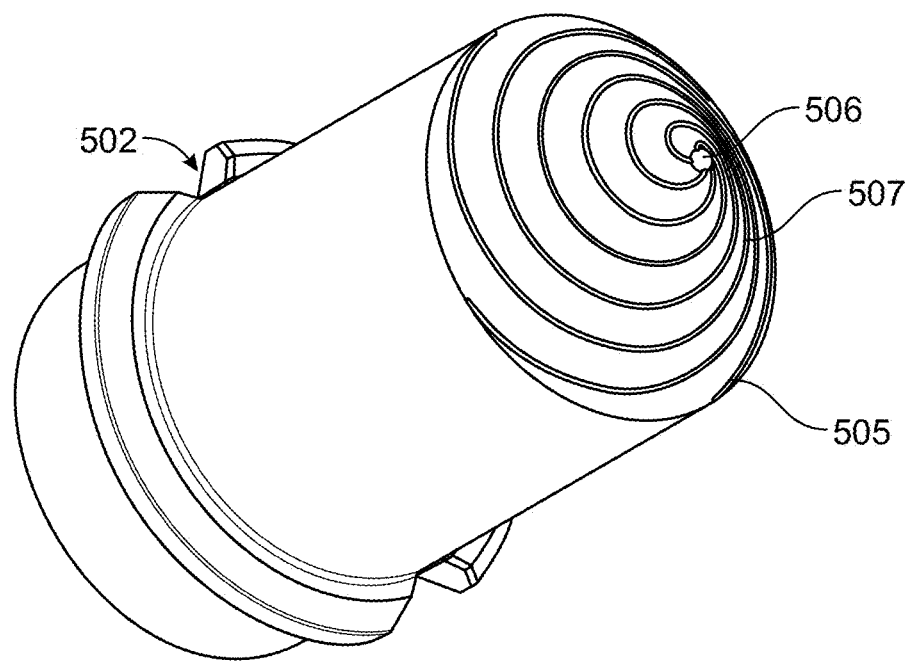

Additionally, FIGS. 5G and 5H generally disclose raised lateral element 501 and raised element opening 502 as well as wide-tapered pestle head 503, narrow-tapered pestle head 505, wide pestle head point 504, narrow pestle head point 506, wide spiral raised groove pattern 505, and narrow spiral raised groove pattern 509. It should be noted that raised lateral element 501 and raised element opening 502 may also be seen in FIGS. 5A-5E.

Figure 7A:
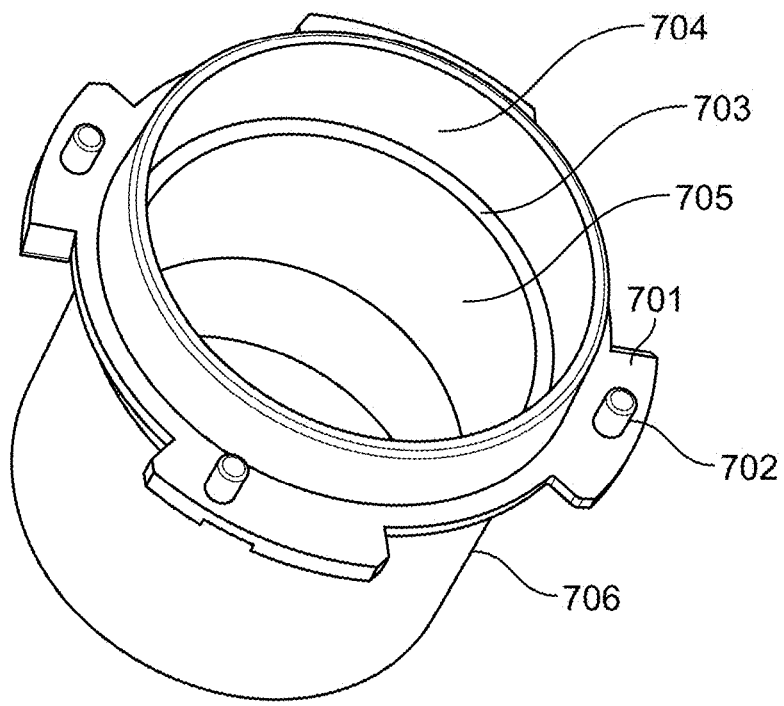
FIGS. 7A-7C generally disclose non-limiting embodiments of the mortar cup (or cup) according to the present disclosure.
Figure 8A:
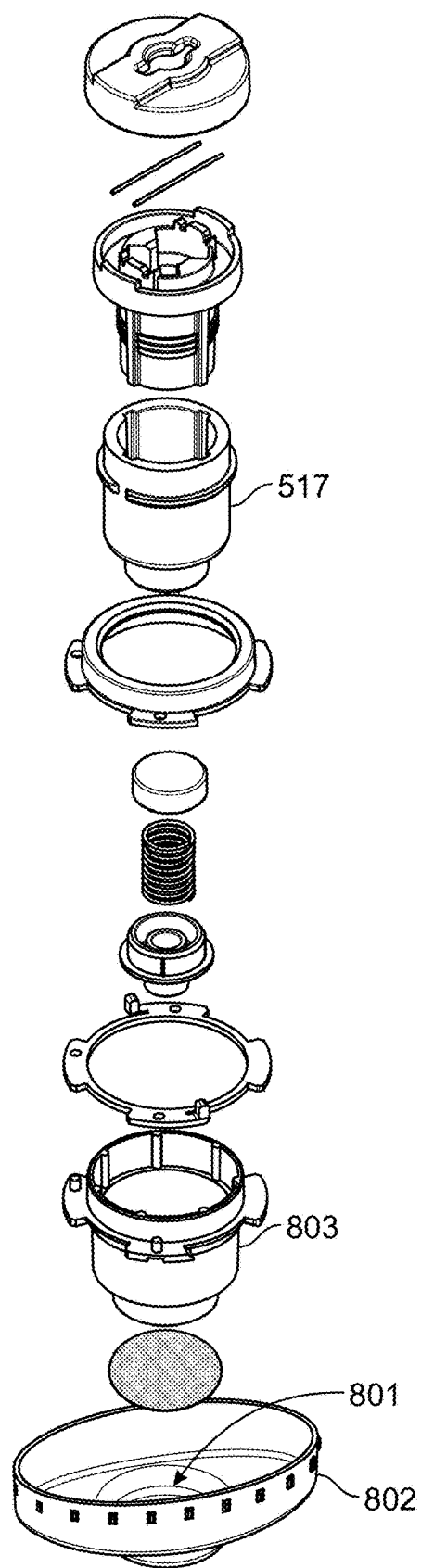
FIG. 8A generally discloses an inset pestle, inset mortar cup (or cup), and inset Well C combination.
Figure 8B:
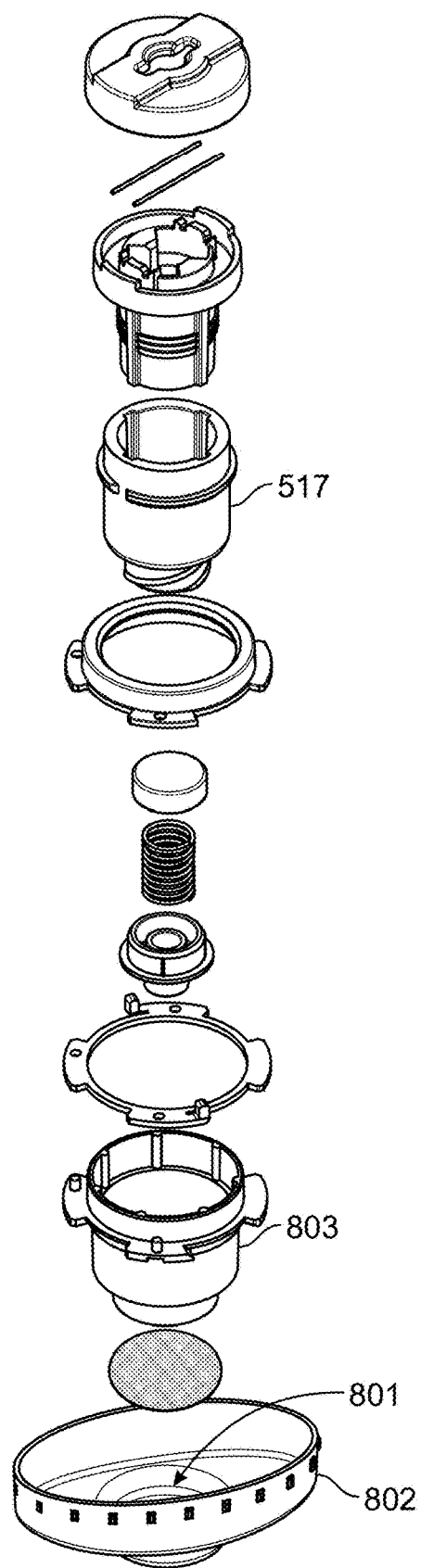
FIG. 8B generally discloses an alternative inset pestle, inset mortar cup (or cup), and inset Well C combination.

It is contemplated that, in some embodiments, wide-tapered pestle head 504 or narrow-tapered pestle head 505 may be paired with tapered mortar cup (or cup) 801, which may be observed in FIG. 8B. Relatedly, wide-tapered pestle head 504 or narrow-tapered pestle head 505, together with tapered mortar cup (or cup) 801, may be configured for use with alternative lower well portion 702 as generally disclosed in FIG. 7A. Moreover, wide-tapered pestle head 504 or narrow-tapered pestle head 505 may in some embodiments comprise any of the raised elements disclosed in FIGS. 5A-5F in addition to or in combination with wide spiral raised groove pattern 508 or narrow spiral raised groove pattern 509.

As may be apparent by observing FIGS. 5A-5E and FIGS. 5G-5H, in some embodiments, two raised lateral elements 501 may generally form a ring around pestle head 407, separated by one or more raised element openings 502. In some embodiments, the ring shape may comprise a single-opening ring wherein a single raised lateral element 501 comprises a single raised element opening 502 disposed along it. In some embodiments, a two-opening ring shape may comprise two raised lateral elements 501 separated by two raised element openings 502. In some embodiments, the ring shape may comprise three or more raised lateral elements 501 separated by three or more raised element openings 502.

In some embodiments, two or more raised lateral elements 501 may be disposed along pestle head 407 in any order, such as but not limited to a staggered order. Accordingly, and by way of illustration, two ring-shaped arrangements comprising one or more raised lateral elements 501 separated by one or more raised element openings 502 may be disposed along pestle head 407, one above the other. In some such embodiments, the raised element openings 502 may be aligned with one another relative to the long axis of pestle head 407, or in some embodiments they may be staggered or in any order relative to each other and the long axis of pestle head 407.

Those of skill in the art will also appreciate that in some embodiments, raised lateral element 501 may be wider, narrower, taller, or shorter than shown in FIGS. 5A-5E and FIGS. 5G-5H. As well, in some embodiments, raised element openings 502 may not be tapered. In variations comprising two or more raised element openings 502, some raised element openings 502 may be tapered while other raised element openings 502 are not tapered. In embodiments comprising more than one raised element opening 502, the raised element openings may be aligned vertically along pestle cap 407, may be staggered or otherwise not aligned relative to pestle cap 407, or some raised element openings 502 may be aligned with each other and some raised element openings 502 may not be aligned with each other, relative to pestle cap 407.

In some embodiments, such as those generally shown in FIGS. 5A-5E and FIGS. 5G-5H, two or more raised lateral elements 501, may have one or more openings. In some such embodiments, again such as the illustrative and non-limiting embodiments generally disclosed in FIGS. 5A-5E and FIGS. 5G-5H, the raised ring element may taper to a point on either side of the one or more openings. In preferred embodiments, the raised element may comprise a raised ring comprising two openings, wherein the raised ring element may taper to a point on either side of the one or more openings.

Furthermore, it is contemplated that in some embodiments, the raised lateral element generally disclosed in FIGS. 5A-5E and FIGS. 5G-5H, which in some embodiments may further comprise one or more openings, may be configured such that, when pestle head 407 is inserted into mortar cup (or cup) 311 past interior ridge 803, friction between pestle head 407 and the interior of mortar cup (or cup) 311 may enable pestle 400, via said friction, to raise mortar cup (or cup) 311 and to otherwise manipulate mortar cup (or cup) 311, such as but not limited to lowering mortar cup (or cup) 311 at a controlled or intended rate, rotating mortar cup (or cup) 311, or otherwise actuating or moving mortar cup (or cup) 311.

Figure 5I:
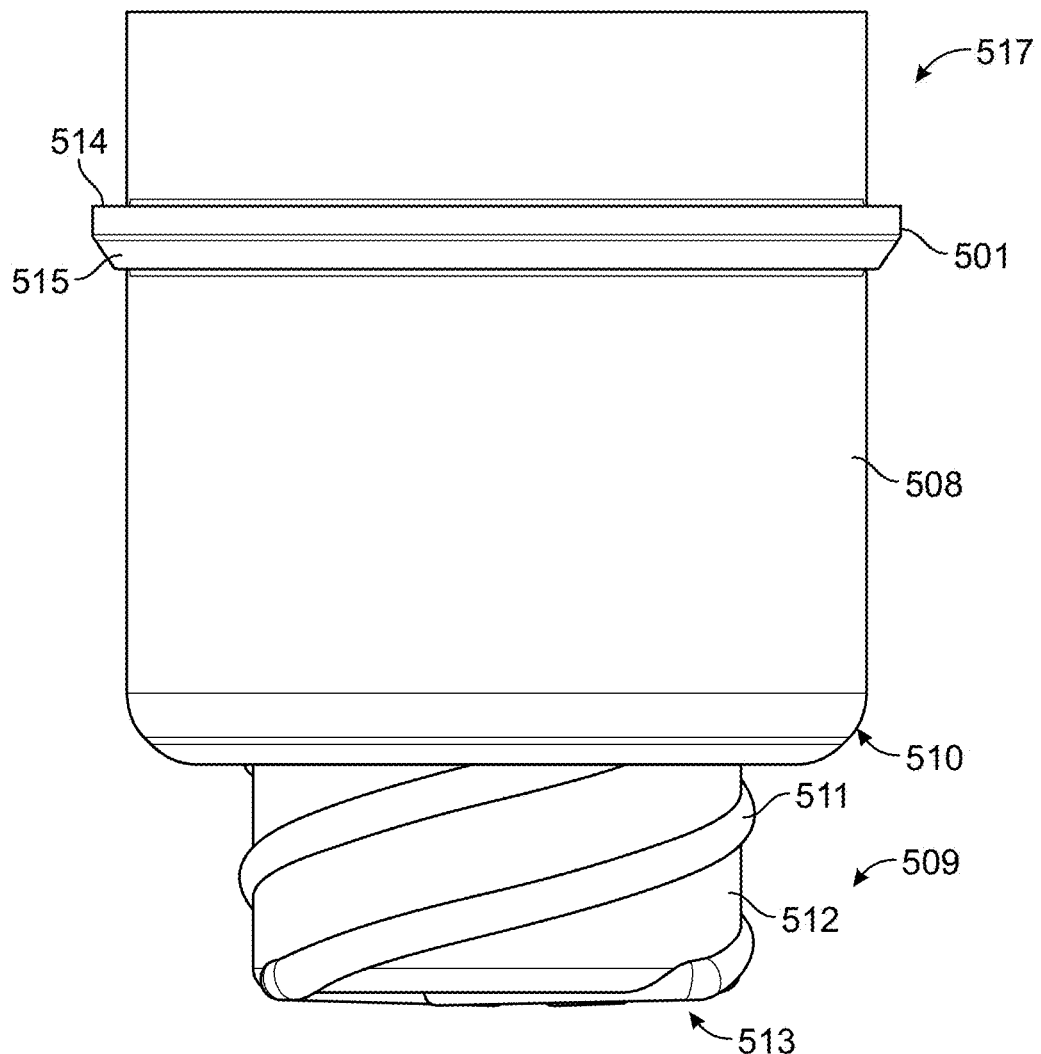

FIG. 5I generally discloses an inset pestle head 517 having an inset terminus 509 with raised spiral elements 511 on the exterior of the inset terminus 509. In such embodiments, inset terminus 509 may comprise a cylinder having a smaller diameter than pestle head cylinder 508. In some embodiments, transition terminus 501 may comprise a sloped or curved edge between inset terminus 509 and pestle head cylinder 508.

FIG. 5I also generally discloses a different angle on raised lateral element 501. As may be seen in FIG. 5I, raised lateral element 501 may comprise a flat top edge 514 and tapered lower edge 515. In some embodiments, raised lateral element 501 may be configured to enable pestle head 407 to enter the interior of mortar cup (or cup) 311 but to be prevented from exiting the interior of mortar cup (or cup) 311. In such embodiments, tapered lower edge 515 may enable pestle head 407 to push past mortar top cap 309, mortar polymer ring 310, or both mortar top cap 309 and mortar polymer ring 310, to enter the interior of mortar cup (or cup) 311, but flat top edge 514 may prevent pestle head 407 from exiting the interior of mortar cup (or cup) 311 because flat top edge 514 may catch on mortar top cap 309, mortar polymer ring 310, or both mortar top cap 309 and mortar polymer ring 310. In some embodiments, raised lateral element 501 and its flat top edge 514 and/or tapered lower edge 515 may perform the same function for wide-tapered pestle cap head 503, narrow-tapered pestle cap head 505, inset pestle head 517, a conical pestle head, and any other pestle head described or contemplated in the present disclosure. FIG. 5I also generally discloses raised spiral elements 511 and spiral interstices 512, along with inset terminus distal edge 513. In some embodiments, when inset pestle head 517 is rotated within a corresponding inset mortar cup (or cup) 710, such as may be seen in FIG. 8A, FIG. 8B, and elsewhere herein, raised spiral elements 511 may grind tissue against an interior sidewall of inset mortar cup (or cup) 710. In some embodiments, such tissue in solution may collect in one or more spiral interstices 512 or may be circulated within inset mortar cup (or cup) 710.

Figure 5J:
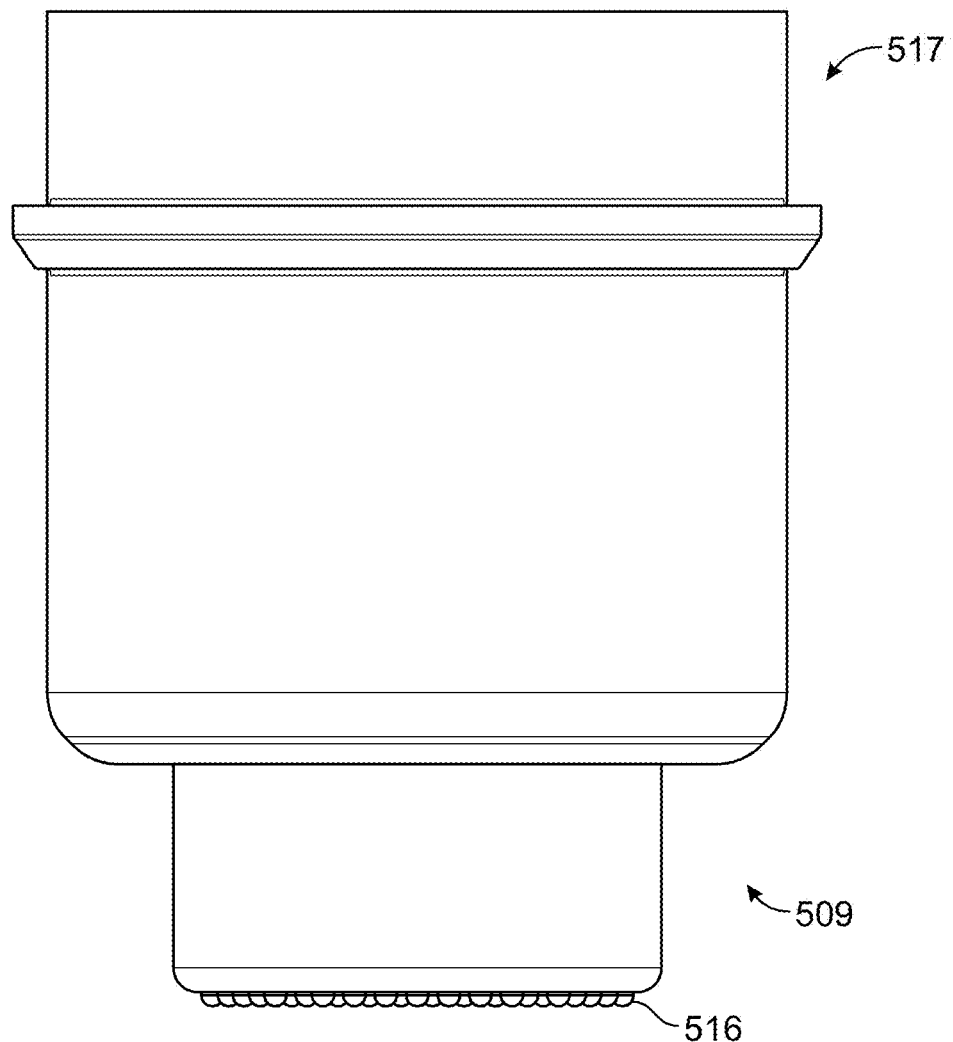

FIG. 5J generally discloses an embodiment of inset pestle head 517 having an inset terminus 509 and a plurality of pips 516 disposed along the distal end of having an inset terminus 509. Although the exterior of inset terminus 509 in some embodiments may be generally smooth as shown in FIG. 5J, in alternative embodiments, the exterior of inset terminus 509 may comprise raised spiral elements 511 and corresponding spiral interstices 512, additional pips, vertical raised elements, horizontal raised elements, diagonal raised elements, recessed portions, outward-extending elements, and other such elements.

Figure 6:
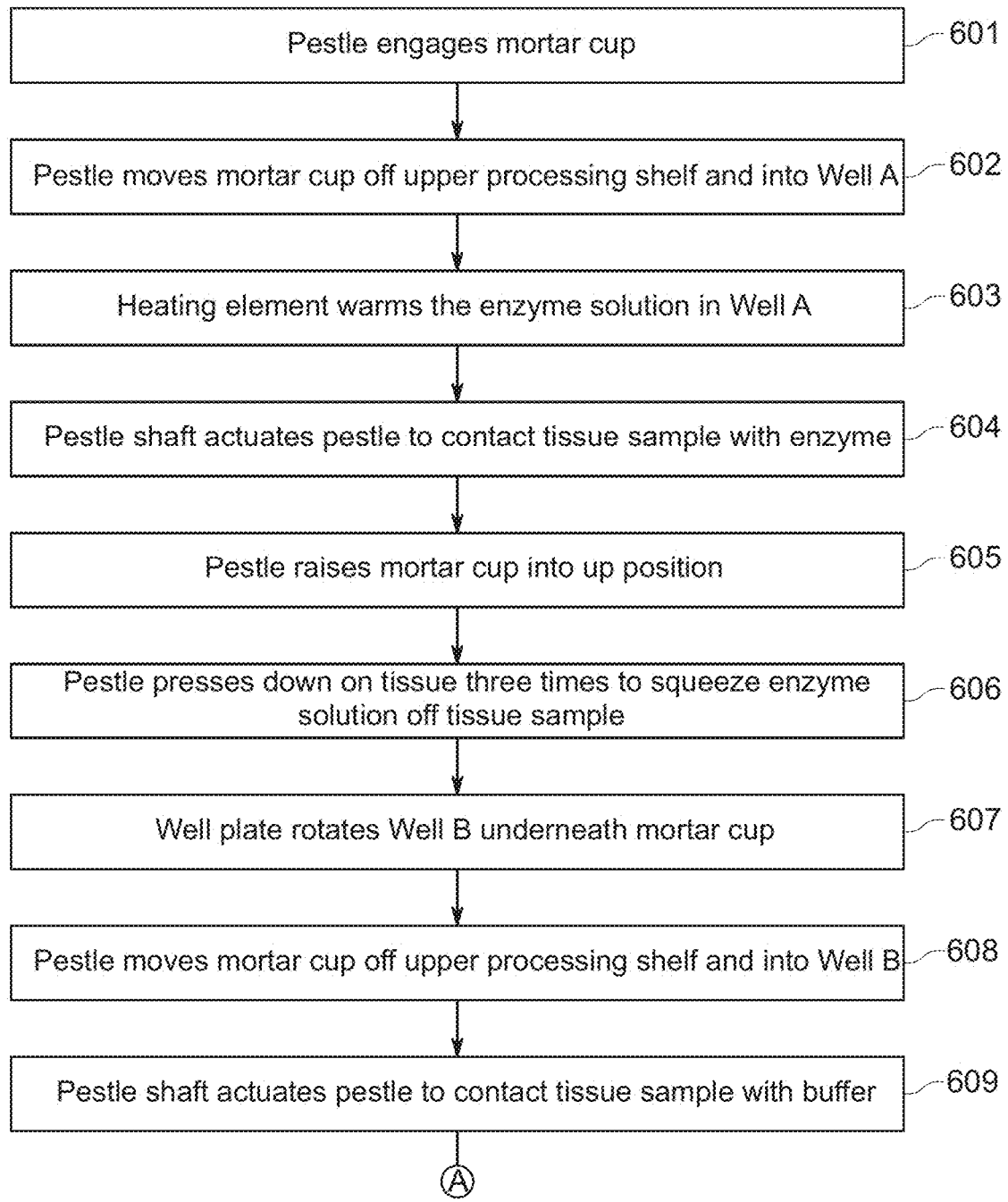
FIG. 6 is a flowchart illustrating an automation sequence and related structural components according to one or more embodiments of the present disclosure.
Figure 6:
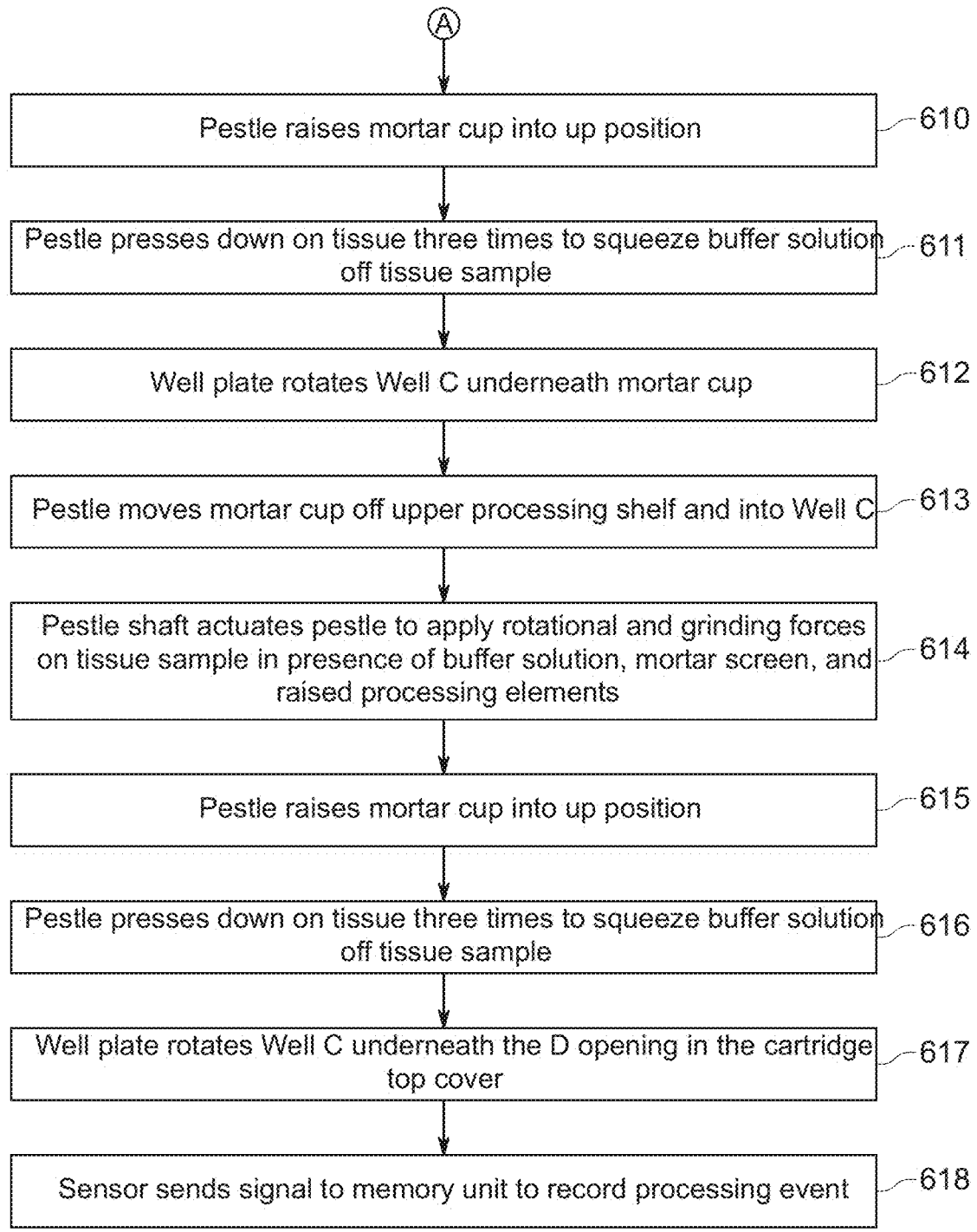

FIG. 6 comprises a flowchart tending to show a processing sequence of a system for automated preparation of a regenerative epidermal suspension according to at least one embodiment of the present disclosure. In some embodiments, one or more elements of the processing sequence disclosed in FIG. 6, or one or more sequences described elsewhere herein, may be omitted or performed in a different sequence.

After turning power on to the system for automated preparation of a regenerative epidermal suspension and initiating the processing sequence, the system may first cause the pestle to engage the mortar cup (or cup) 601. Then, the system may cause the pestle to move the mortar cup (or cup) off the upper processing shelf and into Well A 602. Next, the heating element may warm the enzyme solution in Well A 603. Next, the system may cause the pestle shaft (or shaft) to actuate the pestle such that the pestle causes the tissue sample to come into contact with the enzyme solution 604. Next, the system may cause the pestle to raise the mortar cup (or cup) into an "up" position 605. Next, the system may cause the pestle to press down on the tissue sample three times to squeeze the enzyme solution off tissue sample 606. Next, the system may rotate the well plate such that Well B moves to a position underneath the mortar cup (or cup) 607. Next, the system may cause the pestle to move the mortar cup (or cup) off the upper processing shelf and into Well B 608. Next, the system may cause the pestle shaft (or shaft) to actuate the pestle such that the pestle causes the tissue sample to come into contact with a first quantity of buffer solution 609. Next, the system may cause the pestle to raise the mortar cup (or cup) into the "up" position 610. Next, the system may cause the pestle to press down on the tissue sample three times to squeeze the buffer solution off the tissue sample 611. Next, the system may rotate the well plate such that Well C is moved to a position underneath the mortar cup (or cup) 612. Next, the system may cause the pestle to move the mortar cup (or cup) off the upper processing shelf and into Well C 613. Next, the system may cause the pestle shaft (or shaft) to actuate the pestle so as to apply rotational and grinding forces on the tissue sample in presence of a second quantity of buffer solution, a mortar screen (or screen), and raised processing elements 614. Next, the system may cause the pestle to raise the mortar cup (or cup) into the "up" position 615. Next, the system may cause the pestle to press down on the tissue sample three times to squeeze the buffer solution off the tissue sample 616. Next, the system may rotate the well plate such that Well C is moved underneath the D opening in the cartridge top cover 617. Next, the sensor may send a signal to the memory unit to record the just-completed processing event 618.

In some embodiments, at element 614, the system may alternatively cause the pestle shaft (or shaft) to actuate the pestle so as to apply linear force in addition to or in place of rotational and grinding forces on the tissue sample in presence of a second quantity of buffer solution, a mortar screen (or screen), and raised processing elements 614. As well, at element 614, in some embodiments the system may cause the pestle to apply linear, rotational, or grinding force, or a combination thereof, to the tissue sample without the presence of the mortar screen (or screen). Similarly, at element 614, in some embodiments the system may cause the pestle to apply linear, rotational, or grinding force, or a combination thereof, to the tissue sample without the presence of the raised processing elements.

Additionally, in some embodiments, the nomenclature for the wells and openings recited in the processing sequence disclosed in FIG. 6 may comprise one or more numbers, one or more symbols, one or more raised features, or a combination thereof.

Figure 7B:
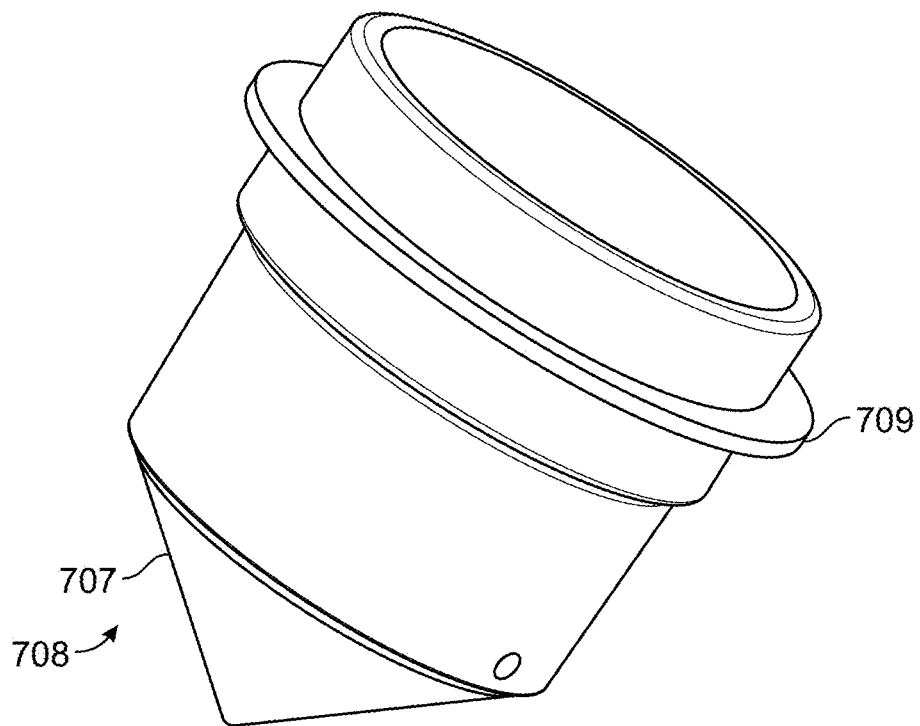

FIG. 7A and FIG. 7B generally disclose embodiments of a mortar cup (or cup) according to embodiments of the present disclosure. More specifically, with respect to FIG. 7A, attention is drawn to tab 701, tab post 702, interior ridge 703, upper mortar portion 704, lower mortar portion 705, and inter-tab notch 706. With respect to FIG. 7B, attention is drawn to conical mortar screen (or screen) 707, tapered mortar cup (or cup) design 708, and mortar cup (or cup) ring 709.

As may be discerned by observing FIG. 7A, upper mortar portion 704 may comprise a wider diameter than lower mortar portion 705, with interior ridge 703 comprising a transition surface between upper mortar portion 704 and lower mortar portion 705. As described elsewhere, in some embodiments, pestle 400 may insert into mortar cup (or cup) 311 such that raised lateral elements 501 on pestle head 407 pass through upper mortar portion 704, press across interior ridge 703, and removably mate with lower mortar portion 705 via friction. In such embodiments, the pressure and friction from raised lateral elements 501 against the surface of lower mortar portion 705 may enable the pestle to lift mortar cup (or cup) 311 during one or more processing events or steps disclosed herein. In other embodiments, raised lateral elements 501 may pass through upper mortar portion 704, press across interior ridge 703, and press against lower mortar portion 705, but may be prevented from exiting mortar cup (or cup) 311 by mortar top cap 309, mortar polymer ring 310, or both mortar top cap 309 and mortar polymer ring 310.

Figure 7C:
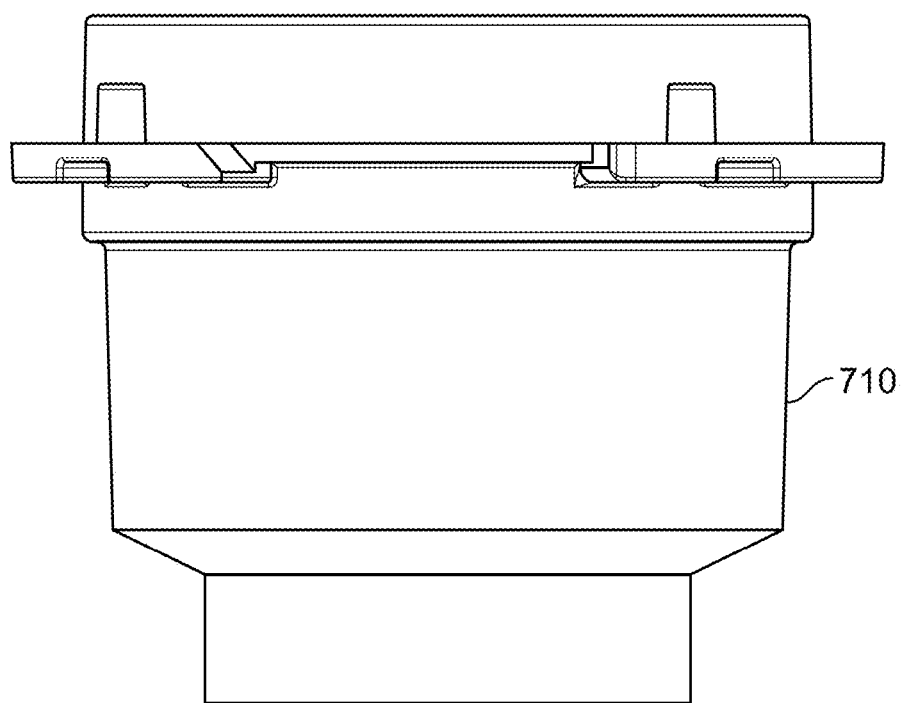

FIG. 7C shows a side planar view of inset mortar cup (or cup) 710.

FIG. 8A generally discloses an embodiment of a pestle, mortar cup (or cup), and Well C combination comprising pestle 400 with inset pestle head 517 inset mortar cup (or cup) 710 and inset Well C 802 having inset lower well portion 801. FIG. 8B generally discloses an alternative embodiment of a pestle, mortar cup (or cup), and Well C combination comprising pestle 400 with inset pestle head 517 inset mortar cup (or cup) 710 and inset Well C 802 having inset lower well portion 801.

Figure 9A:
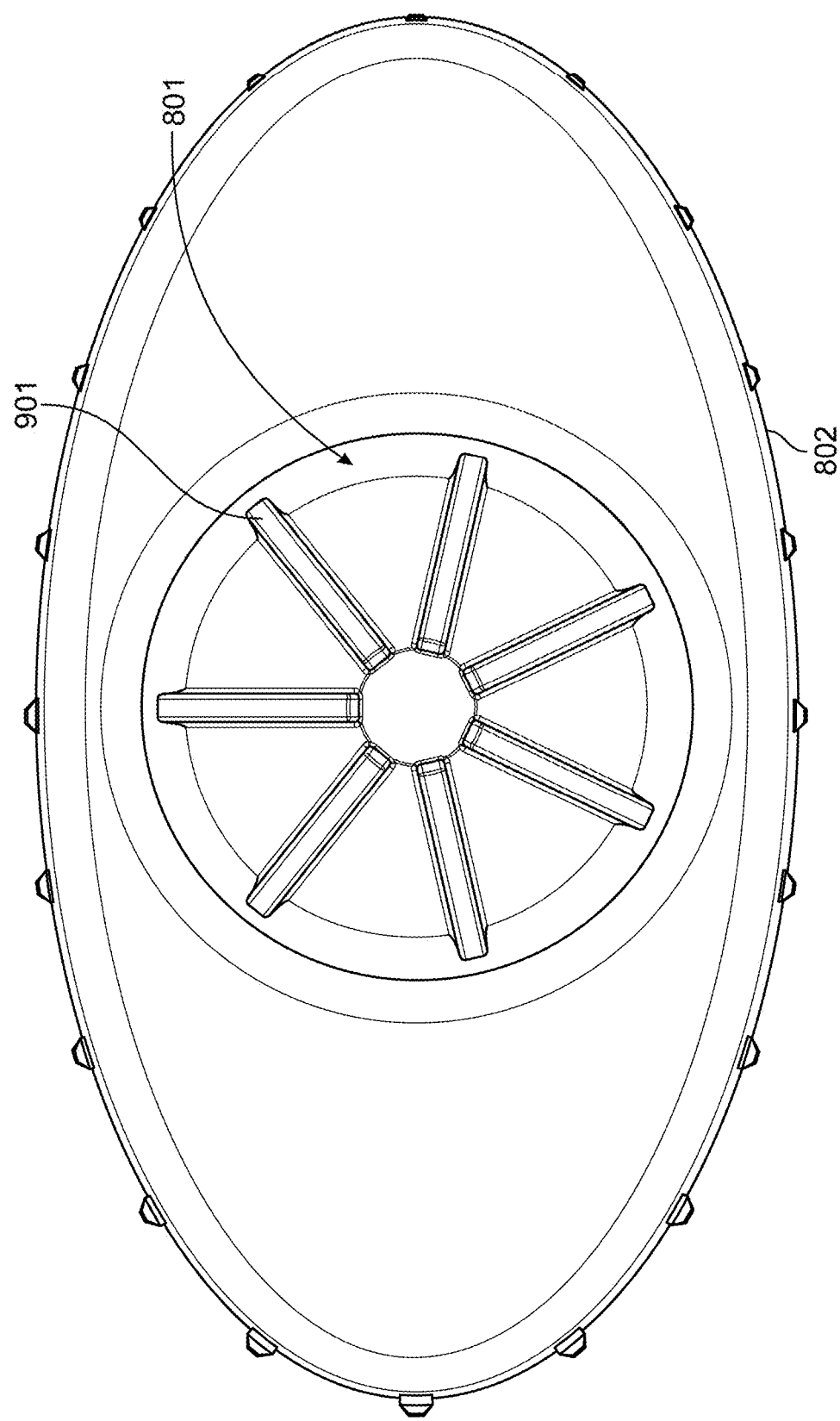
FIG. 9A is a top planar view of an inset Well C with a first embodiment of raised processing elements.

FIG. 9A shows a top planar view of inset Well C 802 having inset lower well portion 801, along with tall raised processing elements 901.

Figure 9B:
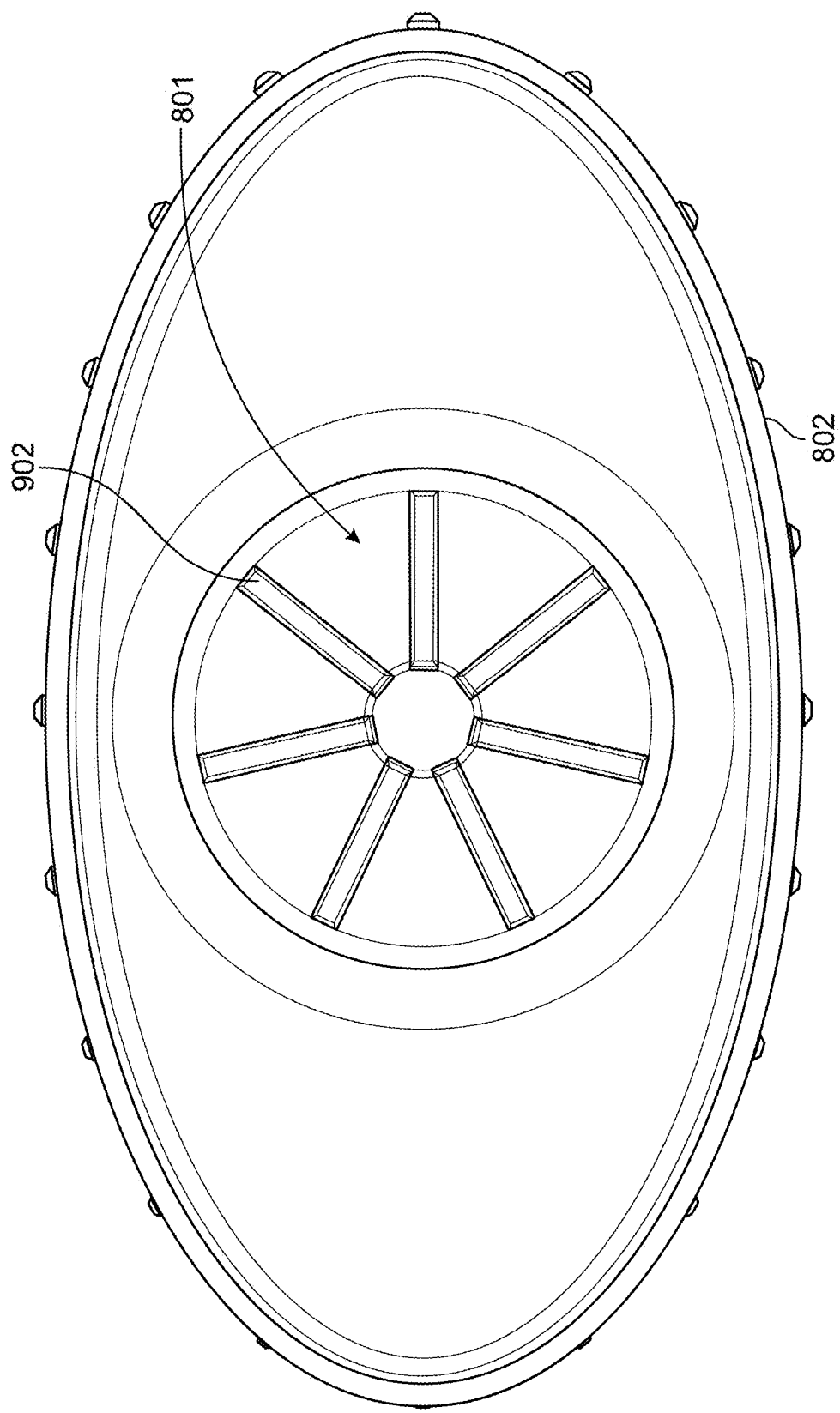
FIG. 9B is a top planar view of an inset Well C with a second embodiment of raised processing elements.

FIG. 9B shows a top planar view of inset Well C 802 having inset lower well portion 801, along with short raised processing elements 902.

Figure 9C:
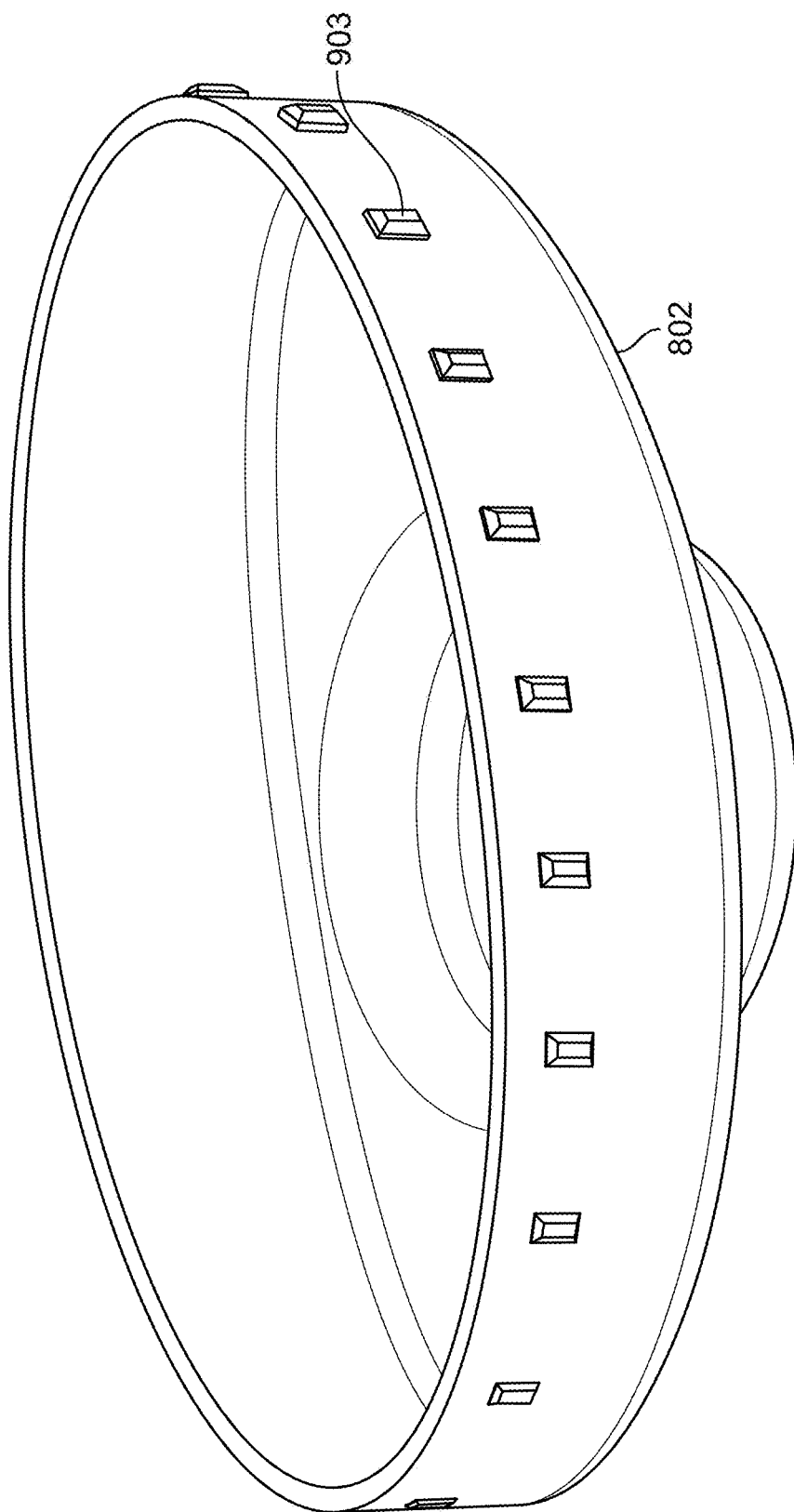
FIG. 9C is a side perspective view of an inset Well C.

FIG. 9C shows a side perspective view of inset Well C 802 and side protrusions 903.

Figure 10A:
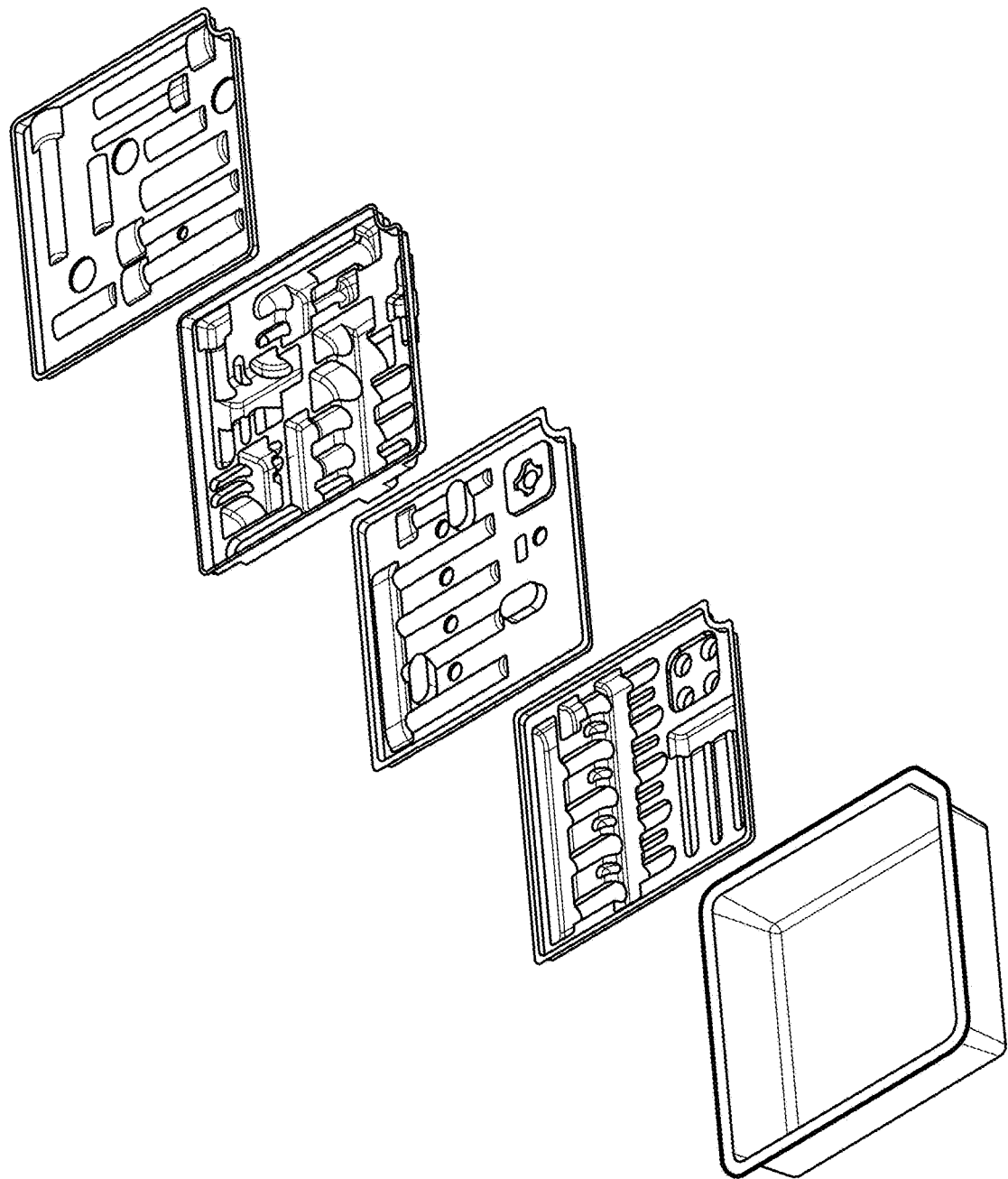
FIG. 10A is a perspective view of a four-piece embodiment of packaging for a set of tools comprising two clamshell tool set pairings, and a bottom tray configured to receive the set of tools.

FIG. 10A generally discloses a perspective view of a four-piece embodiment of packaging for a set of tools comprising two clamshell tool set pairings, and a bottom tray configured to receive the set of tools. In embodiments, the present disclosure may provide for two clamshell pairings, each of which may contain one-half of a negative shape of a tool configured as a recess to receive said tool, wherein the tool is intended for use as part of a system for automated preparation of a cell suspension or as an accompaniment to a system for automated preparation of a cell suspension, and each piece may comprise the mirror image of the other. Accordingly, when placed together, each clamshell pairing may be configured to removably contain one or more tools. As may be seen in FIG. 10A, in some embodiments the present disclosure may comprise two clamshell pairings. In other embodiments, a system for automated preparation of a cell suspension may comprise one clamshell pairing containing tools, two clamshell pairings containing tools, three clamshell pairings containing tools, or four or more clamshell pairings containing tools.

It is contemplated that some embodiments, the one or more tools configured for use with a system for automated preparation of a cell suspension may be contained in a tray having a shape other than the clamshell pairing configuration shown in FIG. 10A. By way of illustration and not limitation, the tools may in some embodiments be contained within a single tray, two trays, or three or more trays, wherein the one or more trays comprise one or more recesses configured to receive one side of each tool and a protective removable covering disposed along the surface of the tray.

In the embodiment generally disclosed in FIG. 10A, the bottom tray is shown as an open-topped pan with an in-cut design at one corner and an upper lip disposed along the entirety of the opening. However, in other embodiments, the bottom tray may comprise a box, a bag, a sphere, or any other shape of object able to contain tools. Similarly, in some embodiments, the tray element and one or more clamshell pairing pieces may not comprise the in-cut corner element, or may comprise two or more in-cut corner elements.

Figure 10B:
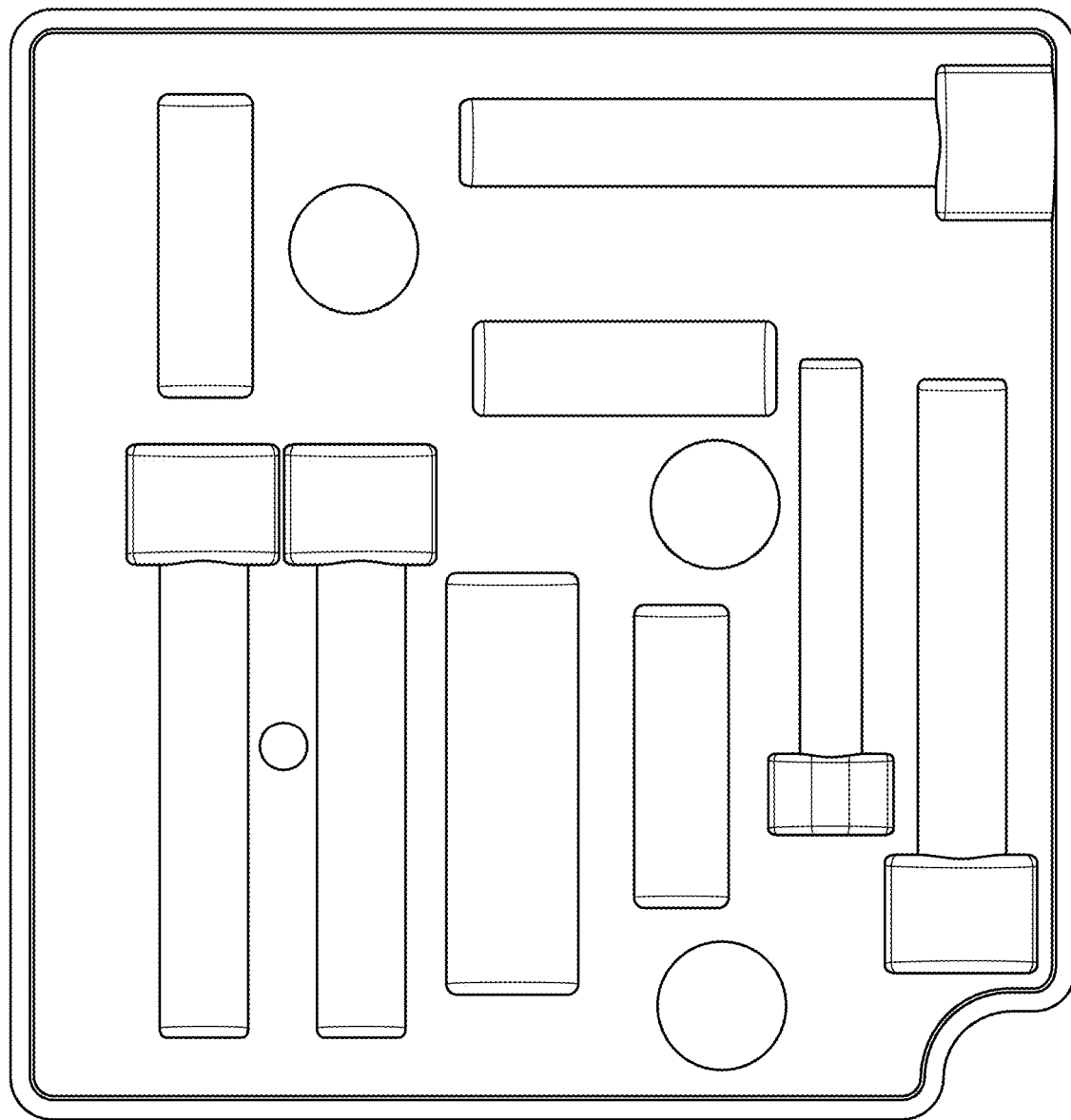
FIG. 10B is a top planar view of an upper clamshell piece for a first clamshell tool set pairing.

FIG. 10B is a top planar view of an upper clamshell piece for a first clamshell tool set pairing. In some embodiments, the recesses of the clamshell piece shown in FIG. 10B may be configured to receive one or more scalpels, one or more syringes, one or more needles, and one or more vials. In some embodiments, the recesses of the clamshell piece shown in FIG. 10B may be configured to contain two or more sizes of tools, such as small, medium or large scalpels; small, medium or large syringes; small, medium or large needles; and small, medium or large vials. In some embodiments, the vials may contain an enzyme solution or a buffer solution. Other embodiments may comprise more or fewer recesses configured to receive a tool, or may comprise recesses configured to receive different tools than the ones shown in FIG. 10B.

Figure 10C:
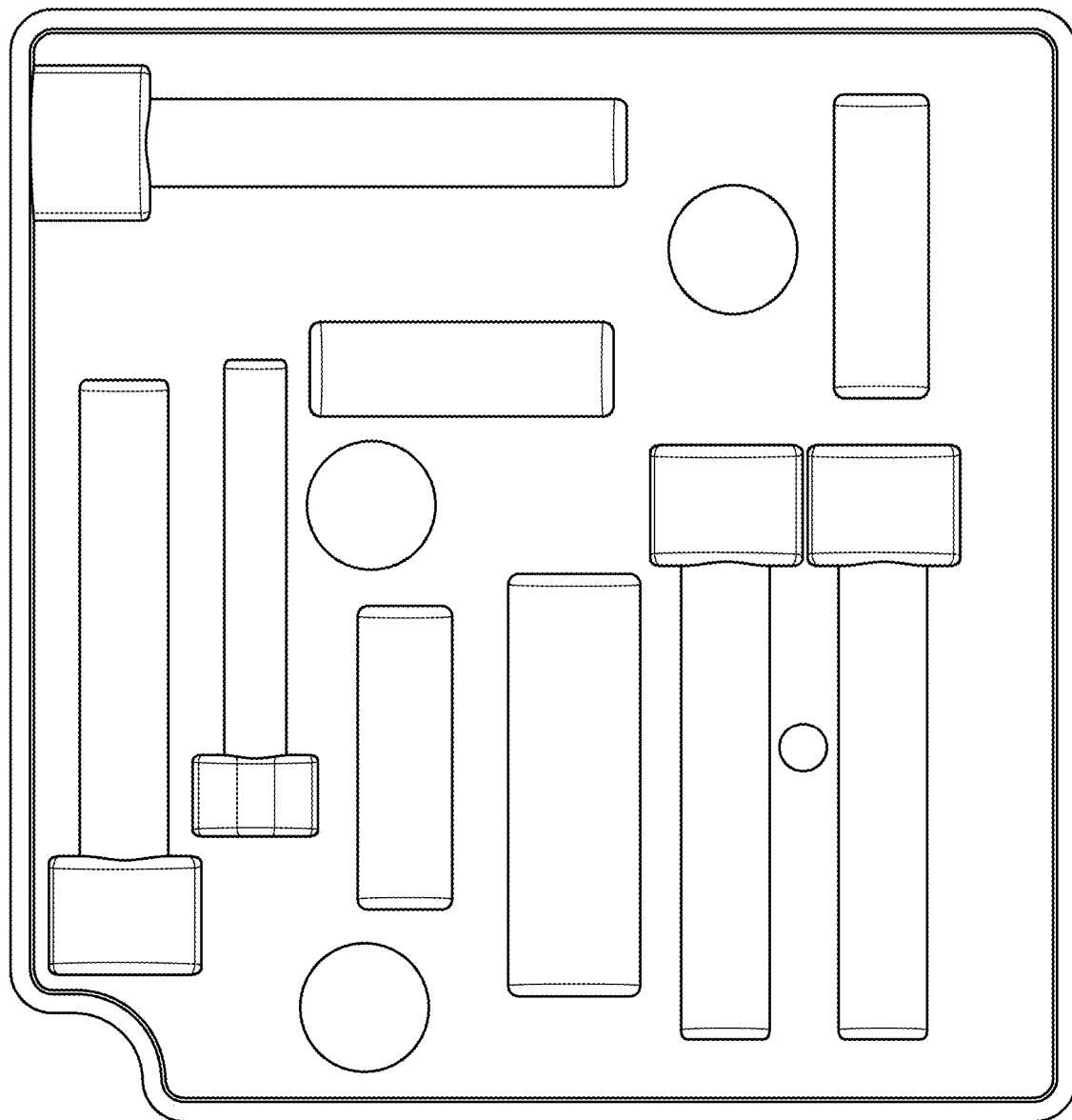
FIG. 10C is a bottom planar view of an upper clamshell piece for a first clamshell tool set pairing.

FIG. 10C is a bottom planar view of an upper clamshell piece for a first clamshell tool set pairing. In some embodiments, the recesses of the clamshell piece shown in FIG. 10C may be configured to receive one or more scalpels, one or more syringes, one or more needles, and one or more vials. In some embodiments, the recesses of the clamshell piece shown in FIG. 10C may be configured to contain two or more sizes of tools, such as small, medium or large scalpels; small, medium or large syringes; small, medium or large needles; and small, medium or large vials. In some embodiments, the vials may contain an enzyme solution or a buffer solution. Other embodiments may comprise more or fewer recesses configured to receive a tool, or may comprise recesses configured to receive different tools than the ones shown in FIG. 10C.

Figure 10D:
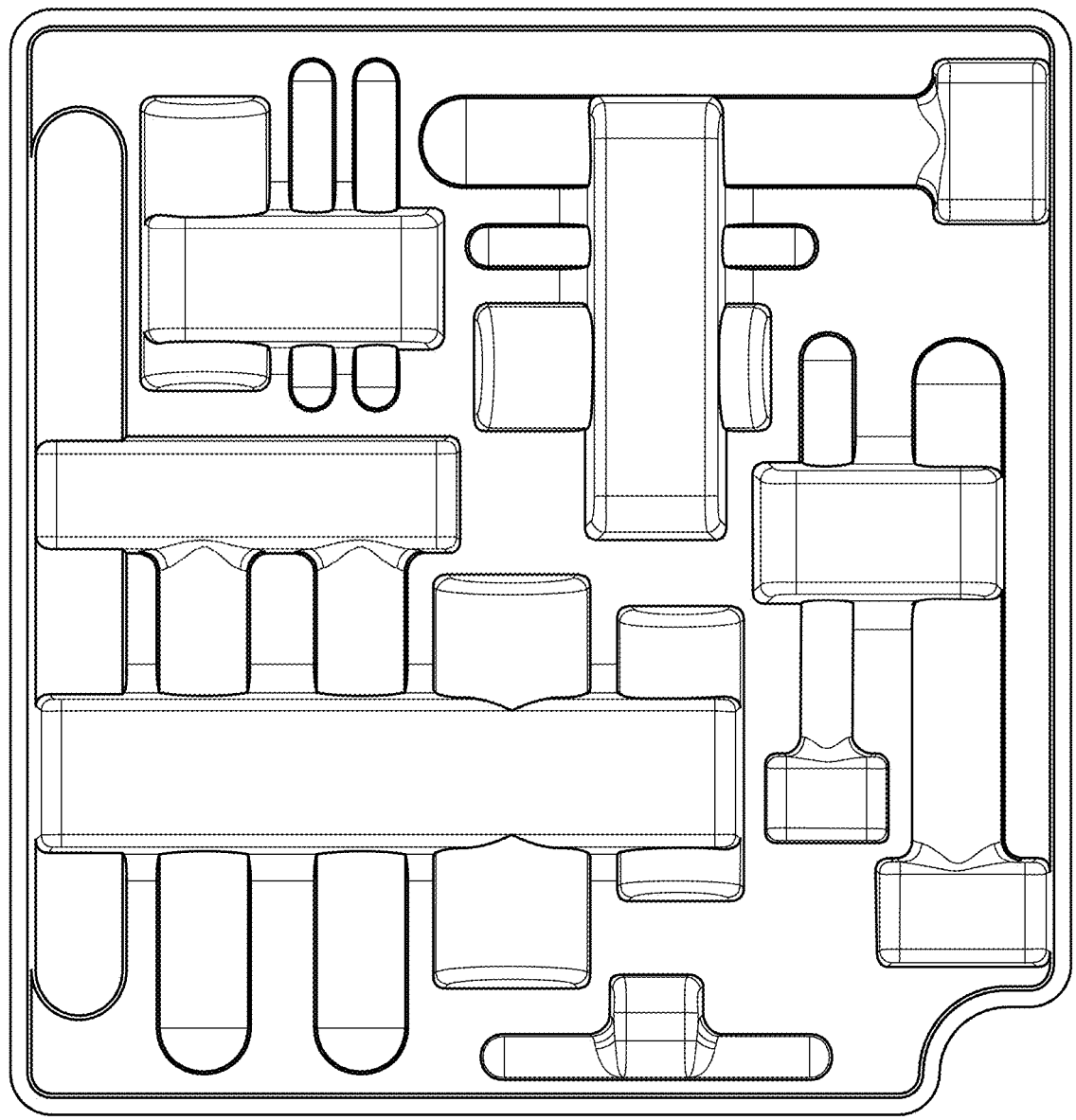
FIG. 10D is a top planar view of a lower clamshell piece for a first clamshell tool set pairing.

FIG. 10D is a top planar view of a lower clamshell piece for a first clamshell tool set pairing. In some embodiments, the recesses of the clamshell piece shown in FIG. 10D may be configured to receive one or more scalpels, one or more syringes, one or more needles, and one or more vials. In some embodiments, the recesses of the clamshell piece shown in FIG. 10D may be configured to contain two or more sizes of tools, such as small, medium or large scalpels; small, medium or large syringes; small, medium or large needles; and small, medium or large vials. In some embodiments, the vials may contain an enzyme solution or a buffer solution. Other embodiments may comprise more or fewer recesses configured to receive a tool, or may comprise recesses configured to receive different tools than the ones shown in FIG. 10D.

Figure 10E:
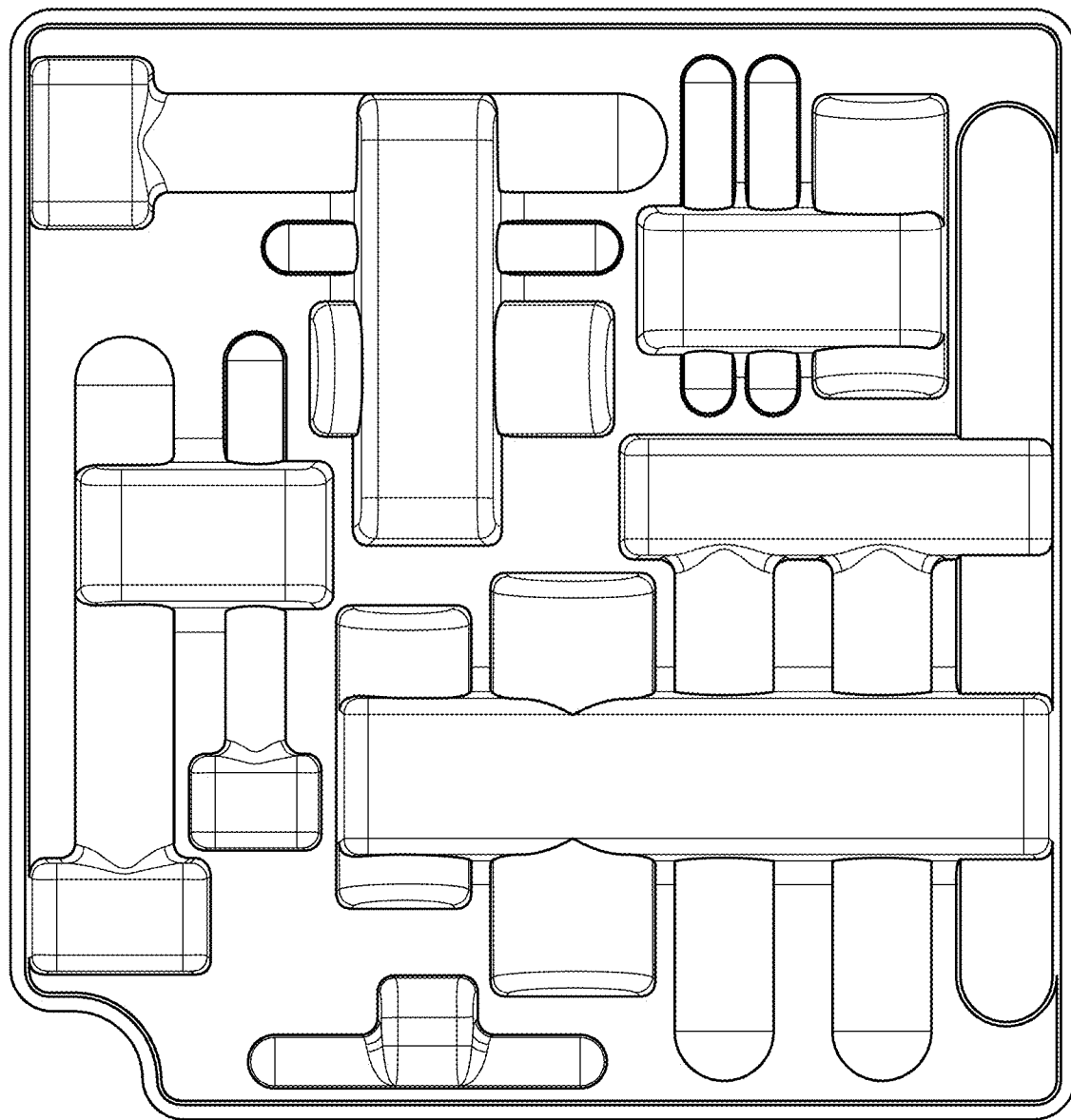
FIG. 10E is a bottom planar view of a lower clamshell piece for a first clamshell tool set pairing.

FIG. 10E is a bottom planar view of a lower clamshell piece for a first clamshell tool set pairing. In some embodiments, the recesses of the clamshell piece shown in FIG. 10E may be configured to receive one or more scalpels, one or more syringes, one or more needles, and one or more vials. In some embodiments, the recesses of the clamshell piece shown in FIG. 10E may be configured to contain two or more sizes of tools, such as small, medium or large scalpels; small, medium or large syringes; small, medium or large needles; and small, medium or large vials. In some embodiments, the vials may contain an enzyme solution or a buffer solution. Other embodiments may comprise more or fewer recesses configured to receive a tool, or may comprise recesses configured to receive different tools than the ones shown in FIG. 10E.

Figure 10F:
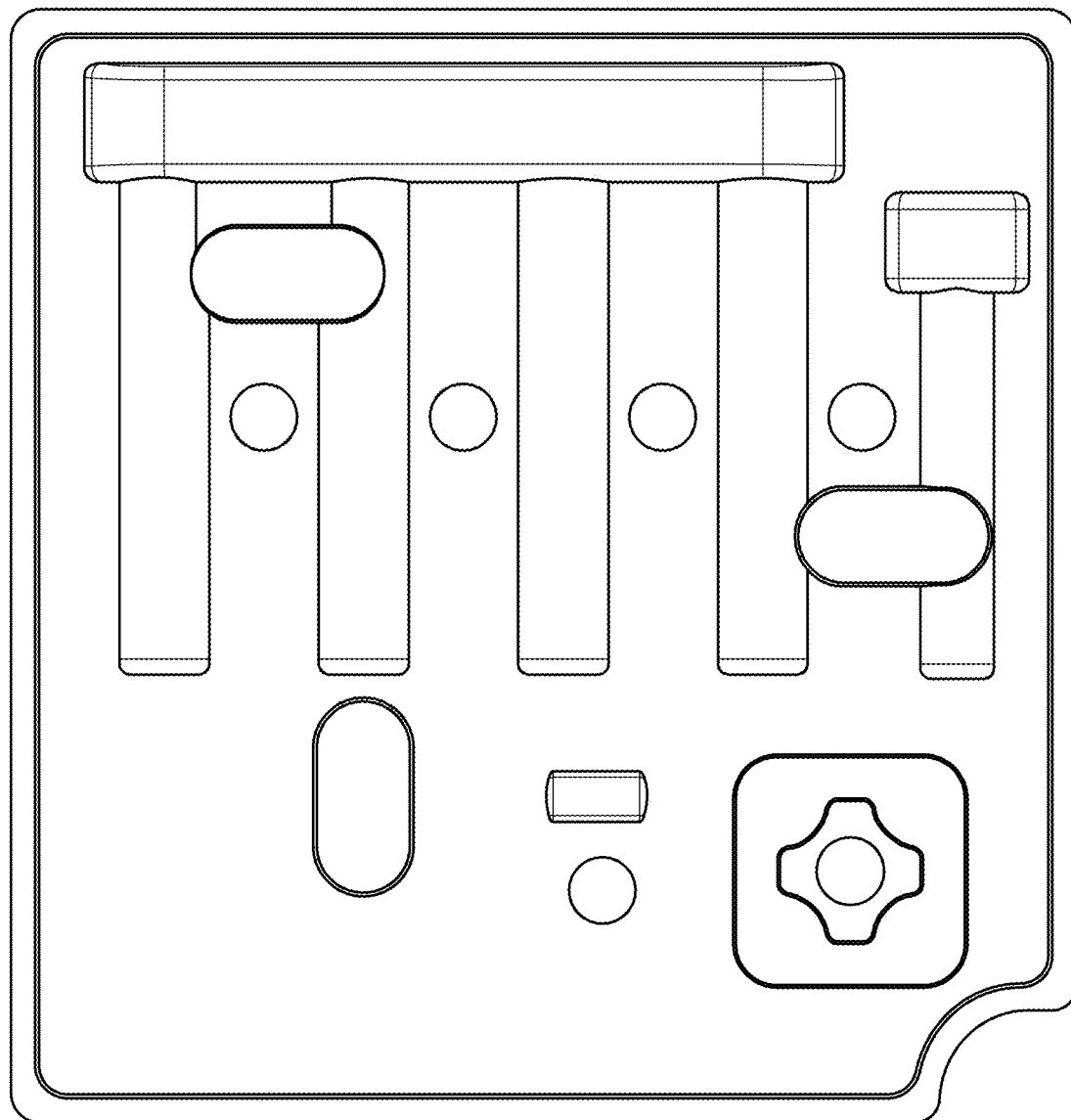
FIG. 10F is a top planar view of an upper clamshell piece for a second clamshell tool set pairing.

FIG. 10F is a top planar view of an upper clamshell piece for a second clamshell tool set pairing. In some embodiments, the recesses of the clamshell piece shown in FIG. 10F may be configured to receive one or more nozzles, one or more syringes, and one or more needles. In some embodiments, the recesses of the clamshell piece shown in FIG. 10F may be configured to contain two or more sizes of tools, such as small, medium or large nozzles; small, medium or large syringes; and small, medium or large needle. In some embodiments, the vials may contain an enzyme solution or a buffer solution. Other embodiments may comprise more or fewer recesses configured to receive a tool, or may comprise recesses configured to receive different tools than the ones shown in FIG. 10F.

Figure 10G:
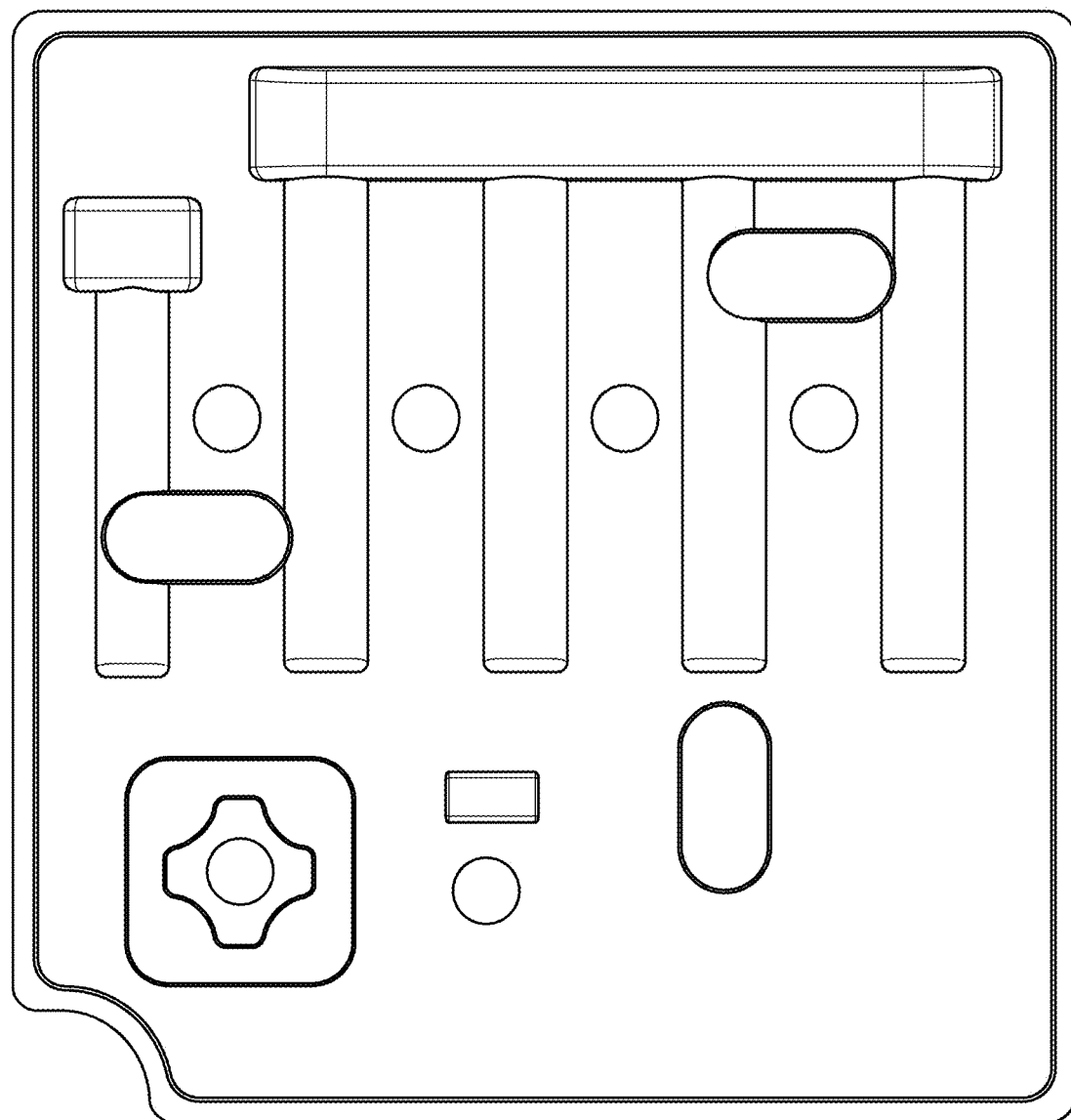
FIG. 10G is a bottom planar view of an upper clamshell piece for a second clamshell tool set pairing.

FIG. 10G is a bottom planar view of an upper clamshell piece for a second clamshell tool set pairing. In some embodiments, the recesses of the clamshell piece shown in FIG. 10G may be configured to receive one or more nozzles, one or more syringes, and one or more needles. In some embodiments, the recesses of the clamshell piece shown in FIG. 10G may be configured to contain two or more sizes of tools, such as small, medium or large nozzles; small, medium or large syringes; and small, medium or large needle. In some embodiments, the vials may contain an enzyme solution or a buffer solution. Other embodiments may comprise more or fewer recesses configured to receive a tool, or may comprise recesses configured to receive different tools than the ones shown in FIG. 10G.

Figure 10H:
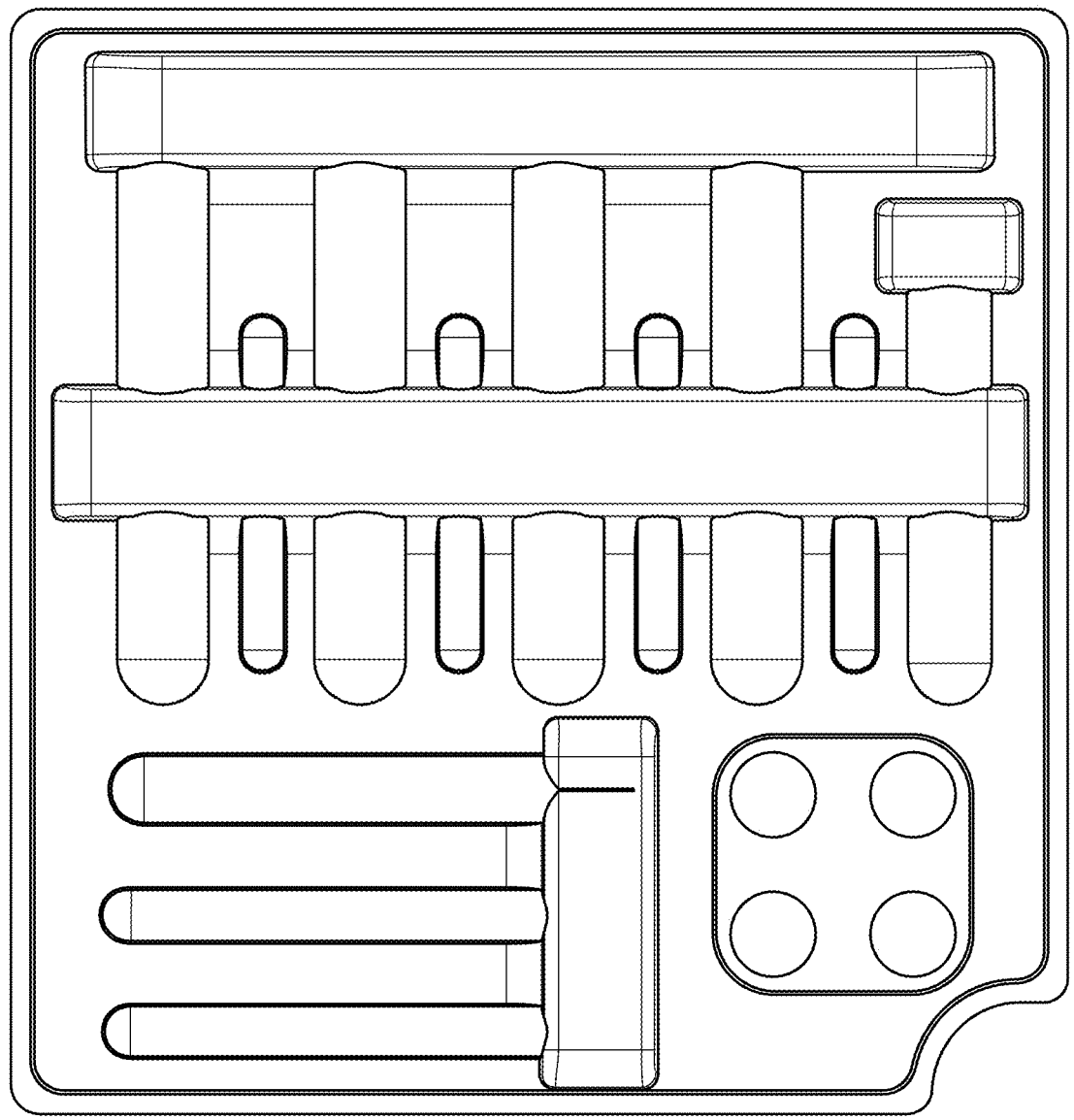
FIG. 10H is a top planar view of a lower clamshell piece for a second clamshell tool set pairing.

FIG. 10H is a top planar view of a lower clamshell piece for a second clamshell tool set pairing. In some embodiments, the recesses of the clamshell piece shown in FIG. 10H may be configured to receive one or more nozzles, one or more syringes, and one or more needles. In some embodiments, the recesses of the clamshell piece shown in FIG. 10H may be configured to contain two or more sizes of tools, such as small, medium or large nozzles; small, medium or large syringes; and small, medium or large needle. In some embodiments, the vials may contain an enzyme solution or a buffer solution. Other embodiments may comprise more or fewer recesses configured to receive a tool, or may comprise recesses configured to receive different tools than the ones shown in FIG. 10H.

Figure 10I:
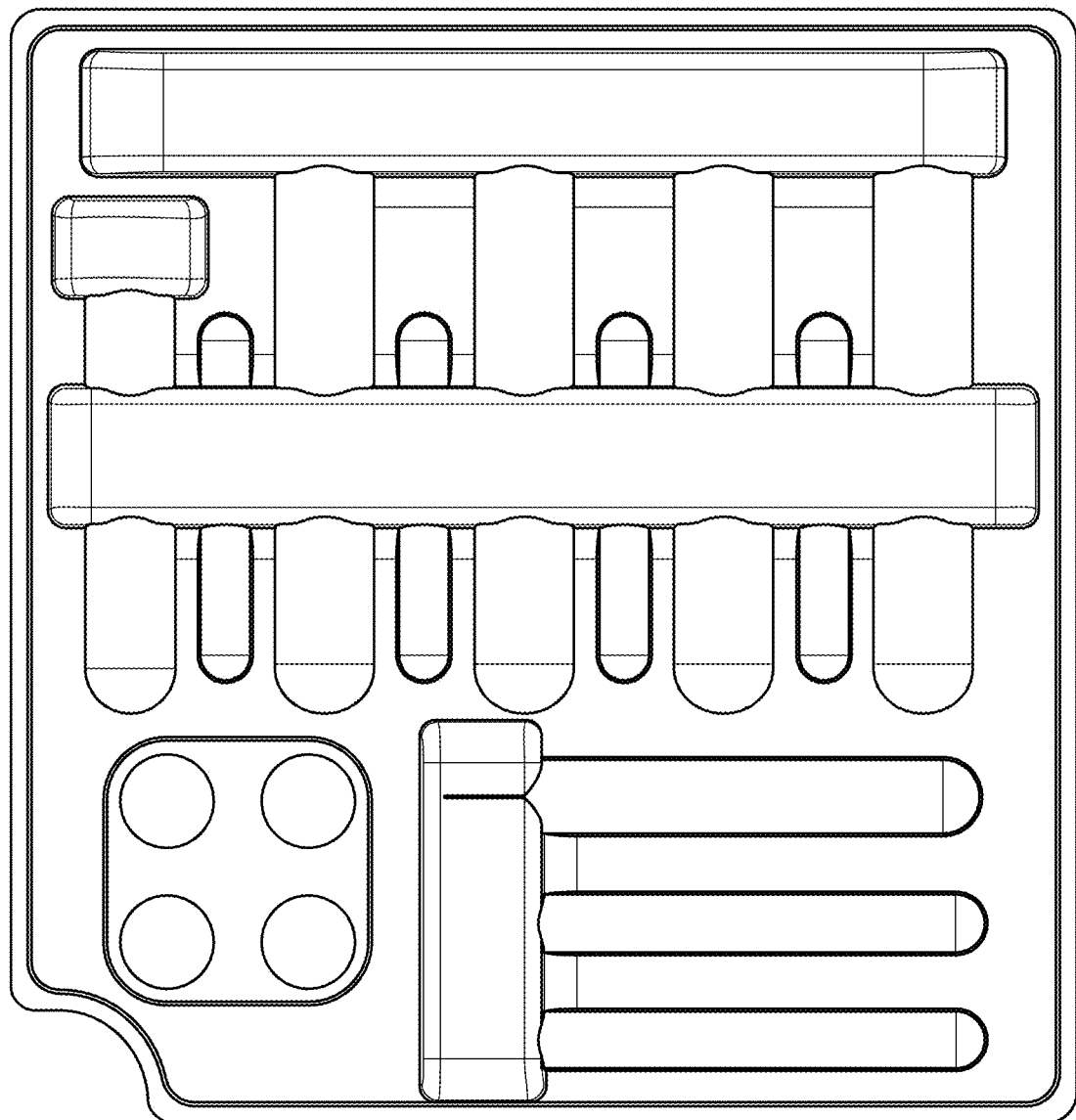
FIG. 10I is a bottom planar view of a lower clamshell piece for a second clamshell tool set pairing.

FIG. 10I is a bottom planar view of a lower clamshell piece for a second clamshell tool set pairing. In some embodiments, the recesses of the clamshell piece shown in FIG. 10I may be configured to receive one or more nozzles, one or more syringes, and one or more needles. In some embodiments, the recesses of the clamshell piece shown in FIG. 10I may be configured to contain two or more sizes of tools, such as small, medium or large nozzles; small, medium or large syringes; and small, medium or large needle. In some embodiments, the vials may contain an enzyme solution or a buffer solution. Other embodiments may comprise more or fewer recesses configured to receive a tool, or may comprise recesses configured to receive different tools than the ones shown in FIG. 10I.

Figure 10J:
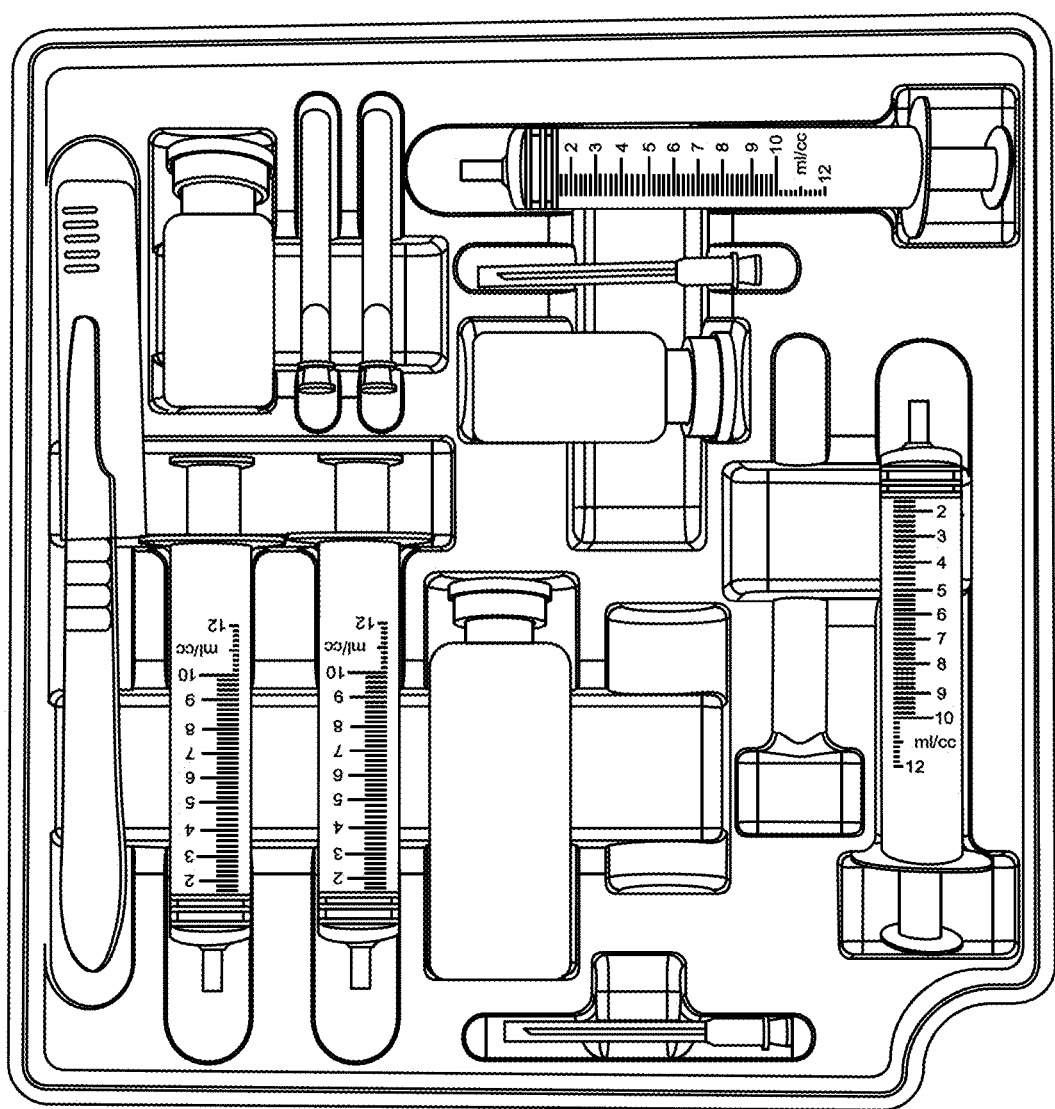
FIG. 10J is a top planar view of a lower clamshell piece for a first clamshell tool set pairing shown containing tools.

FIG. 10J is a top planar view of a lower clamshell piece for a first clamshell tool set pairing shown containing tools. In the embodiment shown in FIG. 10J, a viewer may perceive tools such as one or more scalpels, one or more syringes, one or more needles, and one or more vials.

Figure 10K:
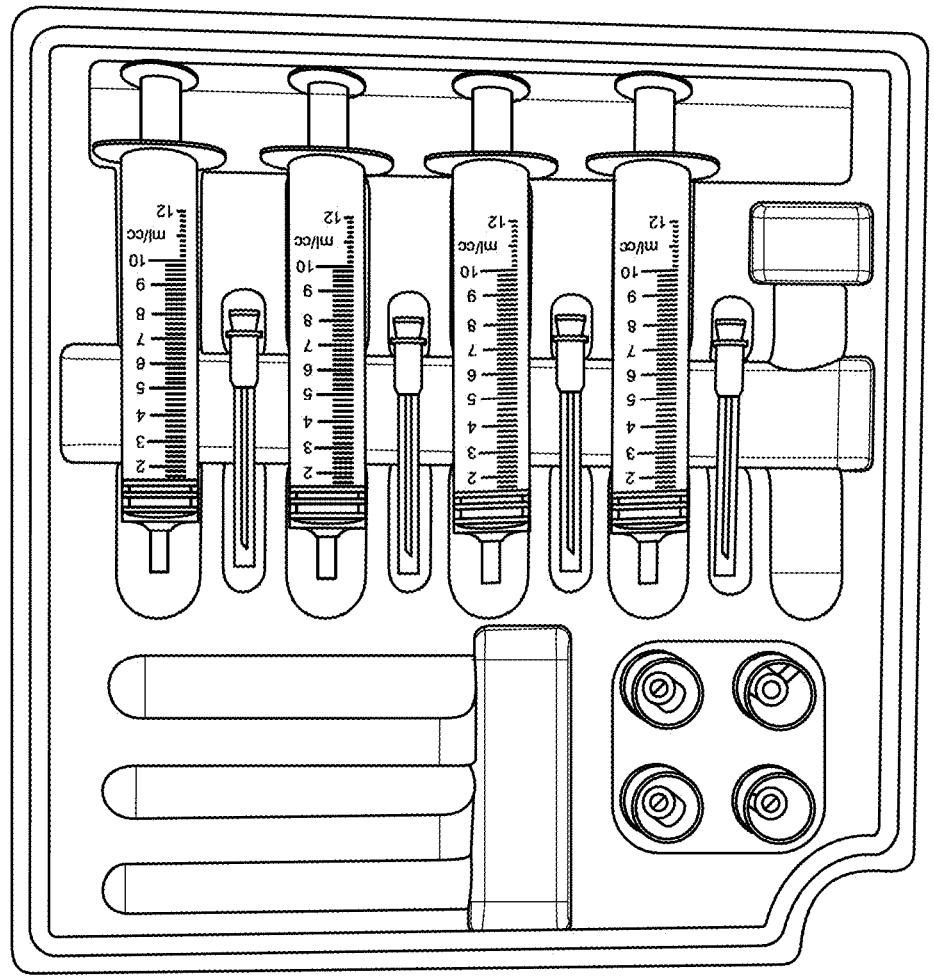
FIG. 10K is a top planar of a lower clamshell piece for a second clamshell tool set pairing shown containing tools.

FIG. 10K is a top planar view of a lower clamshell piece for a second clamshell tool set pairing shown containing tools. In the embodiment shown in FIG. 10K, a viewer may perceive tools such as one or more nozzles, one or more syringes, and one or more needles.

Figure 11:
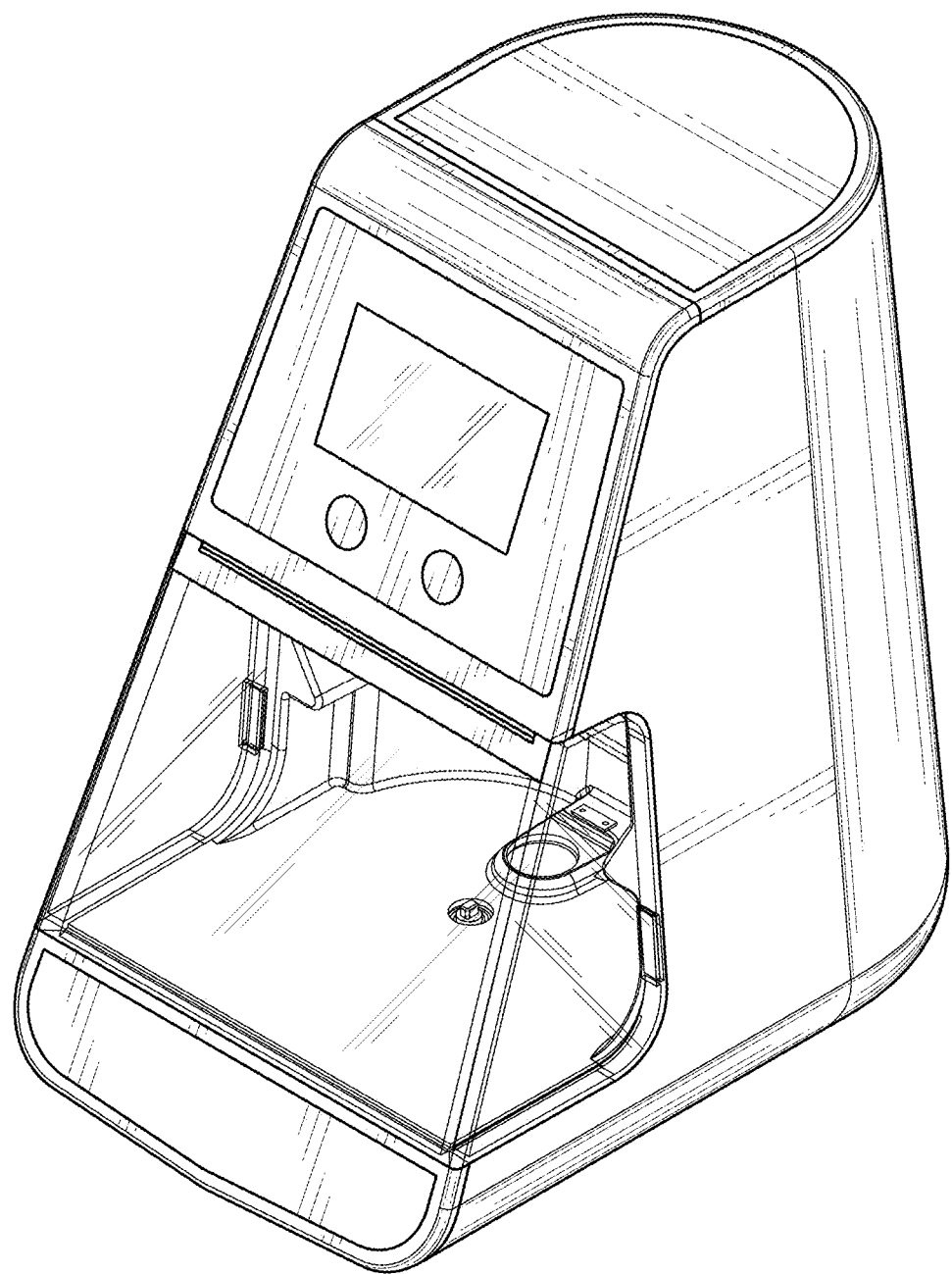
FIG. 11 is a top, front, and right side perspective view of a base unit.

FIG. 11 is a top, front, and right side perspective view of a base unit. FIG. 11 illustrates a base unit, a housing, a tissue processing area, a housing base, a front cover, a heating element, a docking spindle, a display, two menu buttons, side cartridge alignment protrusions, a rear cartridge alignment protrusion, a base frontplate, a housing top surface, and a control feedback sensor.

Figure 12:
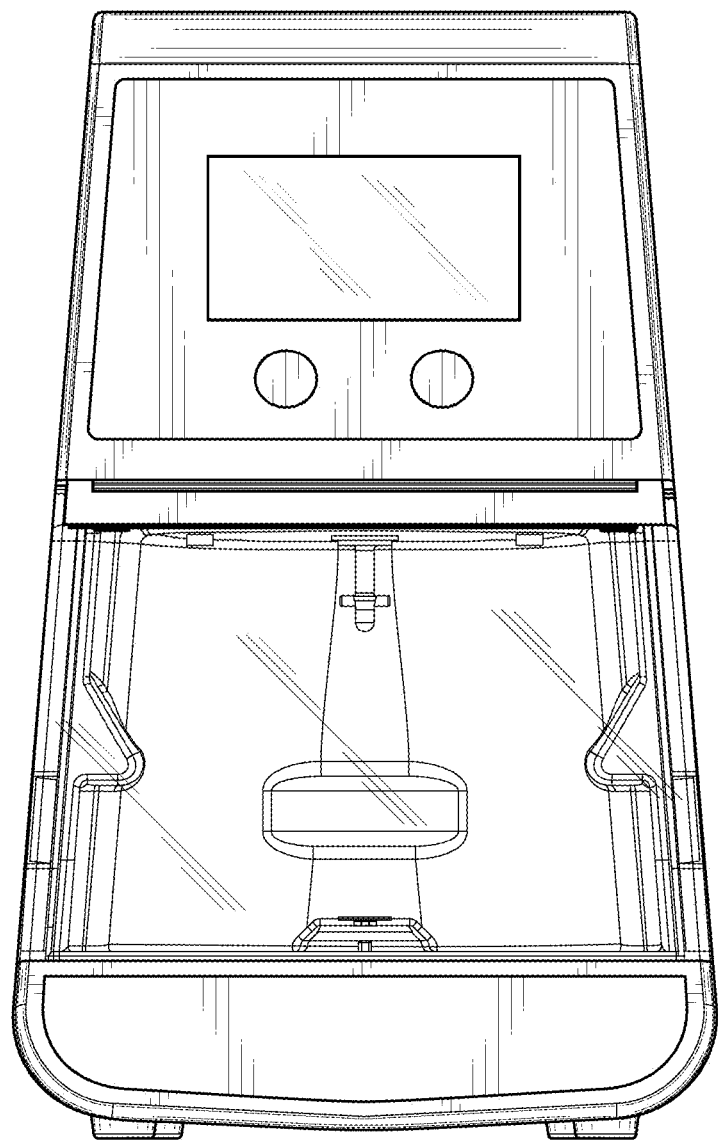
FIG. 12 is a front view of a base unit.
Figure 13:
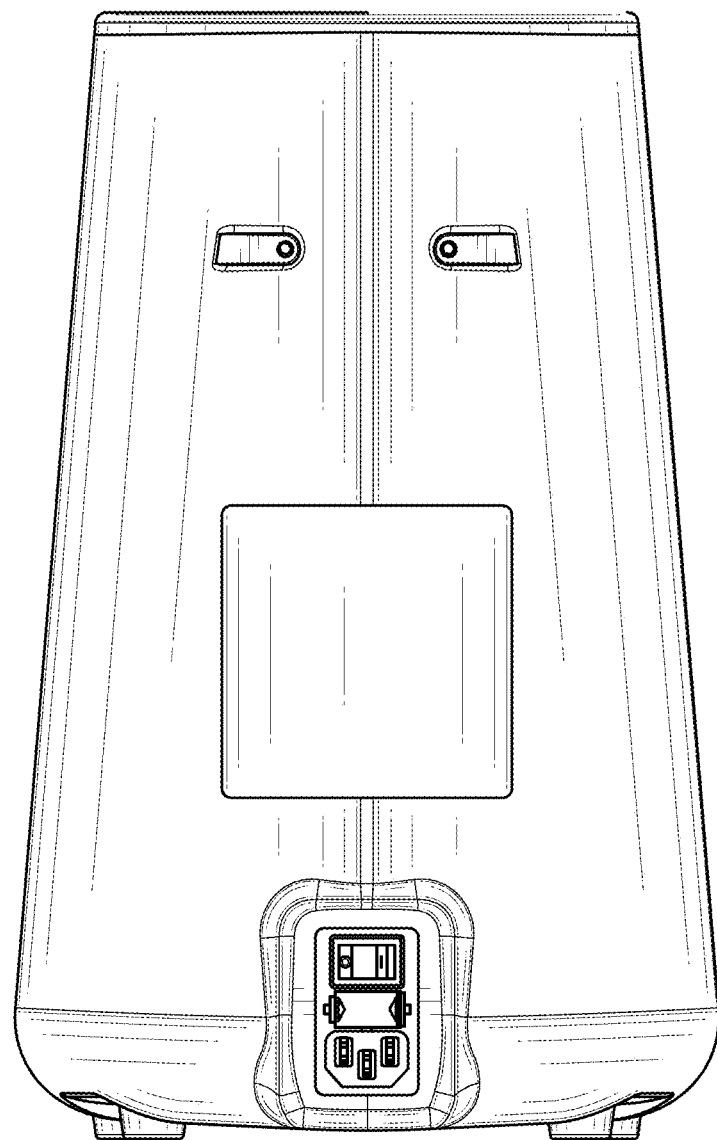
FIG. 13 is a back view of a base unit.
Figure 14:
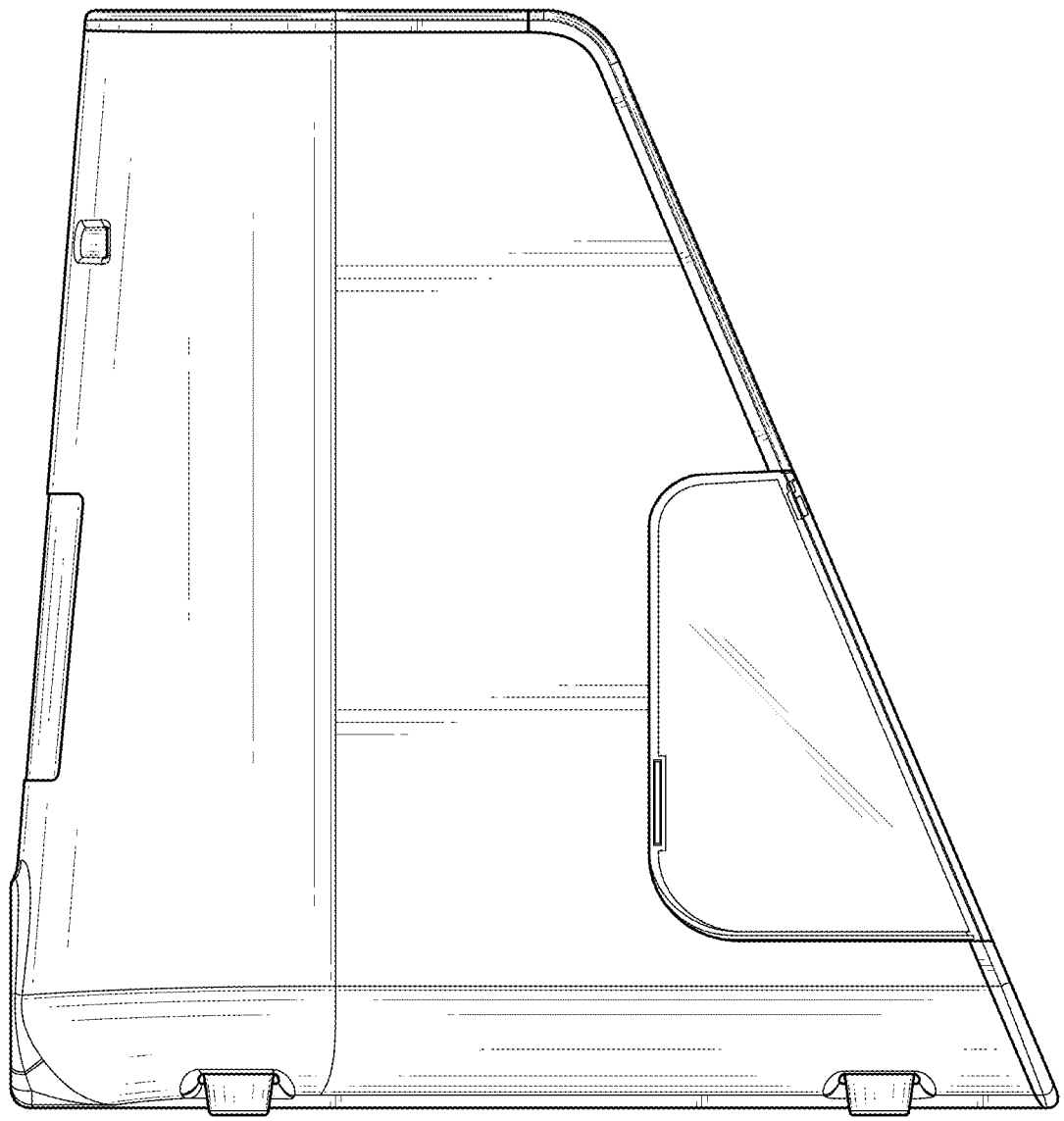
FIG. 14 is a left side view of a base unit.
Figure 15:
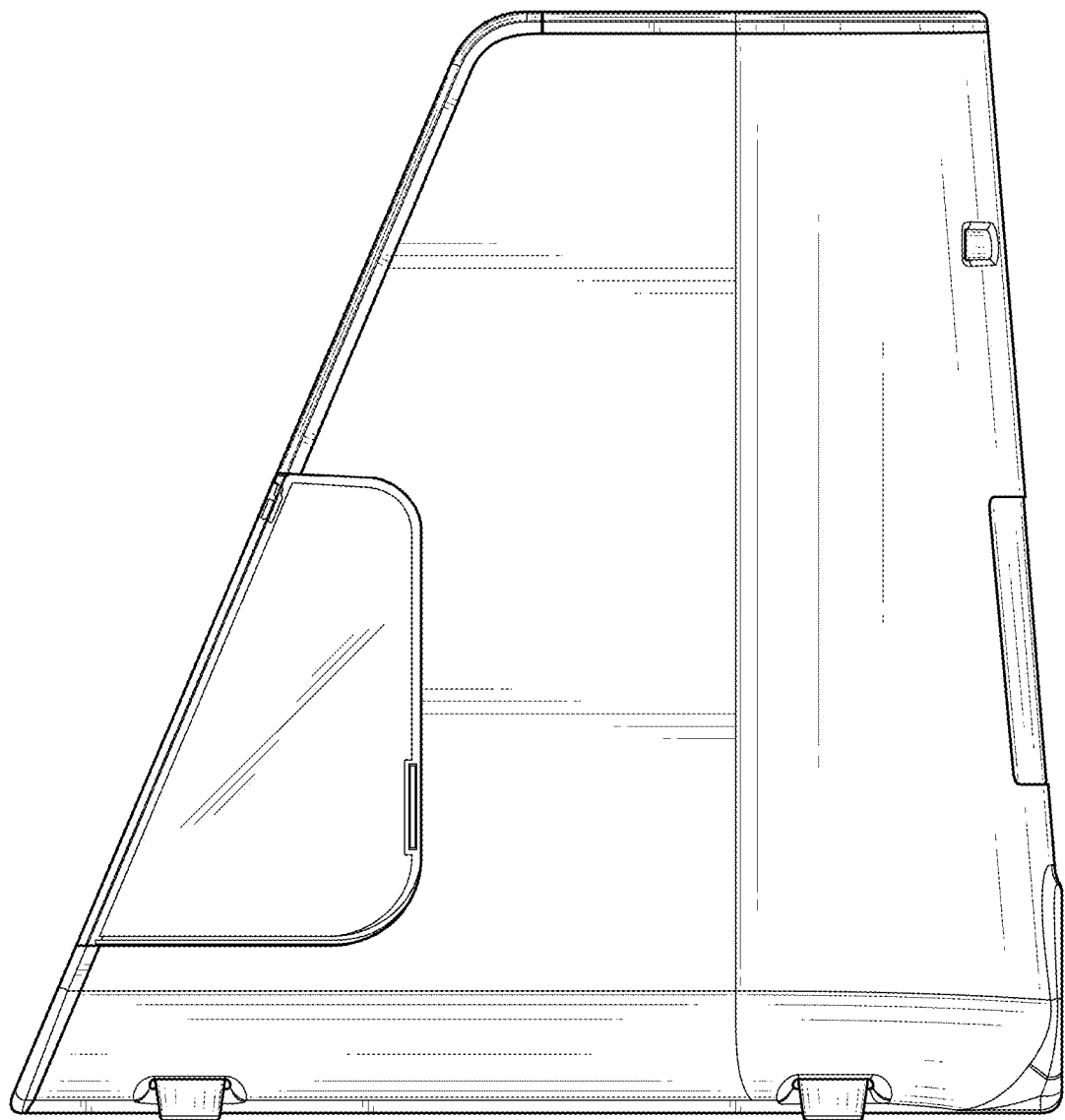
FIG. 15 is a right side view of a base unit.
Figure 16:
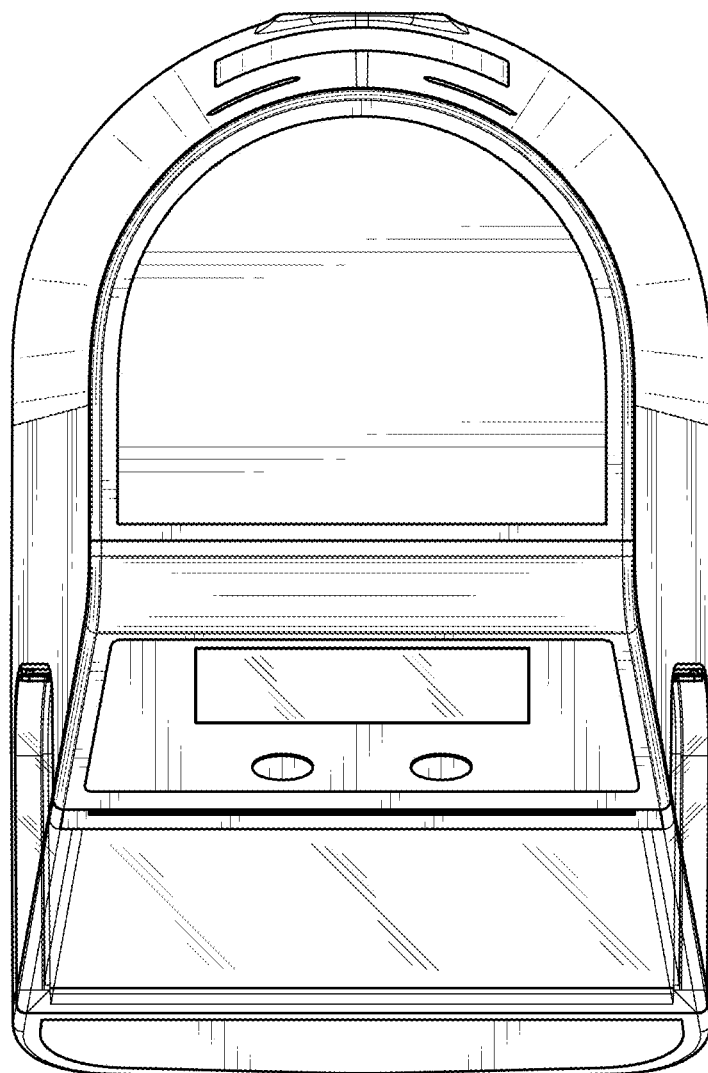
FIG. 16 is a top plan view of a base unit.
Figure 17:
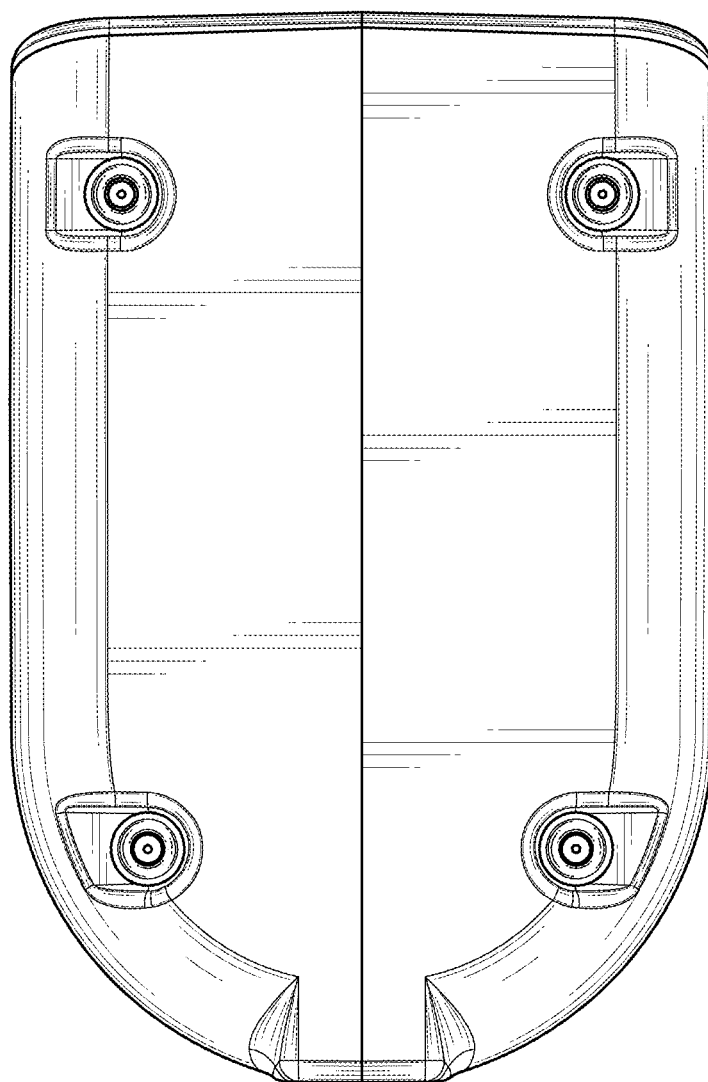
FIG. 17 is a bottom plan view of a base unit.
Figure 18:
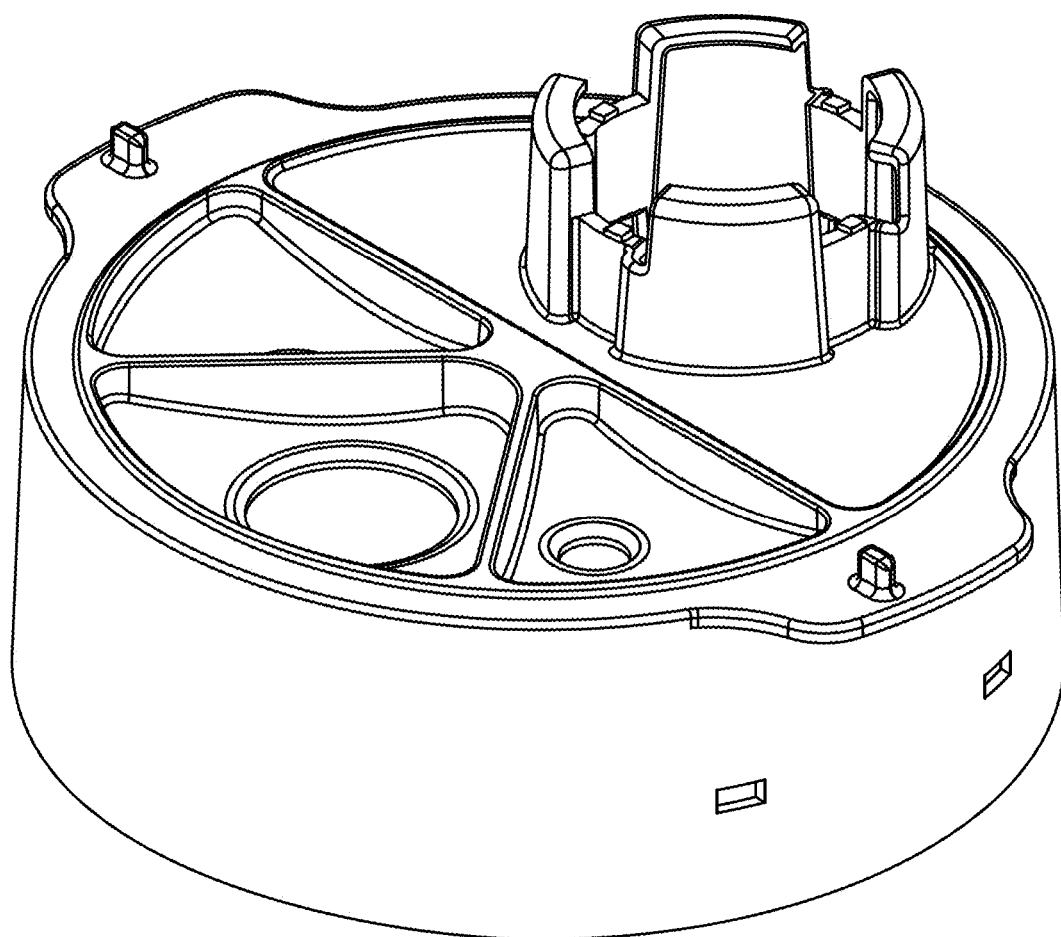
FIG. 18 is a top, front, and right side perspective view of a cartridge.

FIG. 12 is a front view of the base unit of FIG. 11.
FIG. 13 is a back view of the base unit of FIG. 11.
FIG. 14 is a left side view of the base unit of FIG. 11.
FIG. 15 is a right side view the base unit of FIG. 11.
FIG. 16 is a top plan view of the base unit of FIG. 11.
FIG. 17 is a bottom plan view of the base unit of FIG. 11.
FIG. 18 is a top, front, and right side perspective view of a cartridge. FIG. 11 illustrates a cartridge assembly, a cartridge top cover, a raised processing area, an upper processing shelf, four distinct openings, and two cartridge tabs.

Figure 19:
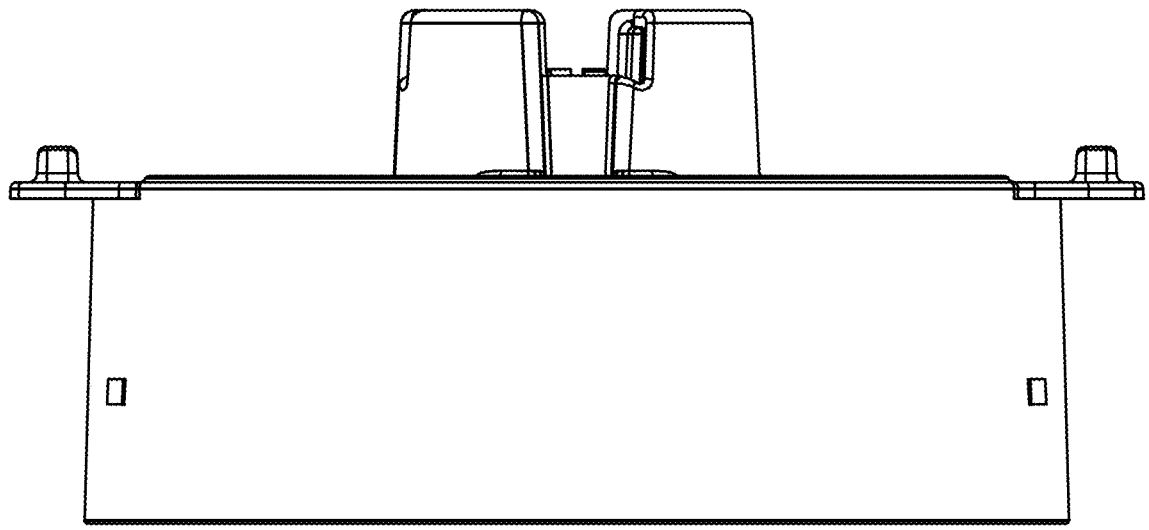
FIG. 19 is a front view of a cartridge.
Figure 20:
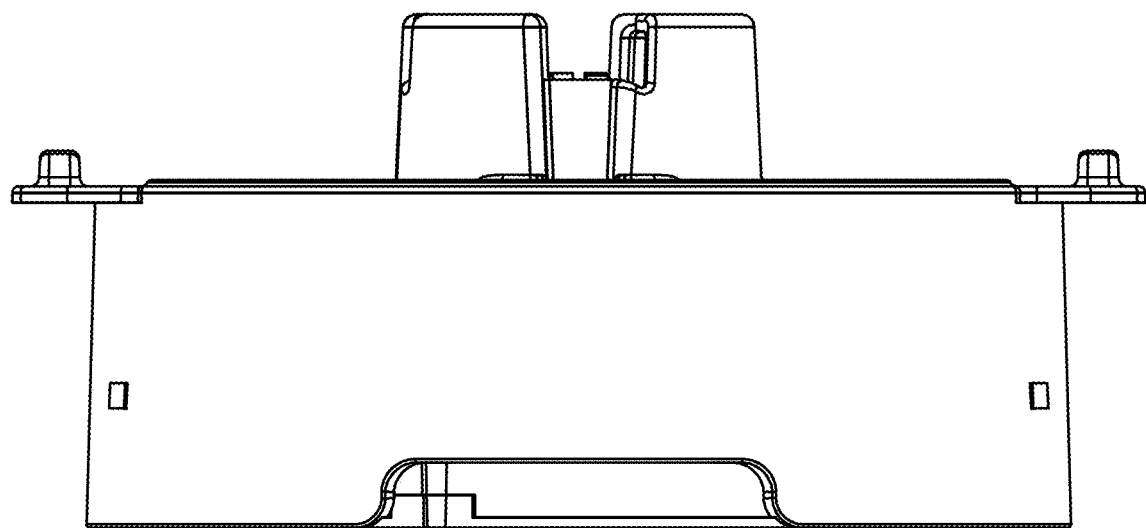
FIG. 20 is a back view of a cartridge.
Figure 21:
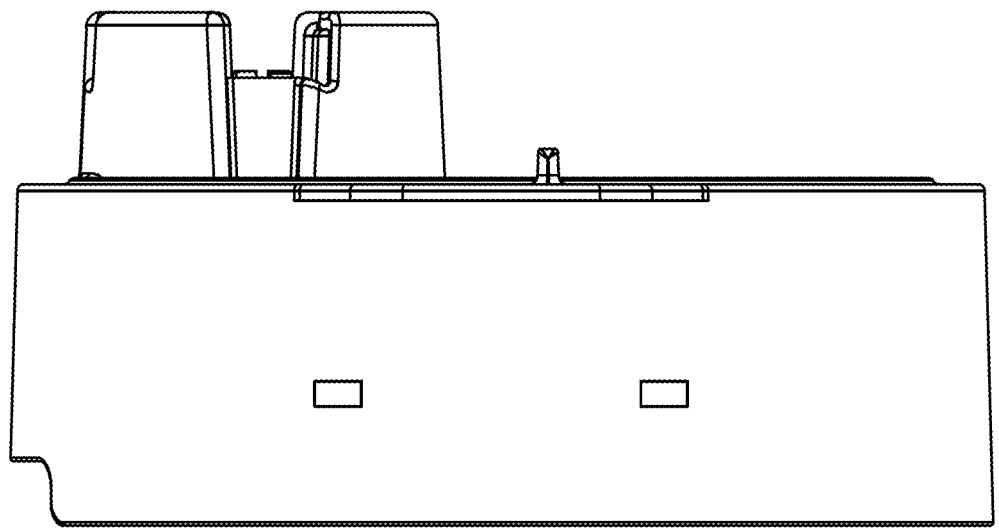
FIG. 21 is a left side view of a cartridge.
Figure 22:
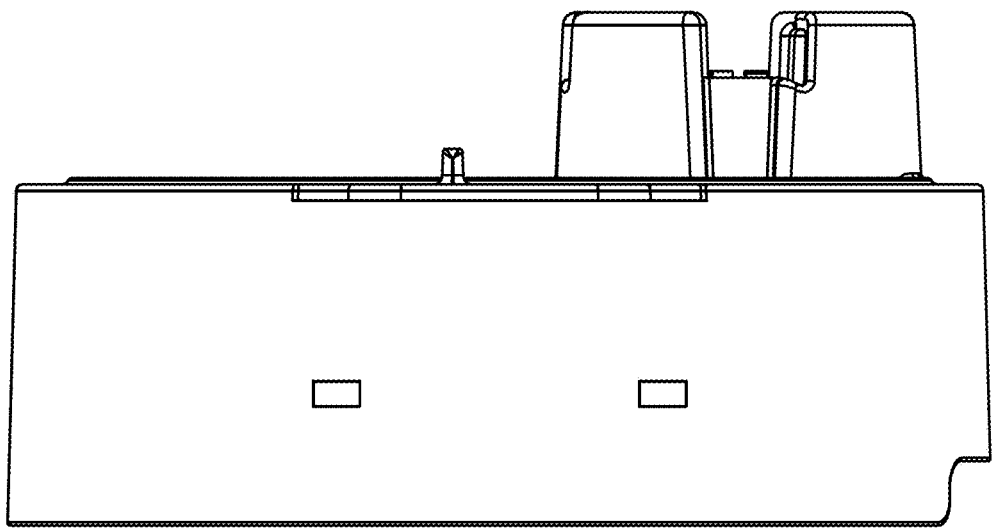
FIG. 22 is a right side view of a cartridge.
Figure 23:
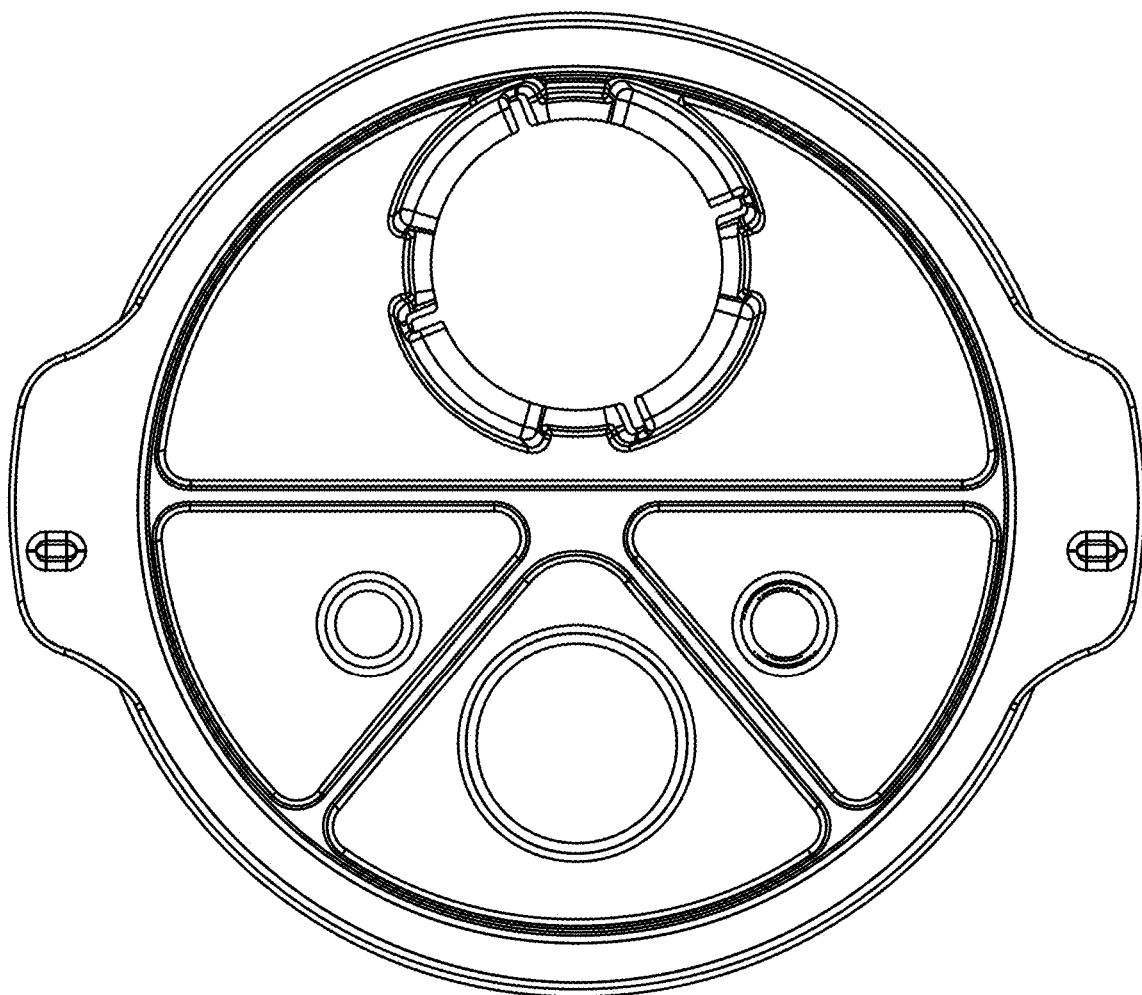
FIG. 23 is a top plan view of a cartridge.
Figure 24:
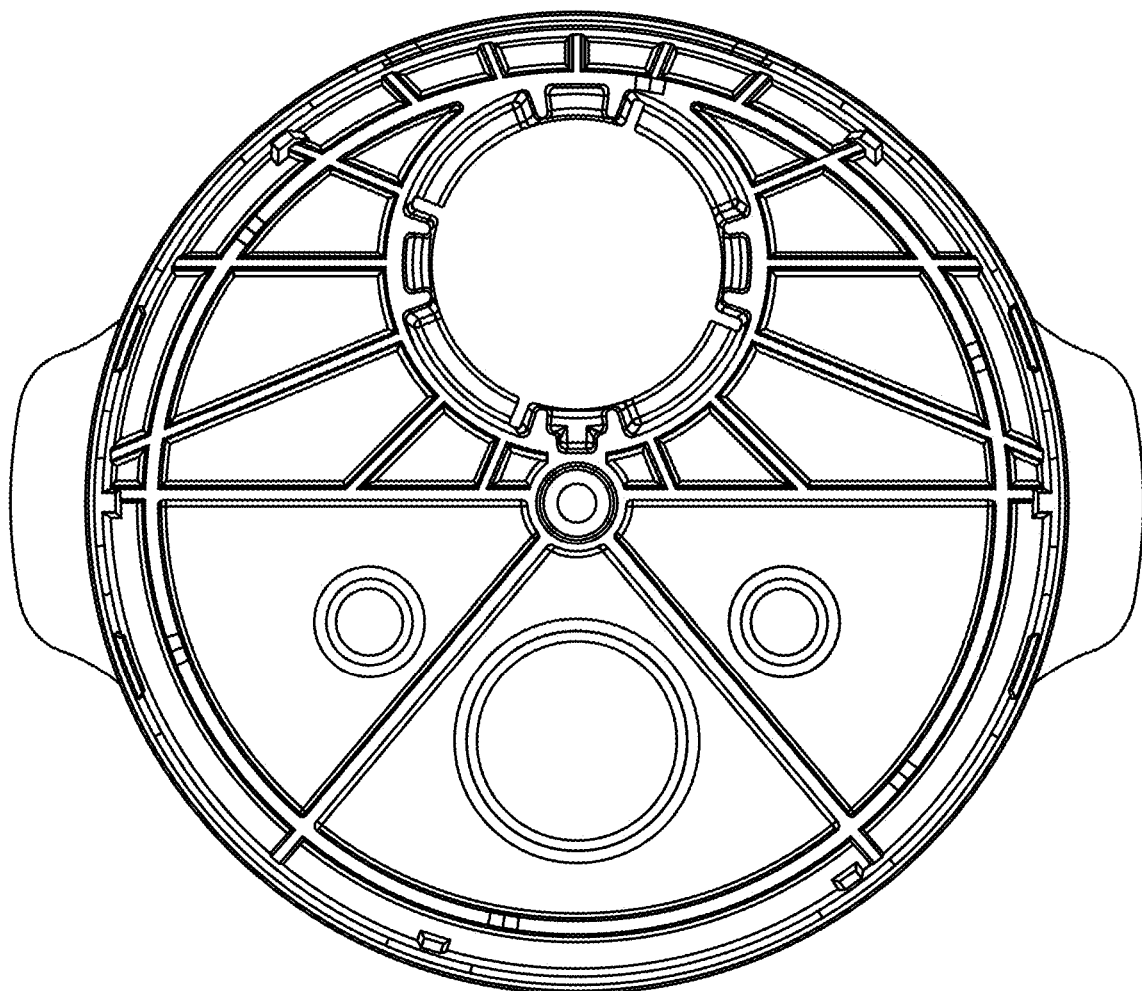
FIG. 24 is a bottom plan view of a cartridge.

FIG. 19 is a front view of the cartridge of FIG. 18.
FIG. 20 is a back view of the cartridge of FIG. 18.
FIG. 21 is a left side view of the cartridge of FIG. 18.
FIG. 22 is a right side view of the cartridge of FIG. 18.
FIG. 23 is a top plan view of the cartridge of FIG. 18.
FIG. 24 is a bottom plan view of the cartridge of FIG. 18.

EXAMPLES AND EXPERIMENTS

Preliminary characterization work has been conducted demonstrating effectiveness of the present disclosure. More specifically, research results indicate that the present system for automated preparation of a regenerative epidermal suspension (or "Automated Device" as used in this section) tends to prepare a regenerative epidermal suspension having equivalent properties as the device generally disclosed by the disclosure of U.S. Pat. No. 9,029,140, the entirety of which is incorporated by reference herein, via a novel and surprising automated system.

Study Background

The purpose of this study was to evaluate the performance of the present system for automated preparation of a regenerative epidermal suspension by assessing device output metrics relevant to biological function.

The RECELL Device is a manual system for preparation of a regenerative epidermal suspension ("Manual Device") that enables a clinician at point-of-care to prepare a regenerative epidermal suspension using a small piece of donor skin.

The Manual Device is a single-use, stand-alone, battery-operated device that enables a thin skin sample (0.006-0.008") to be processed by a healthcare professional at point-of-care to prepare regenerative epidermal suspension for immediate delivery onto a prepared wound bed. Regenerative epidermal suspension contains a mixed population of single and generally viable cells, including keratinocytes, fibroblasts, and melanocytes, that are obtained from enzymatic and mechanical processing of the split-thickness skin sample. The cell suspension is applied to a prepared wound bed for the treatment of acute thermal burn wounds and full-thickness skin defects.

The present disclosure and its Automated Device was designed and manufactured to overcome the challenges and shortcomings of previously known methods and devices, and to simplify preparation of regenerative epidermal suspension.

Study Procedure

Trained operators prepared regenerative epidermal suspension using a Manual Device and the Automated Device. For each processing sequence, the trained operators obtained two skin samples of identical size from adjacent locations on the same piece of donor skin. Then, simultaneously, operators used the Manual Device and the Automated Device to produce regenerative epidermal suspension from the identically-sized and same-donor skin samples. The operators repeated this process a total of six times: three times wherein each device was used to produce regenerative epidermal suspension from a 4 $cm^2$ skin sample, and three times wherein each device was used to produce regenerative epidermal suspension from a 24 $cm^2$ skin sample. Then, the parameters of the regenerative epidermal suspension obtained from each device were obtained and analyzed.

Study Discussion

Collectively, the analyses indicate successful disaggregation of skin and isolation of cells for the lower and upper limit of skin sample sizes for both devices. Additionally, similar functional outputs were isolated for the Automated Device compared to the Manual Device. Collectively, the analyses indicate that both devices disaggregate the lower and upper limit of skin sample sizes with comparable results.

Study Conclusion

The data from this study demonstrates that the Automated Device produces regenerative epidermal suspension with comparable device output characteristics relevant to biological function to that prepared using the Manual Device for skin sample sizes at the lower and upper limit for processing.

Although certain embodiments described herein relate to tissue treatment and regenerative epidermal suspension, devices, systems and methods disclosed herein are not limited to these applications. Systems and methods disclosed herein are generally applicable to medical devices in general.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some cases, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of treating a tissue site, comprising:
collecting a tissue sample and placing the tissue sample in a cartridge comprising a well plate, the tissue sample comprising keratinocytes;
positioning the cartridge within a base unit, the base unit comprising a tissue disaggregator;
via a processor, activating the base unit to rotate the well plate and operate the tissue disaggregator, wherein the well plate is rotated to align one or more wells in the well plate with the tissue sample and the tissue disaggregator, and wherein operation of the tissue disaggregator separates the tissue sample to form a regenerative epidermal suspension; and
providing the regenerative epidermal suspension to a tissue site such that healing of the tissue site is enhanced.

2. The method of claim 1, wherein the tissue sample comprises a skin sample.

3. The method of claim 1, wherein the regenerative epidermal suspension comprises a mixed population of viable cells.

4. The method of claim 1, wherein the regenerative epidermal suspension comprises fibroblasts.

5. The method of claim 1, wherein the regenerative epidermal suspension comprises melanocytes.

6. The method of claim 1, wherein the tissue site is a burn tissue site.

7. The method of claim 1, wherein the tissue site is a full-thickness skin defect.

8. The method of claim 1, wherein the cartridge further comprises a cover comprising a raised processing opening.

9. The method of claim 8, further comprising placing the tissue sample in a cup positioned within the raised processing opening.

10. The method of claim 9, wherein activating the base unit causes the cup to be lowered into a well of the well plate.

11. The method of claim 1, wherein the tissue disaggregator is a pestle.

12. The method of claim 1, wherein the well plate comprises an enzyme well.

13. The method of claim 12, further comprising placing an enzyme within the enzyme well, the enzyme configured to separate tissue.

14. The method of claim 12, wherein the well plate is positioned such that the enzyme well is positioned beneath the tissue sample.

15. The method of claim 12, wherein activating the base unit causes the tissue aggregator to act on the tissue sample in the presence of enzyme in the enzyme well.

16. The method of claim 1, wherein the well plate comprises a buffer well.

17. The method of claim 16, further comprising placing a buffer within the buffer well.

18. The method of claim 16, wherein activating the base unit causes the well plate to rotate such that the buffer well is positioned beneath the tissue sample.

19. The method of claim 18, wherein activating the base unit causes the tissue aggregator to act on the tissue sample in the presence of the buffer in the buffer well.

20. The method of claim 1, wherein the well comprises one or more raised processing elements.

* * * * *